US011066357B2

(12) United States Patent
Pathak et al.

(10) Patent No.: US 11,066,357 B2
(45) Date of Patent: Jul. 20, 2021

(54) BENZOANNULENE DERIVATIVES AS ANTIVIRAL AGENTS

(71) Applicant: Southern Research Institute, Birmingham, AL (US)

(72) Inventors: Ashish Kumar Pathak, Hoover, AL (US); Syed Kaleem Ahmed, Hoover, AL (US); Mark J. Suto, Homewood, AL (US); Corinne E. Augelli-Szafran, Homewood, AL (US)

(73) Assignee: SOUTHERN RESEARCH INSTITUTE, Memphis, TN (US)

( * ) Notice: Subject to any disclaimer, the term of this patent is extended or adjusted under 35 U.S.C. 154(b) by 0 days.

(21) Appl. No.: 16/954,464

(22) PCT Filed: Dec. 24, 2018

(86) PCT No.: PCT/US2018/067454
§ 371 (c)(1),
(2) Date: Jun. 16, 2020

(87) PCT Pub. No.: WO2019/133574
PCT Pub. Date: Jul. 4, 2019

(65) Prior Publication Data
US 2021/0078937 A1    Mar. 18, 2021

Related U.S. Application Data

(60) Provisional application No. 62/610,486, filed on Dec. 26, 2017.

(51) Int. Cl.
*A61K 31/55* (2006.01)
*C07C 233/65* (2006.01)
*C07C 235/56* (2006.01)
*C07C 235/64* (2006.01)
*C07C 243/38* (2006.01)
*C07C 255/44* (2006.01)
*C07D 211/16* (2006.01)
*C07D 211/38* (2006.01)
*C07D 213/75* (2006.01)
*C07D 221/04* (2006.01)
*C07D 223/16* (2006.01)
*C07D 231/12* (2006.01)
*C07D 231/40* (2006.01)
*C07D 233/88* (2006.01)
*C07D 275/02* (2006.01)
*C07D 277/46* (2006.01)
*C07D 333/36* (2006.01)
*C07D 333/38* (2006.01)
*C07D 401/12* (2006.01)

(52) U.S. Cl.
CPC .......... *C07C 233/65* (2013.01); *C07C 235/56* (2013.01); *C07C 235/64* (2013.01); *C07C 243/38* (2013.01); *C07C 255/44* (2013.01); *C07D 211/16* (2013.01); *C07D 211/38* (2013.01); *C07D 213/75* (2013.01); *C07D 221/04* (2013.01); *C07D 223/16* (2013.01); *C07D 231/12* (2013.01); *C07D 231/40* (2013.01); *C07D 233/88* (2013.01); *C07D 275/02* (2013.01); *C07D 277/46* (2013.01); *C07D 333/36* (2013.01); *C07D 333/38* (2013.01); *C07D 401/12* (2013.01); *C07C 2602/12* (2017.05)

(58) Field of Classification Search
None
See application file for complete search history.

(56) References Cited

U.S. PATENT DOCUMENTS

| 9,427,440 B2 | 8/2016 | Vendeville et al. |
| 10,450,263 B2 | 10/2019 | Pathak et al. |
| 2016/0289216 A1 | 10/2016 | Jones et al. |
| 2018/0230084 A1 | 8/2018 | Pathak et al. |

FOREIGN PATENT DOCUMENTS

| WO | WO 2016-097761 A1 | 6/2016 |
| WO | PCT/US2018/067454 | 12/2018 |
| WO | WO 2019-133574 | 7/2019 |

OTHER PUBLICATIONS

Nonfinal Office Action dated Feb. 11, 2019 by the U.S. Patent and Trademark Office for U.S. Appl. No. 15/892,302, filed Feb. 8, 2018 now U.S. Pat. No. 10,450,263 on Oct. 22, 2019 (Applicant—Southern Research Institute, et al.) (8 pages).
Response to Nonfinal Office Action filed on May 13, 2019 for U.S. Appl. No. 15/892,302, filed Feb. 8, 2018 now U.S. Pat. No. 10,450,263 on Oct. 22, 2019 (Applicant—Southern Research Institute, et al.) (9 pages).
Notice of Allowance dated Jun. 6, 2019 by the U.S. Patent and Trademark Office for U.S. Appl. No. 15/892,302, filed Feb. 8, 2018 now U.S. Pat. No. 10,450,263 on Oct. 22, 2019 (Applicant—Southern Research Institute, et al.) (6 pages).
Notice of Allowance dated Aug. 13, 2019 by the U.S. Patent and Trademark Office for U.S. Appl. No. 15/892,302, filed Feb. 8, 2018 now U.S. Pat. No. 10,450,263 on Oct. 22, 2019 (Applicant—Southern Research Institute, et al.) (2 pages).
International Search Report and Written Opinion dated Apr. 23, 2019 by the International Searching Authority for Application No. PCT/US2018/067454 filed on Dec. 24, 2018 and published as WO 2019/133574 on Jul. 4, 2019 (Applicant—Southern Research Institute, et al.) (12 pages).
U.S. Appl. No. 62/457,653, filed Feb. 10, 2017, Pathak, et al.
U.S. Appl. No. 15/892,302 (U.S. Pat. No. 10,450,263), filed Feb. 8, 2018 (Oct. 22, 2019), Pathak, et al.
U.S. Appl. No. 62/610,486, filed Dec. 26, 2017, Pathak, et al.

*Primary Examiner* — Samantha L Shterengarts
(74) *Attorney, Agent, or Firm* — Ballard Spahr LLP

(57) ABSTRACT

The present disclosure is concerned with benzoannulene compounds that are capable of inhibiting a viral infection and methods of treating viral infections such as, for example, chikungunya, Venezuelan equine encephalitis, dengue, influenza, and zika, using these compounds. This abstract is intended as a scanning tool for purposes of searching in the particular art and is not intended to be limiting of the present invention.

20 Claims, No Drawings

US 11,066,357 B2

BENZOANNULENE DERIVATIVES AS ANTIVIRAL AGENTS

CROSS-REFERENCE TO RELATED APPLICATIONS

This Application is a national stage filing under 35 U.S.C. § 371 of International Application No. PCT/US2018/067454, filed on Dec. 24, 2018, which claims the benefit of U.S. Provisional Application No. 62/610,486, filed on Dec. 26, 2017, the contents of which are incorporated herein by reference in their entireties.

STATEMENT REGARDING FEDERALLY SPONSORED RESEARCH

This invention was made with government support under grant number 1U19AI109680 awarded by the National Institutes of Health (NIH). The government has certain rights in the invention.

BACKGROUND

Arthropod borne viruses have developed a complex life cycle adapted to alternate between insect and vertebrate hosts. These arthropod-borne viruses belong mainly to the families Togaviridae, Flaviviridae, and Bunyaviridae. Flavivirus is a genus of the family Flaviviridae. This genus includes such viral infections as West Nile virus, dengue virus (DENV), Tick-borne Encephalitis virus, yellow fever virus, and zika virus (ZIKV) that may cause encephalitis. Alphavirus is a genus of the family Togaviridae. This genus includes such viral infections as chikungunya virus (CHIKV), Venezuelan Equine Encephalitis virus (VEEZ), and Eastern Equine Encephalitis virus.

Zika virus (ZIKV) is a single stranded RNA virus transmitted to humans primarily via *Aedes aegypti* mosquitos and other mosquitos of the *Stegomyia* subgenus. ZIKV can also be transmitted through sexual intercourse, a blood transfusion, or from a pregnant woman to her fetus. Infection during pregnancy can result in microcephaly and other severe fetal brain defects. Additional problems detected among fetuses and infants infected with ZIKV before birth include as defects of the eye, hearing deficits, and impaired growth. Increased reports of Guillain-Barre syndrome have also been observed in areas affected by Zika. Until recently, only sporadic human ZIKV infections had been reported. Since 2007, ZIKV has expanded from Asia and Africa to include both North and South America.

DENV is a mosquito-borne virus estimated to cause 50-100 million infections each year. DENV infections can result in serious diseases including dengue fever, dengue hemorrhagic fever, and dengue shock syndrome, and may even result in death. This virus is considered by the World Health Organization to be the most important mosquito-borne viral disease worldwide.

Originally isolated in Tanzania, sporadic outbreaks of CHIKV have continued to plague Asia and Africa. In 2007, the first outbreak in Europe was documented with over 200 confirmed cases. To date, CHIKV has been identified in over 40 countries including the United States of America. The symptoms of CHIKV, which include fever, rash, and severe joint pain, are commonly indistinguishable from ZIKV and DENV. While most patients usually recover after days to weeks, some may develop chronic arthritis. Additionally, death related to Chikungunya infection has been reported in older patients or patients with weakened immune systems.

Currently, there are no approved treatments for ZIKV, DENV, VEEV, or CHIKV. Despite the widespread distribution and severity of the effects of these viral infections, a treatment for ZIKV, DENV, VEEV, and CHIKV has remained elusive. Thus, there remains a need for antiviral agents capable of targeting these viruses and methods of making and using same.

SUMMARY

In accordance with the purpose(s) of the invention, as embodied and broadly described herein, the invention, in one aspect, relates to compositions and methods for use in the prevention and treatment of viral infections such as, for example, chikungunya, Venezuelan equine encephalitis, dengue, influenza, and zika.

Disclosed are compounds having a structure represented by a formula:

wherein each of m and n is independently selected from 0 and 1; wherein Q is selected from CH and N; wherein Z is selected from NH and $CH_2$; wherein $R^1$ is selected from hydrogen, —OH, C1-C4 alkyl, C1-C4 haloalkoxy, and C1-C4 alkoxy; wherein $R^2$ is hydrogen; and wherein $R^3$ is C2-C5 heteroaryl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)$Ar^1$, and $Ar^1$; wherein $Ar^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein $R^3$ is a structure represented by a formula:

wherein each of $R^{4a}$, $R^{4b}$, $R^{4c}$, and $R^{4d}$ is independently selected from hydrogen, halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and $Ar^2$; wherein $Ar^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein $R^5$ is selected from hydrogen, halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, —(C1-

C4 alkyl)CO$_2$H, and Ar$^3$; and wherein Ar$^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of R$^2$ and R$^3$ are covalently bonded together and, together with the intermediate atoms, comprise a 3- to 6-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and R$^1$ is hydrogen, then R$^3$ is not pyridinyl, provided that when n is 1, then R$^5$ is not hydrogen, or provided that when R$^5$ is hydrogen, then R$^1$ is not hydrogen, or a pharmaceutically acceptable salt thereof.

Also disclosed are compounds having a structure represented by a formula:

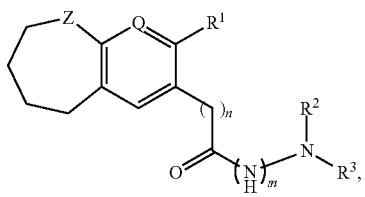

wherein each of m and n is independently selected from 0 and 1; wherein Q is selected from CH and N; wherein Z is selected from NH and CH$_2$; wherein R$^1$ is selected from hydrogen, —OH, C1-C4 alkyl, C1-C4 haloalkoxy, and C1-C4 alkoxy; wherein R$^2$ is hydrogen; and wherein R$^3$ is C2-C5 heteroaryl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar$^1$, and Ar$^1$; wherein Ar$^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein R$^3$ is a structure represented by a formula:

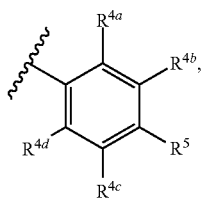

wherein each of R$^{4a}$, R$^{4b}$, R$^{4c}$, and R$^{4d}$ is independently selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar$^2$; wherein Ar$^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein R$^5$ is selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar$^3$; and wherein Ar$^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of R$^2$ and R$^3$ are covalently bonded together and, together with the intermediate atoms, comprise a 3- to 6-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and R$^1$ is hydrogen, then R$^3$ is not pyridinyl, provided that when n is 1, then R$^5$ is not hydrogen, or provided that when R$^5$ is hydrogen, then R$^1$ is not hydrogen, or a pharmaceutically acceptable salt thereof.

Also disclosed are pharmaceutical compositions comprising a therapeutically effective amount of at least one disclosed compound and a pharmaceutically acceptable carrier.

Also disclosed are methods for the treatment of a viral infection in a subject having the viral infection, the method comprising the step of administering to the subject a therapeutically effective amount of at least one disclosed compound.

Also disclosed are kits comprising at least one disclosed compound and one or more of: (a) at least one antiviral agent; (b) a instructions for administering the at least one compound in connection with treating a viral infection; (c) instructions for administering the at least one compound in connection with reducing the risk of viral infection; and (d) instructions for treating a viral infection.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated 10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group.

The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-C1-4$ straight or branched alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R*_2))_{2-3}-$, or $-S(C(R*_2))_{2-3}S-$, wherein each independent occurrence of R* is selected from hydrogen, C1-6 aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR*_2)_{2-3}O-$, wherein each independent occurrence of R* is selected from hydrogen, C1-6 aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet 2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet 2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

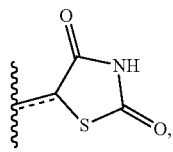

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

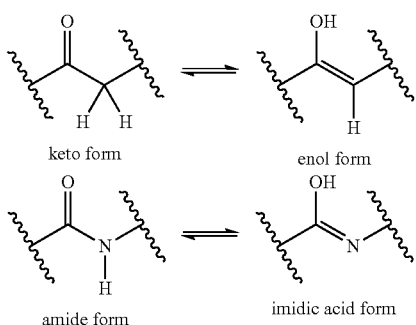

keto form / enol form amide form / imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

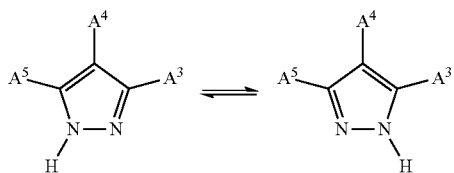

Unless stated to the contrary, the invention includes all such possible tautomers.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

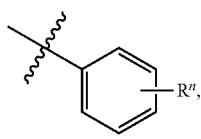

which is understood to be equivalent to a formula:

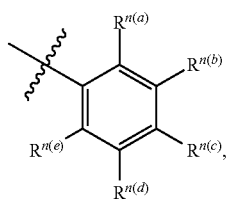

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating disorders associated with a viral infection, in particular, chikungunya, Venezuelan equine encephalitis, dengue, influenza, and zika.

In one aspect, the disclosed compounds exhibit antiviral activity.

In one aspect, the compounds of the invention are useful in inhibiting viral activity in a mammal. In a further aspect, the compounds of the invention are useful in inhibiting viral activity in at least one cell.

In one aspect, the compounds of the invention are useful in the treatment of viral infections, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

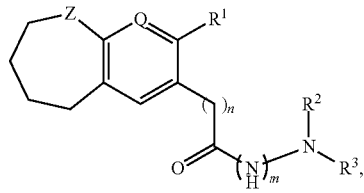

wherein each of m and n is independently selected from 0 and 1; wherein Q is selected from CH and N; wherein Z is selected from NH and $CH_2$; wherein $R^1$ is selected from hydrogen, —OH, C1-C4 alkyl, C1-C4 haloalkoxy, and C1-C4 alkoxy; wherein $R^2$ is hydrogen; and wherein $R^3$ is C2-C5 heteroaryl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4) (C1-C4) dialkylamino, (C1-C4 alkyl)$Ar^1$, and $Ar^1$; wherein $Ar^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein $R^3$ is a structure represented by a formula:

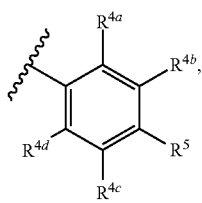

wherein each of $R^{4a}$, $R^{4b}$, $R^{4c}$, and $R^{4d}$ is independently selected from hydrogen, halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4) (C1-C4) dialkylamino, and $Ar^2$; wherein $Ar^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein $R^5$ is selected from hydrogen, halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, —(C1-C4 alkyl)$CO_2H$, and $Ar^3$; and wherein $Ar^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of $R^2$ and $R^3$ are covalently bonded together and, together with the intermediate atoms, comprise a 3- to 6-membered heterocycloalkyl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and $R^1$ is hydrogen, then $R^3$ is not pyridinyl, provided that when n is 1, then $R^5$ is not hydrogen, or provided that when $R^5$ is hydrogen, then $R^1$ is not hydrogen, or a pharmaceutically acceptable salt thereof.

In one aspect, disclosed are compounds having a structure represented by a formula:

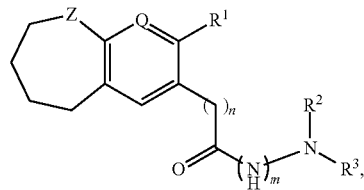

wherein each of m and n is independently selected from 0 and 1; wherein Q is selected from CH and N; wherein Z is selected from NH and $CH_2$; wherein $R^1$ is selected from hydrogen, —OH, C1-C4 alkyl, C1-C4 haloalkoxy, and C1-C4 alkoxy; wherein $R^2$ is hydrogen; and wherein $R^3$ is C2-C5 heteroaryl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4) (C1-C4) dialkylamino, (C1-C4 alkyl)$Ar^1$, and $Ar^1$; wherein $Ar^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein $R^3$ is a structure represented by a formula:

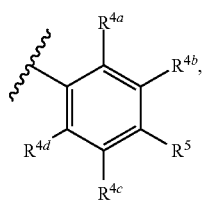

wherein each of $R^{4a}$, $R^{4b}$, $R^{4c}$, and $R^{4d}$ is independently selected from hydrogen, halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar²; wherein Ar², when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein R⁵ is selected from hydrogen, halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar³; and wherein Ar³, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of R² and R³ are covalently bonded together and, together with the intermediate atoms, comprise a 3- to 6-membered heterocycloalkyl substituted with 0, 1, 2, or 3 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and R¹ is hydrogen, then R³ is not pyridinyl, provided that when n is 1, then R⁵ is not hydrogen, or provided that when R⁵ is hydrogen, then R¹ is not hydrogen, or a pharmaceutically acceptable salt thereof.

In a further aspect, the compound has a structure represented by a formula:

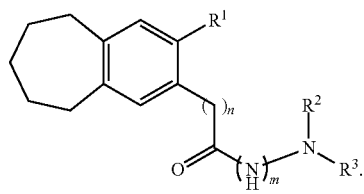

In a further aspect the compound has a structure represented by a formula:

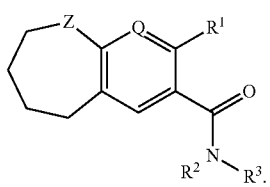

In a further aspect, the compound has a structure represented by a formula selected from:

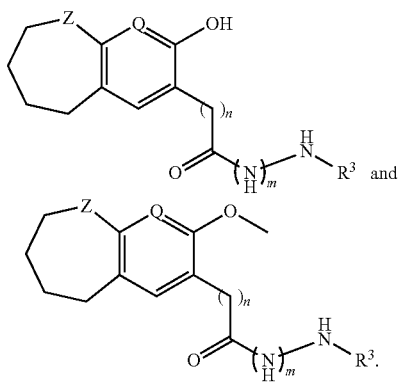

In a further aspect, the compound has a structure represented by a formula:

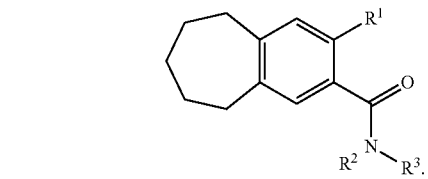

In a further aspect, the compound has a structure represented by a formula selected from:

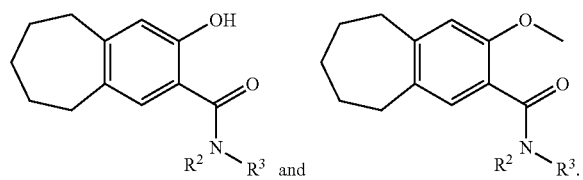

In a further aspect, the compound has a structure represented by a formula:

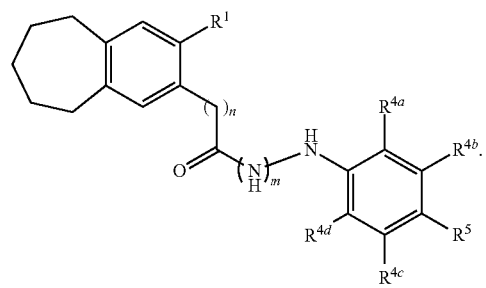

In a further aspect, the compound has a structure represented by a formula:

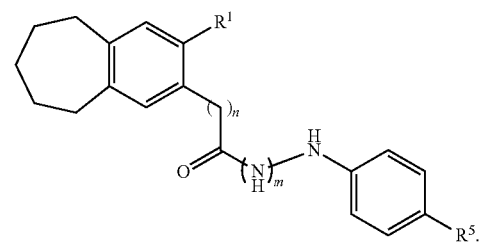

In a further aspect, the compound has a structure represented by a formula:

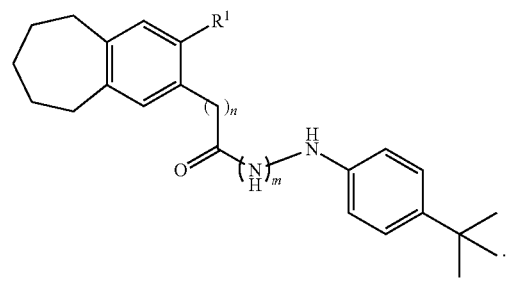

In a further aspect, the compound has a structure represented by a formula:

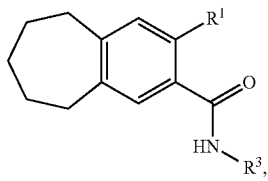

wherein R¹ is selected from hydrogen, —OH, C1-C4 alkyl, and C1-C4 alkoxy; and wherein R³ is heteroaryl substituted with 0, 1, 2, or 3 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹.

In a further aspect, the compound has a structure represented by a formula:

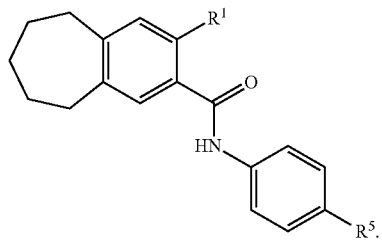

In a further aspect, the compound is selected from:

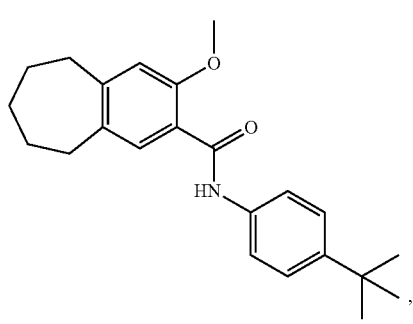

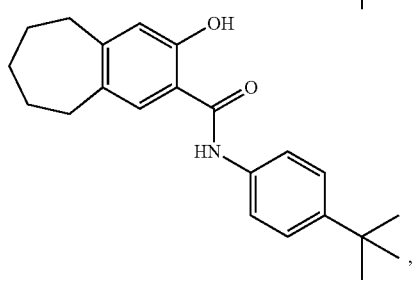

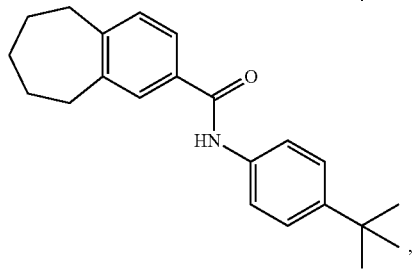

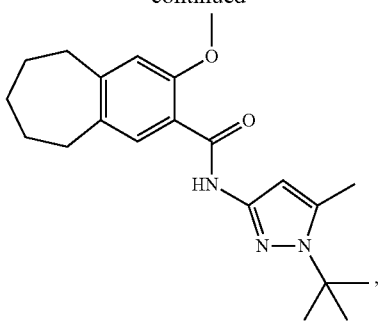

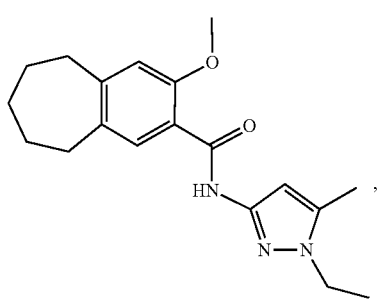

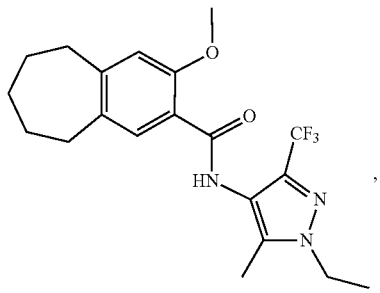

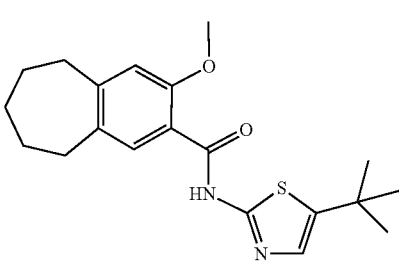

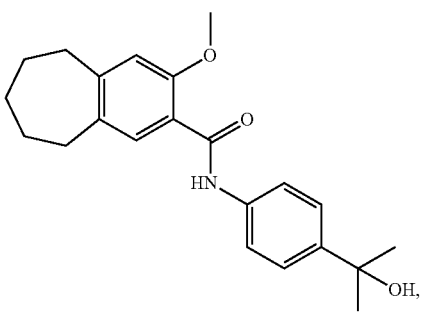

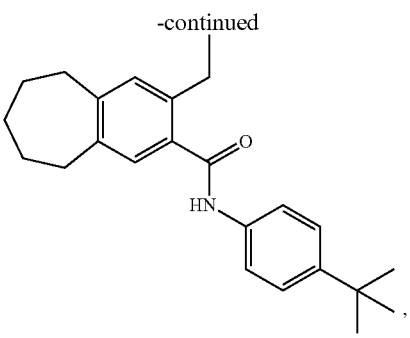
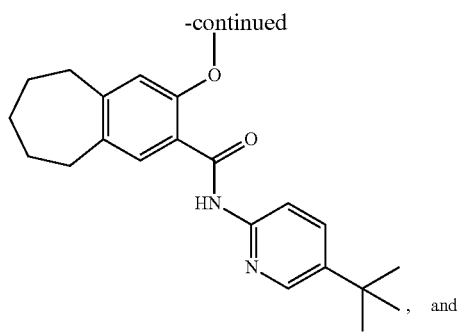, and
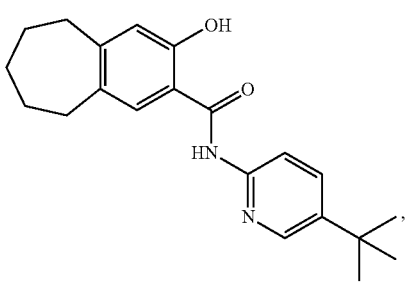
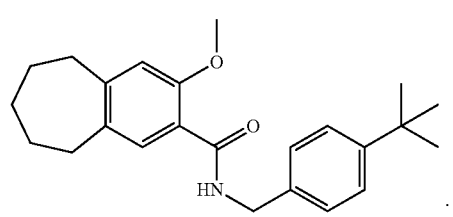.
In a further aspect, the compound is selected from:
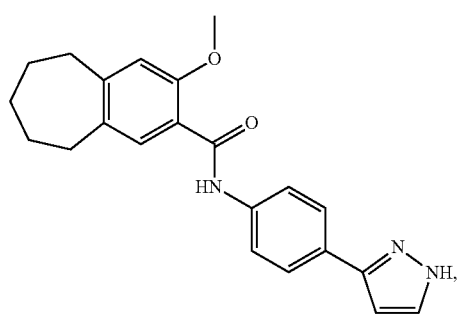
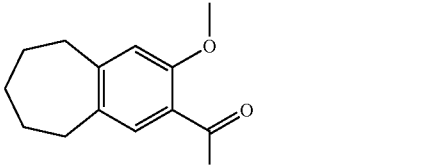
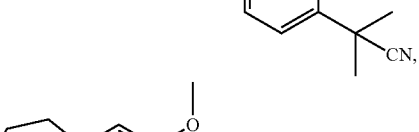
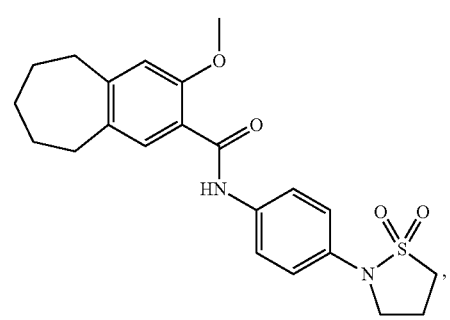
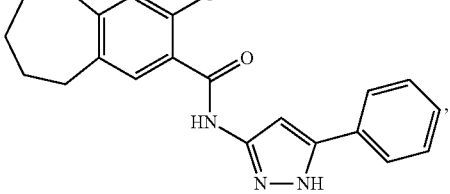
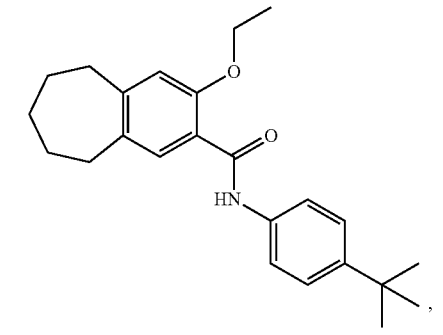
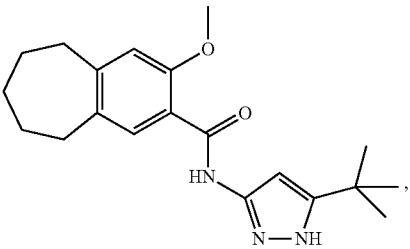

33
-continued
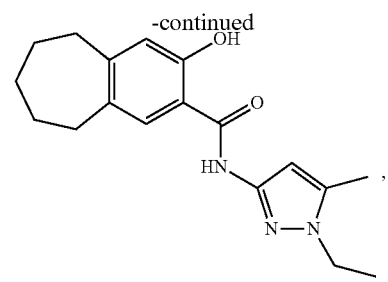
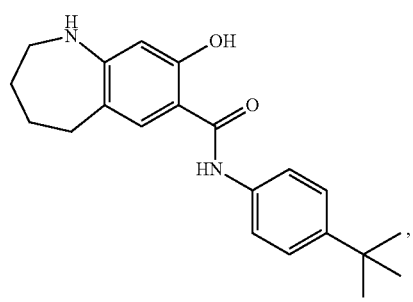
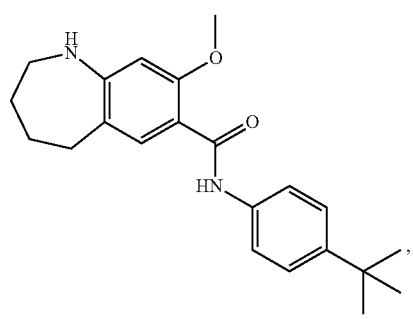
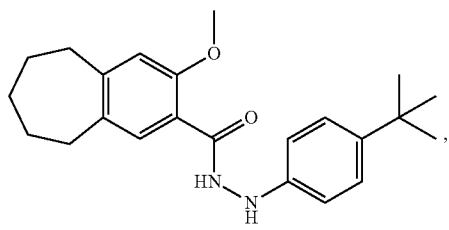
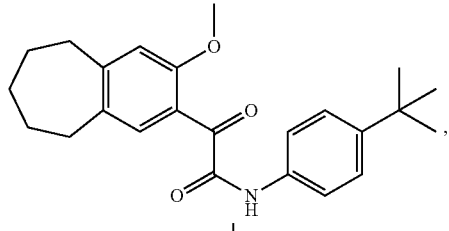
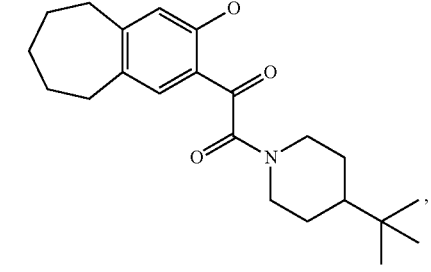
34
-continued
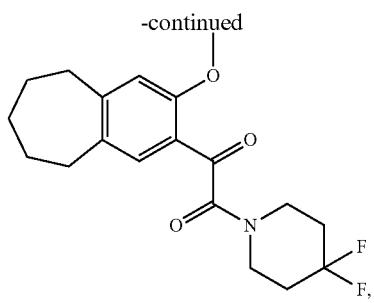
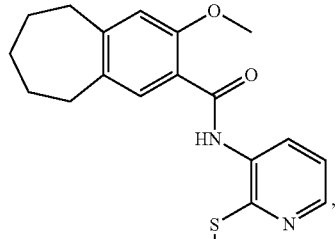
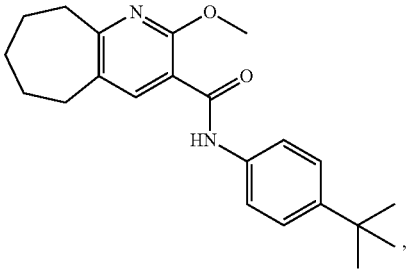
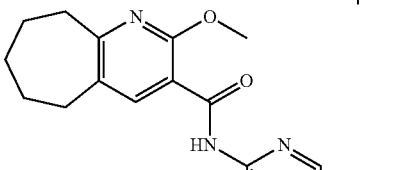
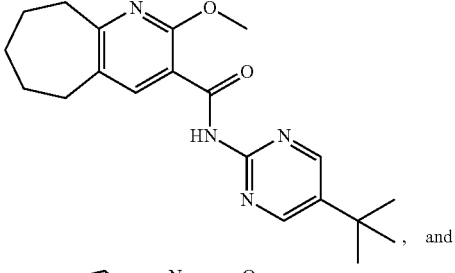
, and
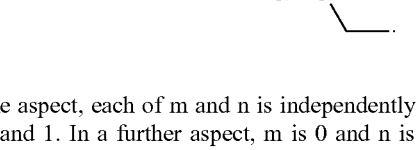
In one aspect, each of m and n is independently selected from 0 and 1. In a further aspect, m is 0 and n is selected from 0 and 1. In a still further aspect, m is 1 and n is selected from 0 and 1. In yet a further aspect, n is 0 and m is selected from 0 and 1. In an even further aspect, n is 1 and m is selected from 0 and 1. In a still further aspect, m is 0 and n is 1. In yet a further aspect, m is 1 and n is 0. In an even further aspect, each of m and n is 0. In a still further aspect, each of m and n is 1.

In a further aspect, m is 0. In a still further aspect, m is 1.
In a further aspect, n is 0. In a still further aspect, n is 1. In yet a further aspect, n is 0 and $R^5$ is not hydrogen.

a. Q Groups

In one aspect, Q is selected from CH and N. In a further aspect, Q is CH. In a still further aspect, Q is N.

b. Z Groups

In one aspect, Z is selected from NH and $CH_2$. In a further aspect, Z is NH. In a still further aspect, Z is $CH_2$.

c. $R^1$ Groups

In one aspect, $R^1$ is selected from hydrogen, —OH, C1-C4 alkyl, C1-C4 haloalkoxy, and C1-C4 alkoxy. In a still further aspect, R is —OH. In yet a further aspect, R is hydrogen.

In a further aspect, R is selected from hydrogen, —OH, methyl, ethyl, n-propyl, i-propyl, —$OCHF_2$, —$OCH_2CHF_2$, —$OCH_2CH_2CHF_2$, and —$OCH(CH_3)CHF_2$, —$OCH_3$, —$OCH_2CH_3$, —$OCH_2CH_2CH_3$, and —$OCH(CH_3)CH_3$. In a still further aspect, $R^1$ is selected from hydrogen, —OH, methyl, ethyl, —$OCHF_2$, —$OCH_2CHF_2$, —$OCH_3$, and —$OCH_2CH_3$. In yet a further aspect, $R^1$ is selected from hydrogen, —OH, —$OCHF_2$, methyl, and —$OCH_3$.

In a further aspect, R is selected from hydrogen, —OH, methyl, ethyl, n-propyl, i-propyl, —$OCH_3$, —$OCH_2CH_3$, —$OCH_2CH_2CH_3$, and —$OCH(CH_3)CH_3$. In a still further aspect, $R^1$ is selected from hydrogen, —OH, methyl, ethyl, —$OCH_3$, and —$OCH_2CH_3$. In yet a further aspect, $R^1$ is selected from hydrogen, —OH, methyl, and —$OCH_3$.

In a further aspect, $R^1$ is selected from hydrogen, C1-C4 alkyl, and C1-C4 alkoxy. In a still further aspect, R is selected from hydrogen, methyl, ethyl, n-propyl, i-propyl, —$OCH_3$, —$OCH_2CH_3$, —$OCH_2CH_2CH_3$, and —$OCH(CH_3)CH_3$. In yet a further aspect, $R^1$ is selected from hydrogen, methyl, ethyl, —$OCH_3$, and —$OCH_2CH_3$. In yet a further aspect, $R^1$ is selected from hydrogen, methyl, and —$OCH_3$.

In a further aspect, $R^1$ is selected from hydrogen, —OH, C1-C4 alkyl, and C1-C4 alkoxy. In a still further aspect, R is selected from hydrogen, —OH, methyl, ethyl, n-propyl, i-propyl, —$OCH_3$, —$OCH_2CH_3$, —$OCH_2CH_2CH_3$, and —$OCH(CH_3)CH_3$. In yet a further aspect, $R^1$ is selected from hydrogen, —OH, methyl, ethyl, —$OCH_3$, and —$OCH_2CH_3$. In yet a further aspect, $R^1$ is selected from hydrogen, —OH, methyl, and —$OCH_3$.

In a further aspect, $R^1$ is selected from —OH and C1-C4 alkoxy. In a still further aspect, $R^1$ is selected from —OH, —$OCH_3$, —$OCH_2CH_3$, —$OCH_2CH_2CH_3$, and —$OCH(CH_3)CH_3$. In yet a further aspect, $R^1$ is selected from —OH, —$OCH_3$, and —$OCH_2CH_3$. In yet a further aspect, R is selected from —OH and —$OCH_3$.

In a further aspect, $R^1$ is C1-C4 alkoxy. In a still further aspect, R is selected from —$OCH_3$, —$OCH_2CH_3$, —$OCH_2CH_2CH_3$, and —$OCH(CH_3)CH_3$. In yet a further aspect, $R^1$ is selected from —$OCH_3$ and —$OCH_2CH_3$. In yet a further aspect, $R^1$ is —$OCH_2CH_3$. In an even further aspect, $R^1$ is —$OCH_3$.

In a further aspect, $R^1$ is C1-C4 alkyl. In a still further aspect, R is selected from methyl, ethyl, n-propyl, i-propyl, n-butyl, i-butyl, s-butyl, and t-butyl. In yet a further aspect, $R^1$ is selected from methyl, ethyl, n-propyl, and i-propyl. In an even further aspect, $R^1$ is selected from methyl and ethyl. In a still further aspect, $R^1$ is ethyl. In yet a further aspect, $R^1$ is methyl.

d. $R^2$ Groups

In one aspect, $R^2$ is hydrogen or each of $R^2$ and $R^3$ are covalently bonded together and, together with the intermediate atoms, comprise a 3- to 6-membered heterocycloalkyl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino.

In a further aspect, $R^2$ is hydrogen.

In a further aspect, each of $R^2$ and $R^3$ are covalently bonded together and, together with the intermediate atoms, comprise a 3- to 6-membered heterocycloalkyl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 3- to 6-membered heterocycloalkyl substituted with 0, 1, or 2 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In yet a further aspect, each of $R^2$ and $R^3$ are covalently bonded together and, together with the intermediate atoms, comprise a 3- to 6-membered heterocycloalkyl substituted with 0 or 1 group selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In an even further aspect, each of $R^2$ and $R^3$ are covalently bonded together and, together with the intermediate atoms, comprise a 3- to 6-membered heterocycloalkyl monosubstituted with a group selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 3- to 6-membered heterocycloalkyl monosubstituted with a tert-butyl group. In yet a further aspect, each of $R^2$ and $R^3$ are covalently bonded together and, together with the intermediate atoms, comprise an unsubstituted 3- to 6-membered heterocycloalkyl.

In a further aspect, each of $R^2$ and $R^3$ are covalently bonded together and, together with the intermediate atoms, comprise a 3-membered heterocycloalkyl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 3-membered heterocycloalkyl substituted with 0, 1, or 2 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In yet a further aspect, each of $R^2$ and $R^3$ are covalently bonded together and, together with the intermediate atoms, comprise a 3-membered heterocycloalkyl substituted with 0 or 1 group selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In an even further aspect, each of $R^2$ and $R^3$ are covalently bonded together and, together with the intermediate atoms, comprise a 3-membered heterocycloalkyl monosubstituted with a group selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 3-membered heterocycloalkyl monosubstituted with a tert-butyl group. In yet a further aspect, each of $R^2$ and $R^3$ are covalently bonded together and, together with the intermediate atoms, comprise an unsubstituted 3-membered heterocycloalkyl.

In a further aspect, each of $R^2$ and $R^3$ are covalently bonded together and, together with the intermediate atoms, comprise a 4-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 4-membered heterocycloalkyl substituted with 0, 1, or 2 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In yet a further aspect, each of $R^2$ and $R^3$ are covalently bonded together and, together with the intermediate atoms, comprise a 4-membered heterocycloalkyl substituted with 0 or 1 group selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In an even further aspect, each of $R^2$ and $R^3$ are covalently bonded together and, together with the intermediate atoms, comprise a 4-membered heterocycloalkyl monosubstituted with a group selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 4-membered heterocycloalkyl monosubstituted with a tert-butyl group. In yet a further aspect, each of $R^2$ and $R^3$ are covalently bonded together and, together with the intermediate atoms, comprise an unsubstituted 4-membered heterocycloalkyl.

In a further aspect, each of $R^2$ and $R^3$ are covalently bonded together and, together with the intermediate atoms, comprise a 5-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 5-membered heterocycloalkyl substituted with 0, 1, or 2 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In yet a further aspect, each of $R^2$ and $R^3$ are covalently bonded together and, together with the intermediate atoms, comprise a 5-membered heterocycloalkyl substituted with 0 or 1 group selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In an even further aspect, each of $R^2$ and $R^3$ are covalently bonded together and, together with the intermediate atoms, comprise a 5-membered heterocycloalkyl monosubstituted with a group selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 5-membered heterocycloalkyl monosubstituted with a tert-butyl group. In yet a further aspect, each of $R^2$ and $R^3$ are covalently bonded together and, together with the intermediate atoms, comprise an unsubstituted 5-membered heterocycloalkyl.

In a further aspect, each of $R^2$ and $R^3$ are covalently bonded together and, together with the intermediate atoms, comprise a 6-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 6-membered heterocycloalkyl substituted with 0, 1, or 2 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In yet a further aspect, each of $R^2$ and $R^3$ are covalently bonded together and, together with the intermediate atoms, comprise a 6-membered heterocycloalkyl substituted with 0 or 1 group selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In an even further aspect, each of $R^2$ and $R^3$ are covalently bonded together and, together with the intermediate atoms, comprise a 6-membered heterocycloalkyl monosubstituted with a group selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino. In a still further aspect, each of $R^2$ and $R^3$ are covalently bonded together and, together with the intermediate atoms, comprise a 6-membered heterocycloalkyl monosubstituted with a tert-butyl group. In yet a further aspect, each of $R^2$ and $R^3$ are covalently bonded together and, together with the intermediate atoms, comprise an unsubstituted 6-membered heterocycloalkyl.

e. $R^3$ Groups

In one aspect, $R^3$ is C2-C5 heteroaryl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar$^1$, and Ar$^1$, or $R^3$ is a structure represented by a formula:

In a further aspect, $R^3$ is C2-C5 heteroaryl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is C2-C5 heteroaryl substituted with 0, 1, or 2 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In yet a further aspect, R³ is C2-C5 heteroaryl substituted with 0 or 1 group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In an even further aspect, R³ is C2-C5 heteroaryl monosubstituted with a group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is C2-C5 heteroaryl monosubstituted with a tert-butyl group. In yet a further aspect, R³ is unsubstituted C2-C5 heteroaryl.

In a further aspect, R³ is selected from pyrazolyl, thiazolyl, and pyridinyl.

In a further aspect, R³ is pyrazolyl substituted with 0, 1, 2, or 3 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is pyrazolyl substituted with 0, 1, or 2 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and (C1-C4 alkyl)Ar¹, Ar¹. In yet a further aspect, R³ is pyrazolyl substituted with 0 or 1 group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In an even further aspect, R³ is pyrazolyl monosubstituted with a group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is pyrazolyl monosubstituted with a tert-butyl group. In yet a further aspect, R³ is unsubstituted pyrazolyl.

In a further aspect, R³ is a structure:

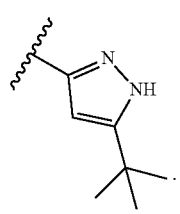 [SMILES: *c1cc(C(C)(C)C)[nH]n1 ; "."]

In a further aspect, R³ is thiazolyl substituted with 0, 1, 2, or 3 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is thiazolyl substituted with 0, 1, or 2 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In yet a further aspect, R³ is thiazolyl substituted with 0 or 1 group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In an even further aspect, R³ is thiazolyl monosubstituted with a group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is thiazolyl monosubstituted with a tert-butyl group. In yet a further aspect, R³ is unsubstituted thiazolyl.

In a further aspect, R³ is a structure:

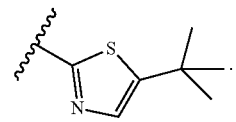 [SMILES: *c1ncc(C(C)(C)C)s1 ; "."]

In a further aspect, R³ is pyridinyl substituted with 0, 1, 2, or 3 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is pyridinyl substituted with 0, 1, or 2 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In yet a further aspect, R³ is pyridinyl substituted with 0 or 1 group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In an even further aspect, R³ is pyridinyl monosubstituted with a group selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹. In a still further aspect, R³ is pyridinyl monosubstituted with a tert-butyl group. In yet a further aspect, R³ is unsubstituted pyridinyl.

In a further aspect, R³ is a structure:

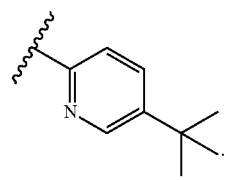 [SMILES: *c1ccc(C(C)(C)C)cn1 ; "."]

In a further aspect, R³ is a structure represented by a formula:

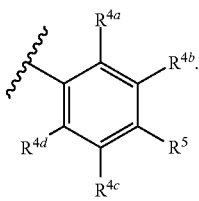

In a further aspect, R³ is a structure represented by a formula:

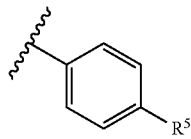

In a further aspect, R³ is a structure represented by a formula:

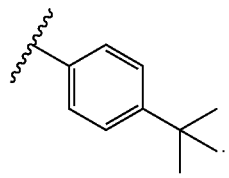

f. R⁴ᴬ, R⁴ᴮ, R⁴ᶜ, and R⁴ᴰ Groups

In one aspect, each of R⁴ᵃ, R⁴ᵇ, R⁴ᶜ, and R⁴ᵈ is independently selected from hydrogen, halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar² In a further aspect, each of R⁴ᵃ, R⁴ᵇ, R⁴ᶜ, and R⁴ᵈ is hydrogen.

In a further aspect, each of R⁴ᵃ, R⁴ᵇ, R⁴ᶜ, and R⁴ᵈ is independently selected from hydrogen, —F, —Cl, —NH₂, —CN, —OH, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —CH₂CN, —CH₂CH₂CN, —CH₂CH₂CH₂CN, —CH(CH₃)CH₂CN, —CH₂OH, —CH₂CH₂OH, —CH₂CH₂CH₂OH, —CH(CH₃)CH₂OH, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), and Ar². In a still further aspect, each of R⁴ᵃ, R⁴ᵇ, R⁴ᶜ, and R⁴ᵈ is independently selected from hydrogen, —F, —Cl, —NH₂, —CN, —OH, methyl, ethyl, —CH₂F, —CH₂Cl, —CH₂CH₂F, —CH₂CH₂Cl, —CH(CH₃)CH₂Cl, —CH₂CN, —CH₂CH₂CN, —CH₂OH, —CH₂CH₂OH, —OCH₃, —OCH₂CH₃, —NHCH₃, —NHCH₂CH₃, —N(CH₃)₂, —N(CH₂CH₃)₂, —N(CH₃)(CH₂CH₃), and Ar². In yet a further aspect, each of R⁴ᵃ, R⁴ᵇ, R⁴ᶜ, and R⁴ᵈ is independently selected from hydrogen, —F, —Cl, —NH₂, —CN, —OH, methyl, —CH₂F, —CH₂Cl, —CH₂CN, —CH₂OH, —OCH₃, —NHCH₃, —N(CH₃)₂, and Ar².

In a further aspect, each of R⁴ᵃ, R⁴ᵇ, R⁴ᶜ, and R⁴ᵈ is independently selected from hydrogen, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar². In a still further aspect, each of R⁴ᵃ, R⁴ᵇ, R⁴ᶜ, and R⁴ᵈ is independently selected from hydrogen, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —CH₂CN, —CH₂CH₂CN, —CH₂CH₂CH₂CN, —CH(CH₃)CH₂CN, —CH₂OH, —CH₂CH₂OH, —CH₂CH₂CH₂OH, —CH(CH₃)CH₂OH, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), and Ar². In yet a further aspect, each of R⁴ᵃ, R⁴ᵇ, R⁴ᶜ, and R⁴ᵈ is independently selected from hydrogen, methyl, ethyl, —CH₂F, —CH₂Cl, —CH₂CH₂F, —CH₂CH₂Cl, —CH₂CN, —CH₂CH₂CN, —CH₂OH, —CH₂CH₂OH, —OCH₃, —OCH₂CH₃, —NHCH₃, —NHCH₂CH₃, —N(CH₃)₂, —N(CH₂CH₃)₂, —N(CH₃)(CH₂CH₃), and Ar². In an even further aspect, each of R⁴ᵃ, R⁴ᵇ, R⁴ᶜ, and R⁴ᵈ is independently selected from hydrogen, methyl, —CH₂F, —CH₂Cl, —CH₂CN, —CH₂OH, —OCH₃, —NHCH₃, —N(CH₃)₂, and Ar².

In a further aspect, each of R⁴ᵃ, R⁴ᵇ, R⁴ᶜ, and R⁴ᵈ is independently selected from hydrogen, —F, —Cl, —NH₂, —CN, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar². In a still further aspect, each of R⁴ᵃ, R⁴ᵇ, R⁴ᶜ, and R⁴ᵈ is independently selected from hydrogen, —F, —Cl, —NH₂, —CN, —OH, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —CH₂CN, —CH₂CH₂CN, —CH₂CH₂CH₂CN, —CH(CH₃)CH₂CN, —CH₂OH, —CH₂CH₂OH, —CH₂CH₂CH₂OH, —CH(CH₃)CH₂OH, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₃)(CH₂CH₃), and Ar². In yet a further aspect, each of R⁴ᵃ, R⁴ᵇ, R⁴ᶜ, and R⁴ᵈ is independently selected from hydrogen, —F, —Cl, —NH₂, —CN, —OH, methyl, ethyl, —CH₂F, —CH₂Cl, —CH₂CH₂F, —CH₂CH₂Cl, —CH(CH₃)CH₂Cl, —CH₂CN, —CH₂CH₂CN, —CH₂OH, —CH₂CH₂OH, —OCH₃, —OCH₂CH₃, —NHCH₃, —NHCH₂CH₃, —N(CH₃)₂, —N(CH₂CH₃)₂, —N(CH₃)(CH₂CH₃), and Ar². In yet a further aspect, each of R⁴ᵃ, R⁴ᵇ, R⁴ᶜ, and R⁴ᵈ is independently selected from hydrogen, —F, —Cl, —NH₂, —CN, —OH, methyl, —CH₂F, —CH₂Cl, —CH₂CN, —CH₂OH, —OCH₃, —NHCH₃, —N(CH₃)₂, and Ar².

In a further aspect, each of R⁴ᵃ, R⁴ᵇ, R⁴ᶜ, and R⁴ᵈ is independently selected from hydrogen, —F, —Cl, —NH₂, —CN, —OH, C1-C4 alkyl, C1-C4 alkoxy, and Ar². In a still further aspect, each of R⁴ᵃ, R⁴ᵇ, R⁴ᶜ, and R⁴ᵈ is independently selected from hydrogen, —F, —Cl, —NH₂, —CN, —OH, methyl, ethyl, n-propyl, i-propyl, —OCH₃, —OCH₂CH₃, —OCH₂CH₂CH₃, —OCH(CH₃)CH₃, and Ar². In a still further aspect, each of R⁴ᵃ, R⁴ᵇ, R⁴ᶜ, and R⁴ᵈ is independently selected from hydrogen, —F, —Cl, —NH₂, —CN, —OH, methyl, ethyl, —OCH₃, —OCH₂CH₃, and Ar². In yet a further aspect, each of R⁴ᵃ, R⁴ᵇ, R⁴ᶜ, and R⁴ᵈ is independently selected from hydrogen, —F, —Cl, —NH₂, —CN, —OH, methyl, —OCH₃, and Ar².

In a further aspect, each of R⁴ᵃ, R⁴ᵇ, R⁴ᶜ, and R⁴ᵈ is independently selected from hydrogen, C1-C4 alkyl, C1-C4 haloalkyl, and C1-C4 alkoxy. In a still further aspect, each of R⁴ᵃ, R⁴ᵇ, R⁴ᶜ, and R⁴ᵈ is independently selected from hydrogen, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, and —OCH(CH₃)CH₃. In yet a further aspect, each of R⁴ᵃ, R⁴ᵇ, R⁴ᶜ, and R⁴ᵈ is independently selected from hydrogen, methyl, ethyl, —CH₂F, —CH₂Cl, —CH₂CH₂F, —CH₂CH₂Cl, —OCH₃, and —OCH₂CH₃. In yet a further aspect, each of R⁴ᵃ, R⁴ᵇ, R⁴ᶜ, and R⁴ᵈ is independently selected from hydrogen, methyl, —CH₂F, —CH₂Cl, and —OCH₃.

In a further aspect, each of $R^{4a}$, $R^{4b}$, $R^{4c}$, and $R^{4d}$ is independently selected from hydrogen and $Ar^2$.

In a further aspect, each of $R^{4a}$, $R^{4b}$, $R^{4c}$, and $R^{4d}$ is independently selected from hydrogen and C1-C4 haloalkyl. In a still further aspect, each of $R^{4a}$, $R^{4b}$, $R^{4c}$, and $R^{4d}$ is independently selected from hydrogen, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, and —CH(CH$_3$)CH$_2$Cl. In yet a further aspect, each of $R^{4a}$, $R^{4b}$, $R^{4c}$, and $R^{4d}$ is independently selected from hydrogen, —CH$_2$F, —CH$_2$Cl, —CH$_2$CH$_2$F, and —CH$_2$CH$_2$Cl. In yet a further aspect, each of $R^{4a}$, $R^{4b}$, $R^{4c}$, and $R^{4d}$ is independently selected from hydrogen, —CH$_2$F and —CH$_2$Cl.

In a further aspect, each of $R^{4a}$, $R^{4b}$, $R^{4c}$, and $R^{4d}$ is independently selected from hydrogen and C1-C4 alkyl. In a still further aspect, each of $R^{4a}$, $R^{4b}$, $R^{4c}$, and $R^{4d}$ is independently selected from hydrogen, methyl, ethyl, n-propyl, i-propyl, n-butyl, i-butyl, s-butyl, and t-butyl. In yet a further aspect, each of $R^{4a}$, $R^{4b}$, $R^{4c}$, and $R^{4d}$ is independently selected from hydrogen, methyl, ethyl, n-propyl, and i-propyl. In an even further aspect, each of $R^{4a}$, $R^{4b}$, $R^{4c}$, and $R^{4d}$ is independently selected from hydrogen, methyl and ethyl. In a still further aspect, each of $R^{4a}$, $R^{4b}$, $R^{4c}$, and $R^{4d}$ is independently selected from hydrogen and ethyl. In yet a further aspect, each of $R^{4a}$, $R^{4b}$, $R^{4c}$, and $R^{4d}$ is independently selected from hydrogen and methyl.

In a further aspect, each of $R^{4a}$, $R^{4b}$, $R^{4c}$, and $R^{4d}$ is independently selected from hydrogen, halogen, —NH$_2$, —CN, —OH, C1-C4 alkyl, C1-C4 alkoxy, C1-C4 alkylamino, and (C1-C4)(C1-C4) dialkylamino. In a further aspect, each of $R^{4a}$, $R^{4b}$, $R^{4c}$, and $R^{4d}$ is independently selected from hydrogen, —F, —Cl, —NH$_2$, —CN, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, and —N(CH$_3$)(CH$_2$CH$_3$). In a still further aspect, each of $R^{4a}$, $R^{4b}$, $R^{4c}$, and $R^{4d}$ is independently selected from hydrogen, —F, —Cl, —NH$_2$, —CN, —OH, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, and —N(CH$_3$)(CH$_2$CH$_3$). In yet a further aspect, each of $R^{4a}$, $R^{4b}$, $R^{4c}$, and $R^{4d}$ is independently selected from hydrogen, —F, —Cl, —NH$_2$, —CN, —OH, methyl, —CH$_2$F, —CH$_2$Cl, —OCH$_3$, —NHCH$_3$, and —N(CH$_3$)$_2$.

In a further aspect, each of $R^{4a}$, $R^{4b}$, $R^{4c}$, and $R^{4d}$ is independently selected from hydrogen, —F, —Cl, —NH$_2$, —CN, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), and $Ar^2$. In a still further aspect, each of $R^{4a}$, $R^{4b}$, $R^{4c}$, and $R^{4d}$ is independently selected from hydrogen, —F, —Cl, —NH$_2$, —CN, —OH, methyl, ethyl, —CH$_2$F, —CH$_2$Cl, —CH$_2$CH$_2$F, —CH$_2$CH$_2$Cl, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), and $Ar^2$. In yet a further aspect, each of $R^{4a}$, $R^{4b}$, $R^{4c}$, and $R^{4d}$ is independently selected from hydrogen, —F, —Cl, —NH$_2$, —CN, —OH, methyl, —CH$_2$F, —CH$_2$Cl, —OCH$_3$, —NHCH$_3$, —N(CH$_3$)$_2$, and $Ar^2$.

g. $R^5$ Groups

In one aspect, $R^5$ is selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, —(C1-C4 alkyl)CO$_2$H, and $Ar^3$.

In one aspect, $R^5$ is selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and $Ar^3$. In a further aspect, R is hydrogen.

In a further aspect, $R^5$ is selected from hydrogen, —F, —Cl, —NH$_2$, —CN, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), and $Ar^3$. In a still further aspect, $R^5$ is selected from hydrogen, —F, —Cl, —NH$_2$, —CN, —OH, methyl, ethyl, —CH$_2$F, —CH$_2$Cl, —CH$_2$CH$_2$F, —CH$_2$CH$_2$Cl, —CH(CH$_3$)CH$_2$Cl, —CH$_2$CN, —CH$_2$CH$_2$CN, —CH$_2$OH, —CH$_2$CH$_2$OH, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), and $Ar^3$. In yet a further aspect, $R^5$ is from hydrogen, —F, —Cl, —NH$_2$, —CN, —OH, methyl, —CH$_2$F, —CH$_2$Cl, —CH$_2$CN, —CH$_2$OH, —OCH$_3$, —NHCH$_3$, —N(CH$_3$)$_2$, and $Ar^3$.

In a further aspect, $R^5$ is selected from hydrogen, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and $Ar^3$. In a still further aspect, $R^5$ is selected from hydrogen, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), and $Ar^3$. In yet a further aspect, $R^5$ is selected from hydrogen, methyl, ethyl, —CH$_2$F, —CH$_2$Cl, —CH$_2$CH$_2$F, —CH$_2$CH$_2$Cl, —CH(CH$_3$)CH$_2$Cl, —CH$_2$CN, —CH$_2$CH$_2$CN, —CH$_2$OH, —CH$_2$CH$_2$OH, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), and $Ar^3$. In an even further aspect, $R^5$ is selected from hydrogen, methyl, —CH$_2$F, —CH$_2$Cl, —CH$_2$CN, —CH$_2$OH, —OCH$_3$, —NHCH$_3$, —N(CH$_3$)$_2$, and $Ar^3$.

In a further aspect, $R^5$ is selected from hydrogen, —F, —Cl, —NH$_2$, —CN, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and $Ar^3$. In a still further aspect, $R^5$ is selected from hydrogen, —F, —Cl, —NH$_2$, —CN, —OH, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)

CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), and Ar³. In a still further aspect, R is selected from hydrogen, —F, —Cl, —NH₂, —CN, —OH, methyl, ethyl, —CH₂F, —CH₂Cl, —CH₂CH₂F, —CH₂CH₂Cl, —CH(CH₃)CH₂Cl, —CH₂CN, —CH₂CH₂CN, —CH₂OH, —CH₂CH₂OH, —OCH₃, —OCH₂CH₃, —NHCH₃, —NHCH₂CH₃, —N(CH₃)₂, —N(CH₂CH₃)₂, —N(CH₃)(CH₂CH₃), and Ar³. In yet a further aspect, R⁵ is selected from hydrogen, —F, —Cl, —NH₂, —CN, —OH, methyl, —CH₂F, —CH₂Cl, —CH₂CN, —CH₂OH, —OCH₃, —NHCH₃, —N(CH₃)₂, and Ar³.

In a further aspect, R⁵ is selected from hydrogen, —F, —Cl, —NH₂, —CN, —OH, C1-C4 alkyl, C1-C4 alkoxy, and Ar³. In a still further aspect, R⁵ is selected from hydrogen, —F, —Cl, —NH₂, —CN, —OH, methyl, ethyl, n-propyl, i-propyl, —OCH₃, —OCH₂CH₃, —OCH₂CH₂CH₃, —OCH(CH₃)CH₃, and Ar³. In a still further aspect, R⁵ is independently selected from hydrogen, —F, —Cl, —NH₂, —CN, —OH, methyl, ethyl, —OCH₃, —OCH₂CH₃, and Ar³. In yet a further aspect, R⁵ is selected from hydrogen, —F, —Cl, —NH₂, —CN, —OH, methyl, —OCH₃, and Ar³.

In a further aspect, R⁵ is selected from hydrogen, C1-C4 alkyl, C1-C4 haloalkyl, and C1-C4 alkoxy. In a still further aspect, R⁵ is selected from hydrogen, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, and —OCH(CH₃)CH₃. In yet a further aspect, R⁵ is selected from hydrogen, methyl, ethyl, —CH₂F, —CH₂Cl, —CH₂CH₂F, —CH₂CH₂Cl, —OCH₃, and —OCH₂CH₃. In yet a further aspect, R⁵ is selected from hydrogen, methyl, —CH₂F, —CH₂Cl, and —OCH₃.

In a further aspect, R⁵ is selected from hydrogen and Ar³.

In a further aspect, R⁵ is selected from hydrogen and C1-C4 haloalkyl. In a still further aspect, R⁵ is selected from hydrogen, —CH₂F, —CH₂Cl, —CH₂CH₂F, —CH₂CH₂Cl, —CH₂CH₂CH₂F, —CH₂CH₂CH₂Cl, —CH(CH₃)CH₂F, and —CH(CH₃)CH₂Cl. In yet a further aspect, R⁵ is selected from hydrogen, —CH₂F, —CH₂Cl, —CH₂CH₂F, and —CH₂CH₂Cl. In yet a further aspect, R⁵ is selected from hydrogen, —CH₂F and —CH₂Cl.

In a further aspect, R⁵ is selected from hydrogen and C1-C4 alkyl. In a still further aspect, R⁵ is selected from hydrogen, methyl, ethyl, n-propyl, i-propyl, n-butyl, i-butyl, s-butyl, and t-butyl. In yet a further aspect, R⁵ is selected from hydrogen, methyl, ethyl, n-propyl, and i-propyl. In an even further aspect, each of R⁴ᵃ, R⁴ᵇ, R⁴ᶜ, and R⁴ᵈ is independently selected from hydrogen, methyl and ethyl. In a still further aspect, R⁵ is selected from hydrogen and ethyl. In yet a further aspect, R⁵ is selected from hydrogen and methyl.

In a further aspect, R⁵ is selected from hydrogen, halogen, —NH₂, —CN, —OH, C1-C4 alkyl, C1-C4 alkoxy, C1-C4 alkylamino, and (C1-C4)(C1-C4) dialkylamino. In a further aspect, R⁵ is selected from hydrogen, —F, —Cl, —NH₂, —CN, —OH, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, and —N(CH₃)(CH₂CH₃). In a still further aspect, R⁵ is selected from hydrogen, —F, —Cl, —NH₂, —CN, —OH, methyl, ethyl, —CH₂F, —CH₂Cl, —CH₂CH₂F, —CH₂CH₂Cl, —OCH₃, —OCH₂CH₃, —NHCH₃, —NHCH₂CH₃, —N(CH₃)₂, —N(CH₂CH₃)₂, and —N(CH₃)(CH₂CH₃). In yet a further aspect, R⁵ is selected from hydrogen, —F, —Cl, —NH₂, —CN, —OH, methyl, —CH₂F, —CH₂Cl, —OCH₃, —NHCH₃, and —N(CH₃)₂.

In a further aspect, R⁵ is selected from hydrogen, —F, —Cl, —NH₂, —CN, —OH, methyl, ethyl, n-propyl, i-propyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), and Ar³. In a still further aspect, R⁵ is selected from hydrogen, —F, —Cl, —NH₂, —CN, —OH, methyl, ethyl, —CH₂F, —CH₂Cl, —CH₂CH₂F, —CH₂CH₂Cl, —OCH₃, —OCH₂CH₃, —NHCH₃, —NHCH₂CH₃, —N(CH₃)₂, —N(CH₂CH₃)₂, —N(CH₃)(CH₂CH₃), and Ar³. In yet a further aspect, R⁵ is selected from hydrogen, —F, —Cl, —NH₂, —CN, —OH, methyl, —CH₂F, —CH₂Cl, —OCH₃, —NHCH₃, —N(CH₃)₂, and Ar³.

In a further aspect, R⁵ is not hydrogen.

h. AR¹ Groups

In one aspect, Ar¹, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl. In a further aspect, Ar¹, when present, is selected from cycloalkyl, monocyclic aryl, heterocycloalkyl, and heteroaryl, and is substituted with 0, 1, or 2 groups independently selected from halogen, C1-C4 alkyl, and C1-C4 haloalkyl. In a still further aspect, Ar¹, when present, is selected from cycloalkyl, monocyclic aryl, heterocycloalkyl, and heteroaryl, and is substituted with 0 or 1 group selected from halogen, C1-C4 alkyl, and C1-C4 haloalkyl. In yet a further aspect, Ar¹, when present, is selected from cycloalkyl, monocyclic aryl, heterocycloalkyl, and heteroaryl, and is monosubstituted with a group selected from halogen, C1-C4 alkyl, and C1-C4 haloalkyl. In an even further aspect, Ar¹, when present, is selected from cycloalkyl, monocyclic aryl, heterocycloalkyl, and heteroaryl, and is unsubstituted.

In a further aspect, Ar¹, when present, is selected from cycloalkyl and heterocycloalkyl, and is substituted with 0, 1, 2, or 3 groups independently selected from halogen, C1-C4 alkyl, and C1-C4 haloalkyl. In a still further aspect, Ar¹, when present, is selected from cycloalkyl and heterocycloalkyl, and is substituted with 0, 1, or 2 groups independently selected from halogen, C1-C4 alkyl, and C1-C4 haloalkyl. In yet a further aspect, Ar¹, when present, is selected from cycloalkyl and heterocycloalkyl, and is substituted with 0 or 1 group selected from halogen, C1-C4 alkyl, and C1-C4 haloalkyl. In an even further aspect, Ar¹, when present, is selected from cycloalkyl and heterocycloalkyl, and is monosubstituted with a group selected from halogen, C1-C4 alkyl, and C1-C4 haloalkyl. In a still further aspect, Ar¹, when present, is selected from cycloalkyl and heterocycloalkyl, and is unsubstituted.

In a further aspect, Ar¹, when present, is cycloalkyl substituted with 0, 1, 2, or 3 groups independently selected from halogen, C1-C4 alkyl, and C1-C4 haloalkyl. In a still further aspect, Ar¹, when present, is cycloalkyl substituted with 0, 1, or 2 groups independently selected from halogen, C1-C4 alkyl, and C1-C4 haloalkyl. In yet a further aspect, Ar¹, when present, is cycloalkyl substituted with 0 or 1 group selected from halogen, C1-C4 alkyl, and C1-C4 haloalkyl. In an even further aspect, Ar$^1$, when present, is cycloalkyl monosubstituted with a group selected from halogen, C1-C4 alkyl, and C1-C4 haloalkyl. In a still further aspect, Ar$^1$, when present, is unsubstituted cycloalkyl.

In a further aspect, Ar$^1$, when present, is selected from cyclopently and cyclohexyl, and is substituted with 0, 1, 2, or 3 groups independently selected from halogen, C1-C4 alkyl, and C1-C4 haloalkyl. In a still further aspect, Ar$^1$, when present, is selected from cyclopentyl and cyclohexyl, and is substituted with 0, 1, or 2 groups independently selected from halogen, C1-C4 alkyl, and C1-C4 haloalkyl. In yet a further aspect, Ar$^1$, when present, is selected from cyclopentyl and cyclohexyl, and is substituted with 0 or 1 group selected from halogen, C1-C4 alkyl, and C1-C4 haloalkyl. In an even further aspect, Ar$^1$, when present, is selected from cyclopentyl and cyclohexyl, and is monosubstituted with a group selected from halogen, C1-C4 alkyl, and C1-C4 haloalkyl. In a still further aspect, Ar$^1$, when present, is selected from cyclopentyl and cyclohexyl, and is unsubstituted.

In a further aspect, Ar$^1$, when present, is heterocycloalkyl substituted with 0, 1, 2, or 3 groups independently selected from halogen, C1-C4 alkyl, and C1-C4 haloalkyl. In a still further aspect, Ar$^1$, when present, is heterocycloalkyl substituted with 0, 1, or 2 groups independently selected from halogen, C1-C4 alkyl, and C1-C4 haloalkyl. In yet a further aspect, Ar$^1$, when present, is heterocycloalkyl substituted with 0 or 1 group selected from halogen, C1-C4 alkyl, and C1-C4 haloalkyl. In an even further aspect, Ar$^1$, when present, is heterocycloalkyl monosubstituted with a group selected from halogen, C1-C4 alkyl, and C1-C4 haloalkyl. In a still further aspect, Ar$^1$, when present, is unsubstituted heterocycloalkyl.

In a further aspect, Ar$^1$, when present, is selected from piperidinyl, pyrrolidinyl, tetrahydrofuranyl, tetrahydrothiophenyl, tetrahydropyranyl, and tetrahydrothiopyranyl, and is substituted with 0, 1, 2, or 3 groups independently selected from halogen, C1-C4 alkyl, and C1-C4 haloalkyl. In a still further aspect, Ar$^1$, when present, is selected from piperidinyl, pyrrolidinyl, tetrahydrofuranyl, tetrahydrothiophenyl, tetrahydropyranyl, and tetrahydrothiopyranyl, and is substituted with 0, 1, or 2 groups independently selected from halogen, C1-C4 alkyl, and C1-C4 haloalkyl. In yet a further aspect, Ar$^1$, when present, is selected from piperidinyl, pyrrolidinyl, tetrahydrofuranyl, tetrahydrothiophenyl, tetrahydropyranyl, and tetrahydrothiopyranyl, and is substituted with 0 or 1 group selected from halogen, C1-C4 alkyl, and C1-C4 haloalkyl. In an even further aspect, Ar$^1$, when present, is selected from piperidinyl, pyrrolidinyl, tetrahydrofuranyl, tetrahydrothiophenyl, tetrahydropyranyl, and tetrahydrothiopyranyl, and is monosubstituted with a group selected from halogen, C1-C4 alkyl, and C1-C4 haloalkyl. In a still further aspect, Ar$^1$, when present, is selected from piperidinyl, pyrrolidinyl, tetrahydrofuranyl, tetrahydrothiophenyl, tetrahydropyranyl, and tetrahydrothiopyranyl, and is unsubstituted.

In a further aspect, Ar$^1$, when present, is selected from monocyclic aryl and heteroaryl, and is substituted with 0, 1, 2, or 3 groups independently selected from halogen, C1-C4 alkyl, and C1-C4 haloalkyl. In a still further aspect, Ar$^1$, when present, is selected from monocyclic aryl and heteroaryl, and is substituted with 0, 1, or 2 groups independently selected from halogen, C1-C4 alkyl, and C1-C4 haloalkyl. In yet a further aspect, Ar$^1$, when present, is selected from monocyclic aryl and heteroaryl, and is substituted with 0 or 1 group selected from halogen, C1-C4 alkyl, and C1-C4 haloalkyl. In an even further aspect, Ar$^1$, when present, is selected from monocyclic aryl and heteroaryl, and is monosubstituted with a group selected from halogen, C1-C4 alkyl, and C1-C4 haloalkyl. In a still further aspect, Ar$^1$, when present, is selected from monocyclic aryl and heteroaryl, and is unsubstituted.

In a further aspect, Ar$^1$, when present, is monocyclic aryl substituted with 0, 1, 2, or 3 groups independently selected from halogen, C1-C4 alkyl, and C1-C4 haloalkyl. In a still further aspect, Ar$^1$, when present, is monocyclic aryl substituted with 0, 1, or 2 groups independently selected from halogen, C1-C4 alkyl, and C1-C4 haloalkyl. In yet a further aspect, Ar$^1$, when present, is monocyclic aryl substituted with 0 or 1 group selected from halogen, C1-C4 alkyl, and C1-C4 haloalkyl. In an even further aspect, Ar$^1$, when present, is monocyclic aryl monosubstituted with a group selected from halogen, C1-C4 alkyl, and C1-C4 haloalkyl. In a still further aspect, Ar$^1$, when present, is unsubstituted monocyclic aryl.

In a further aspect, Ar$^1$, when present, is heteroaryl substituted with 0, 1, 2, or 3 groups independently selected from halogen, C1-C4 alkyl, and C1-C4 haloalkyl. In a still further aspect, Ar$^1$, when present, is heteroaryl substituted with 0, 1, or 2 groups independently selected from halogen, C1-C4 alkyl, and C1-C4 haloalkyl. In yet a further aspect, Ar$^1$, when present, is heteroaryl substituted with 0 or 1 group selected from halogen, C1-C4 alkyl, and C1-C4 haloalkyl. In an even further aspect, Ar$^1$, when present, is heteroaryl monosubstituted with a group selected from halogen, C1-C4 alkyl, and C1-C4 haloalkyl. In a still further aspect, Ar$^1$, when present, is unsubstituted heteroaryl.

In a further aspect, Ar$^1$, when present, is selected from pyrazolyl, thiazolyl, and pyridinyl, and is substituted with 0, 1, 2, or 3 groups independently selected from halogen, C1-C4 alkyl, and C1-C4 haloalkyl. In a still further aspect, Ar$^1$, when present, is selected from pyrazolyl, thiazolyl, and pyridinyl, and is substituted with 0, 1, or 2 groups independently selected from halogen, C1-C4 alkyl, and C1-C4 haloalkyl. In yet a further aspect, Ar$^1$, when present, is selected from pyrazolyl, thiazolyl, and pyridinyl, and is substituted with 0 or 1 group selected from halogen, C1-C4 alkyl, and C1-C4 haloalkyl. In an even further aspect, Ar$^1$, when present, is selected from pyrazolyl, thiazolyl, and pyridinyl, and is monosubstituted with a group selected from halogen, C1-C4 alkyl, and C1-C4 haloalkyl. In a still further aspect, Ar$^1$, when present, is selected from pyrazolyl, thiazolyl, and pyridinyl, and is unsubstituted.

i. AR$^2$ Groups

In one aspect, Ar$^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl. In a further aspect, Ar$^2$, when present, is selected from cycloalkyl, monocyclic aryl, heterocycloalkyl, and heteroaryl, and is substituted with 0, 1, or 2 groups independently selected from halogen, C1-C4 alkyl, and C1-C4 haloalkyl. In a still further aspect, Ar$^2$, when present, is selected from cycloalkyl, monocyclic aryl, heterocycloalkyl, and heteroaryl, and is substituted with 0 or 1 group selected from halogen, C1-C4 alkyl, and C1-C4 haloalkyl. In yet a further aspect, Ar$^2$, when present, is selected from cycloalkyl, monocyclic aryl, heterocycloalkyl, and heteroaryl, and is monosubstituted with a group selected from halogen, C1-C4 alkyl, and C1-C4 haloalkyl. In an even further aspect, Ar$^2$, when present, is selected from cycloalkyl, monocyclic aryl, heterocycloalkyl, and heteroaryl, and is unsubstituted.

In a further aspect, Ar$^2$, when present, is selected from cycloalkyl and heterocycloalkyl, and is substituted with 0, 1, 2, or 3 groups independently selected from halogen, C1-C4 alkyl, and C1-C4 haloalkyl. In a still further aspect, $Ar^2$, when present, is selected from cycloalkyl and heterocycloalkyl, and is substituted with 0, 1, or 2 groups independently selected from halogen, C1-C4 alkyl, and C1-C4 haloalkyl. In yet a further aspect, $Ar^2$, when present, is selected from cycloalkyl and heterocycloalkyl, and is substituted with 0 or 1 group selected from halogen, C1-C4 alkyl, and C1-C4 haloalkyl. In an even further aspect, $Ar^2$, when present, is selected from cycloalkyl and heterocycloalkyl, and is monosubstituted with a group selected from halogen, C1-C4 alkyl, and C1-C4 haloalkyl. In a still further aspect, $Ar^2$, when present, is selected from cycloalkyl and heterocycloalkyl, and is unsubstituted.

In a further aspect, $Ar^2$, when present, is cycloalkyl substituted with 0, 1, 2, or 3 groups independently selected from halogen, C1-C4 alkyl, and C1-C4 haloalkyl. In a still further aspect, $Ar^2$, when present, is cycloalkyl substituted with 0, 1, or 2 groups independently selected from halogen, C1-C4 alkyl, and C1-C4 haloalkyl. In yet a further aspect, $Ar^2$, when present, is cycloalkyl substituted with 0 or 1 group selected from halogen, C1-C4 alkyl, and C1-C4 haloalkyl. In an even further aspect, $Ar^2$, when present, is cycloalkyl monosubstituted with a group selected from halogen, C1-C4 alkyl, and C1-C4 haloalkyl. In a still further aspect, $Ar^2$, when present, is unsubstituted cycloalkyl.

In a further aspect, $Ar^2$, when present, is selected from cyclopentyl and cyclohexyl, and is substituted with 0, 1, 2, or 3 groups independently selected from halogen, C1-C4 alkyl, and C1-C4 haloalkyl. In a still further aspect, $Ar^2$, when present, is selected from cyclopentyl and cyclohexyl, and is substituted with 0, 1, or 2 groups independently selected from halogen, C1-C4 alkyl, and C1-C4 haloalkyl. In yet a further aspect, $Ar^2$, when present, is selected from cyclopentyl and cyclohexyl, and is substituted with 0 or 1 group selected from halogen, C1-C4 alkyl, and C1-C4 haloalkyl. In an even further aspect, $Ar^2$, when present, is selected from cyclopentyl and cyclohexyl, and is monosubstituted with a group selected from halogen, C1-C4 alkyl, and C1-C4 haloalkyl. In a still further aspect, $Ar^2$, when present, is selected from cyclopentyl and cyclohexyl, and is unsubstituted.

In a further aspect, $Ar^2$, when present, is heterocycloalkyl substituted with 0, 1, 2, or 3 groups independently selected from halogen, C1-C4 alkyl, and C1-C4 haloalkyl. In a still further aspect, $Ar^2$, when present, is heterocycloalkyl substituted with 0, 1, or 2 groups independently selected from halogen, C1-C4 alkyl, and C1-C4 haloalkyl. In yet a further aspect, $Ar^2$, when present, is heterocycloalkyl substituted with 0 or 1 group selected from halogen, C1-C4 alkyl, and C1-C4 haloalkyl. In an even further aspect, $Ar^2$, when present, is heterocycloalkyl monosubstituted with a group selected from halogen, C1-C4 alkyl, and C1-C4 haloalkyl. In a still further aspect, $Ar^2$, when present, is unsubstituted heterocycloalkyl.

In a further aspect, $Ar^2$, when present, is selected from piperidinyl, pyrrolidinyl, tetrahydrofuranyl, tetrahydrothiophenyl, tetrahydropyranyl, and tetrahydrothiopyranyl, and is substituted with 0, 1, 2, or 3 groups independently selected from halogen, C1-C4 alkyl, and C1-C4 haloalkyl. In a still further aspect, $Ar^2$, when present, is selected from piperidinyl, pyrrolidinyl, tetrahydrofuranyl, tetrahydrothiophenyl, tetrahydropyranyl, and tetrahydrothiopyranyl, and is substituted with 0, 1, or 2 groups independently selected from halogen, C1-C4 alkyl, and C1-C4 haloalkyl. In yet a further aspect, $Ar^2$, when present, is selected from piperidinyl, pyrrolidinyl, tetrahydrofuranyl, tetrahydrothiophenyl, tetrahydropyranyl, and tetrahydrothiopyranyl, and is substituted with 0 or 1 group selected from halogen, C1-C4 alkyl, and C1-C4 haloalkyl. In an even further aspect, $Ar^2$, when present, is selected from piperidinyl, pyrrolidinyl, tetrahydrofuranyl, tetrahydrothiophenyl, tetrahydropyranyl, and tetrahydrothiopyranyl, and is monosubstituted with a group selected from halogen, C1-C4 alkyl, and C1-C4 haloalkyl. In a still further aspect, $Ar^2$, when present, is selected from piperidinyl, pyrrolidinyl, tetrahydrofuranyl, tetrahydrothiophenyl, tetrahydropyranyl, and tetrahydrothiopyranyl, and is unsubstituted.

In a further aspect, $Ar^2$, when present, is selected from monocyclic aryl and heteroaryl, and is substituted with 0, 1, 2, or 3 groups independently selected from halogen, C1-C4 alkyl, and C1-C4 haloalkyl. In a still further aspect, $Ar^2$, when present, is selected from monocyclic aryl and heteroaryl, and is substituted with 0, 1, or 2 groups independently selected from halogen, C1-C4 alkyl, and C1-C4 haloalkyl. In yet a further aspect, $Ar^2$, when present, is selected from monocyclic aryl and heteroaryl, and is substituted with 0 or 1 group selected from halogen, C1-C4 alkyl, and C1-C4 haloalkyl. In an even further aspect, $Ar^2$, when present, is selected from monocyclic aryl and heteroaryl, and is monosubstituted with a group selected from halogen, C1-C4 alkyl, and C1-C4 haloalkyl. In a still further aspect, $Ar^2$, when present, is selected from monocyclic aryl and heteroaryl, and is unsubstituted.

In a further aspect, $Ar^2$, when present, is monocyclic aryl substituted with 0, 1, 2, or 3 groups independently selected from halogen, C1-C4 alkyl, and C1-C4 haloalkyl. In a still further aspect, $Ar^2$, when present, is monocyclic aryl substituted with 0, 1, or 2 groups independently selected from halogen, C1-C4 alkyl, and C1-C4 haloalkyl. In yet a further aspect, $Ar^2$, when present, is monocyclic aryl substituted with 0 or 1 group selected from halogen, C1-C4 alkyl, and C1-C4 haloalkyl. In an even further aspect, $Ar^2$, when present, is monocyclic aryl monosubstituted with a group selected from halogen, C1-C4 alkyl, and C1-C4 haloalkyl. In a still further aspect, $Ar^2$, when present, is unsubstituted monocyclic aryl.

In a further aspect, $Ar^2$, when present, is heteroaryl substituted with 0, 1, 2, or 3 groups independently selected from halogen, C1-C4 alkyl, and C1-C4 haloalkyl. In a still further aspect, $Ar^2$, when present, is heteroaryl substituted with 0, 1, or 2 groups independently selected from halogen, C1-C4 alkyl, and C1-C4 haloalkyl. In yet a further aspect, $Ar^2$, when present, is heteroaryl substituted with 0 or 1 group selected from halogen, C1-C4 alkyl, and C1-C4 haloalkyl. In an even further aspect, $Ar^2$, when present, is heteroaryl monosubstituted with a group selected from halogen, C1-C4 alkyl, and C1-C4 haloalkyl. In a still further aspect, $Ar^2$, when present, is unsubstituted heteroaryl.

In a further aspect, $Ar^2$, when present, is selected from pyrazolyl, thiazolyl, and pyridinyl, and is substituted with 0, 1, 2, or 3 groups independently selected from halogen, C1-C4 alkyl, and C1-C4 haloalkyl. In a still further aspect, $Ar^2$, when present, is selected from pyrazolyl, thiazolyl, and pyridinyl, and is substituted with 0, 1, or 2 groups independently selected from halogen, C1-C4 alkyl, and C1-C4 haloalkyl. In yet a further aspect, $Ar^2$, when present, is selected from pyrazolyl, thiazolyl, and pyridinyl, and is substituted with 0 or 1 group selected from halogen, C1-C4 alkyl, and C1-C4 haloalkyl. In an even further aspect, $Ar^2$, when present, is selected from pyrazolyl, thiazolyl, and pyridinyl, and is monosubstituted with a group selected from halogen, C1-C4 alkyl, and C1-C4 haloalkyl. In a still further aspect, $Ar^2$, when present, is selected from pyrazolyl, thiazolyl, and pyridinyl, and is unsubstituted.

j. $AR^3$ Groups

In one aspect, $Ar^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl. In a further aspect, $Ar^3$, when present, is selected from cycloalkyl, monocyclic aryl, heterocycloalkyl, and heteroaryl, and is substituted with 0, 1, or 2 groups independently selected from halogen, C1-C4 alkyl, and C1-C4 haloalkyl. In a still further aspect, $Ar^3$, when present, is selected from cycloalkyl, monocyclic aryl, heterocycloalkyl, and heteroaryl, and is substituted with 0 or 1 group selected from halogen, C1-C4 alkyl, and C1-C4 haloalkyl. In yet a further aspect, $Ar^3$, when present, is selected from cycloalkyl, monocyclic aryl, heterocycloalkyl, and heteroaryl, and is monosubstituted with a group selected from halogen, C1-C4 alkyl, and C1-C4 haloalkyl. In an even further aspect, $Ar^3$, when present, is selected from cycloalkyl, monocyclic aryl, heterocycloalkyl, and heteroaryl, and is unsubstituted.

In a further aspect, $Ar^3$, when present, is selected from cycloalkyl and heterocycloalkyl, and is substituted with 0, 1, 2, or 3 groups independently selected from halogen, C1-C4 alkyl, and C1-C4 haloalkyl. In a still further aspect, $Ar^3$, when present, is selected from cycloalkyl and heterocycloalkyl, and is substituted with 0, 1, or 2 groups independently selected from halogen, C1-C4 alkyl, and C1-C4 haloalkyl. In yet a further aspect, $Ar^3$, when present, is selected from cycloalkyl and heterocycloalkyl, and is substituted with 0 or 1 group selected from halogen, C1-C4 alkyl, and C1-C4 haloalkyl. In an even further aspect, $Ar^3$, when present, is selected from cycloalkyl and heterocycloalkyl, and is monosubstituted with a group selected from halogen, C1-C4 alkyl, and C1-C4 haloalkyl. In a still further aspect, $Ar^3$, when present, is selected from cycloalkyl and heterocycloalkyl, and is unsubstituted.

In a further aspect, $Ar^3$, when present, is cycloalkyl substituted with 0, 1, 2, or 3 groups independently selected from halogen, C1-C4 alkyl, and C1-C4 haloalkyl. In a still further aspect, $Ar^3$, when present, is cycloalkyl substituted with 0, 1, or 2 groups independently selected from halogen, C1-C4 alkyl, and C1-C4 haloalkyl. In yet a further aspect, $Ar^3$, when present, is cycloalkyl substituted with 0 or 1 group selected from halogen, C1-C4 alkyl, and C1-C4 haloalkyl. In an even further aspect, $Ar^3$, when present, is cycloalkyl monosubstituted with a group selected from halogen, C1-C4 alkyl, and C1-C4 haloalkyl. In a still further aspect, $Ar^3$, when present, is unsubstituted cycloalkyl.

In a further aspect, $Ar^3$, when present, is selected from cyclopentyl and cyclohexyl, and is substituted with 0, 1, 2, or 3 groups independently selected from halogen, C1-C4 alkyl, and C1-C4 haloalkyl. In a still further aspect, $Ar^3$, when present, is selected from cyclopentyl and cyclohexyl, and is substituted with 0, 1, or 2 groups independently selected from halogen, C1-C4 alkyl, and C1-C4 haloalkyl. In yet a further aspect, $Ar^3$, when present, is selected from cyclopentyl and cyclohexyl, and is substituted with 0 or 1 group selected from halogen, C1-C4 alkyl, and C1-C4 haloalkyl. In an even further aspect, $Ar^3$, when present, is selected from cyclopentyl and cyclohexyl, and is monosubstituted with a group selected from halogen, C1-C4 alkyl, and C1-C4 haloalkyl. In a still further aspect, $Ar^3$, when present, is selected from cyclopentyl and cyclohexyl, and is unsubstituted.

In a further aspect, $Ar^3$, when present, is heterocycloalkyl substituted with 0, 1, 2, or 3 groups independently selected from halogen, C1-C4 alkyl, and C1-C4 haloalkyl. In a still further aspect, $Ar^3$, when present, is heterocycloalkyl substituted with 0, 1, or 2 groups independently selected from halogen, C1-C4 alkyl, and C1-C4 haloalkyl. In yet a further aspect, $Ar^3$, when present, is heterocycloalkyl substituted with 0 or 1 group selected from halogen, C1-C4 alkyl, and C1-C4 haloalkyl. In an even further aspect, $Ar^3$, when present, is heterocycloalkyl monosubstituted with a group selected from halogen, C1-C4 alkyl, and C1-C4 haloalkyl. In a still further aspect, $Ar^3$, when present, is unsubstituted heterocycloalkyl.

In a further aspect, $Ar^3$, when present, is selected from piperidinyl, pyrrolidinyl, tetrahydrofuranyl, tetrahydrothiophenyl, tetrahydropyranyl, and tetrahydrothiopyranyl, and is substituted with 0, 1, 2, or 3 groups independently selected from halogen, C1-C4 alkyl, and C1-C4 haloalkyl. In a still further aspect, $Ar^3$, when present, is selected from piperidinyl, pyrrolidinyl, tetrahydrofuranyl, tetrahydrothiophenyl, tetrahydropyranyl, and tetrahydrothiopyranyl, and is substituted with 0, 1, or 2 groups independently selected from halogen, C1-C4 alkyl, and C1-C4 haloalkyl. In yet a further aspect, $Ar^3$, when present, is selected from piperidinyl, pyrrolidinyl, tetrahydrofuranyl, tetrahydrothiophenyl, tetrahydropyranyl, and tetrahydrothiopyranyl, and is substituted with 0 or 1 group selected from halogen, C1-C4 alkyl, and C1-C4 haloalkyl. In an even further aspect, $Ar^3$, when present, is selected from piperidinyl, pyrrolidinyl, tetrahydrofuranyl, tetrahydrothiophenyl, tetrahydropyranyl, and tetrahydrothiopyranyl, and is monosubstituted with a group selected from halogen, C1-C4 alkyl, and C1-C4 haloalkyl. In a still further aspect, $Ar^3$, when present, is selected from piperidinyl, pyrrolidinyl, tetrahydrofuranyl, tetrahydrothiophenyl, tetrahydropyranyl, and tetrahydrothiopyranyl, and is unsubstituted.

In a further aspect, $Ar^3$, when present, is selected from monocyclic aryl and heteroaryl, and is substituted with 0, 1, 2, or 3 groups independently selected from halogen, C1-C4 alkyl, and C1-C4 haloalkyl. In a still further aspect, $Ar^3$, when present, is selected from monocyclic aryl and heteroaryl, and is substituted with 0, 1, or 2 groups independently selected from halogen, C1-C4 alkyl, and C1-C4 haloalkyl. In yet a further aspect, $Ar^3$, when present, is selected from monocyclic aryl and heteroaryl, and is substituted with 0 or 1 group selected from halogen, C1-C4 alkyl, and C1-C4 haloalkyl. In an even further aspect, $Ar^3$, when present, is selected from monocyclic aryl and heteroaryl, and is monosubstituted with a group selected from halogen, C1-C4 alkyl, and C1-C4 haloalkyl. In a still further aspect, $Ar^3$, when present, is selected from monocyclic aryl and heteroaryl, and is unsubstituted.

In a further aspect, $Ar^3$, when present, is monocyclic aryl substituted with 0, 1, 2, or 3 groups independently selected from halogen, C1-C4 alkyl, and C1-C4 haloalkyl. In a still further aspect, $Ar^3$, when present, is monocyclic aryl substituted with 0, 1, or 2 groups independently selected from halogen, C1-C4 alkyl, and C1-C4 haloalkyl. In yet a further aspect, $Ar^3$, when present, is monocyclic aryl substituted with 0 or 1 group selected from halogen, C1-C4 alkyl, and C1-C4 haloalkyl. In an even further aspect, $Ar^3$, when present, is monocyclic aryl monosubstituted with a group selected from halogen, C1-C4 alkyl, and C1-C4 haloalkyl. In a still further aspect, $Ar^3$, when present, is unsubstituted monocyclic aryl.

In a further aspect, $Ar^3$, when present, is heteroaryl substituted with 0, 1, 2, or 3 groups independently selected from halogen, C1-C4 alkyl, and C1-C4 haloalkyl. In a still further aspect, $Ar^3$, when present, is heteroaryl substituted with 0, 1, or 2 groups independently selected from halogen, C1-C4 alkyl, and C1-C4 haloalkyl. In yet a further aspect, Ar³, when present, is heteroaryl substituted with 0 or 1 group selected from halogen, C1-C4 alkyl, and C1-C4 haloalkyl. In an even further aspect, Ar³, when present, is heteroaryl monosubstituted with a group selected from halogen, C1-C4 alkyl, and C1-C4 haloalkyl. In a still further aspect, Ar³, when present, is unsubstituted heteroaryl.

In a further aspect, Ar³, when present, is selected from pyrazolyl, thiazolyl, and pyridinyl, and is substituted with 0, 1, 2, or 3 groups independently selected from halogen, C1-C4 alkyl, and C1-C4 haloalkyl. In a still further aspect, Ar³, when present, is selected from pyrazolyl, thiazolyl, and pyridinyl, and is substituted with 0, 1, or 2 groups independently selected from halogen, C1-C4 alkyl, and C1-C4 haloalkyl. In yet a further aspect, Ar³, when present, is selected from pyrazolyl, thiazolyl, and pyridinyl, and is substituted with 0 or 1 group selected from halogen, C1-C4 alkyl, and C1-C4 haloalkyl. In an even further aspect, Ar³, when present, is selected from pyrazolyl, thiazolyl, and pyridinyl, and is monosubstituted with a group selected from halogen, C1-C4 alkyl, and C1-C4 haloalkyl. In a still further aspect, Ar³, when present, is selected from pyrazolyl, thiazolyl, and pyridinyl, and is unsubstituted.

2. Example Compounds

In one aspect, a compound can be present as one or more of the following structures:

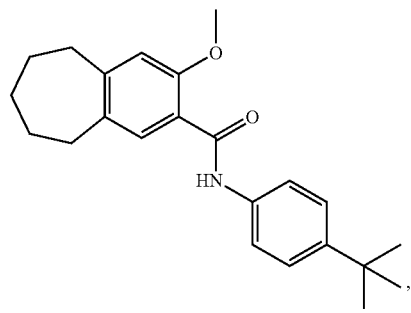

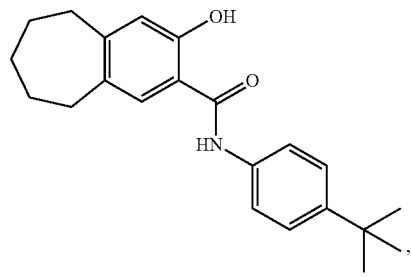

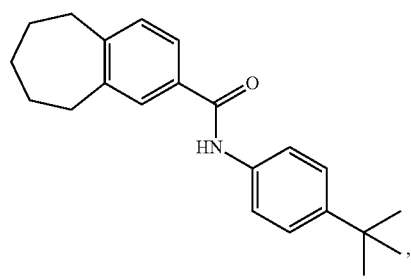

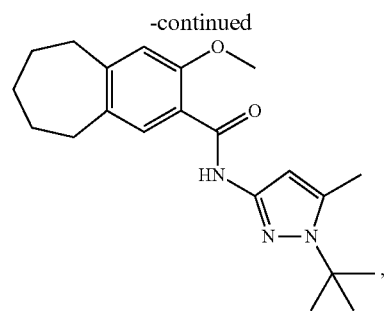

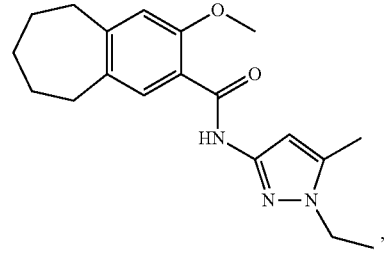

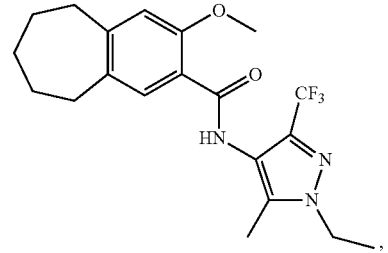

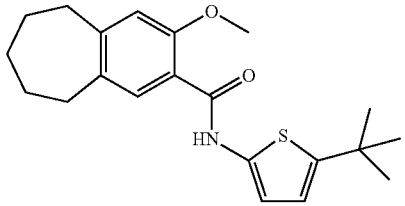

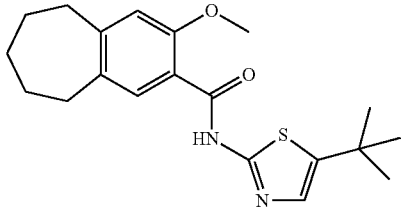

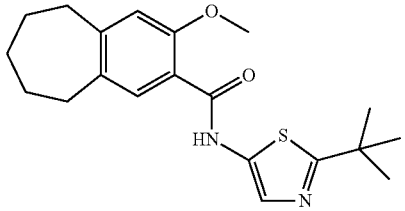

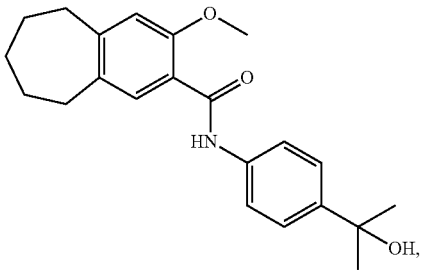

-continued
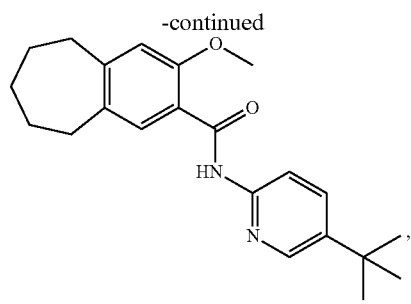
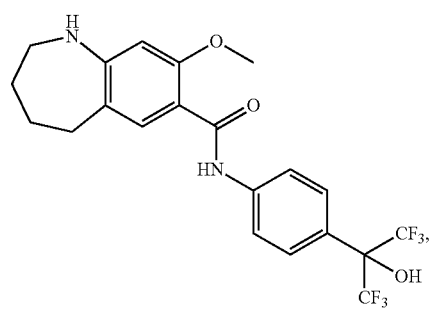
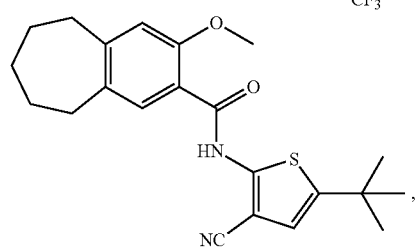
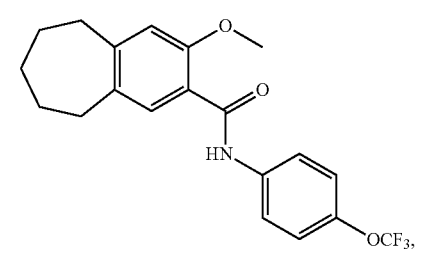
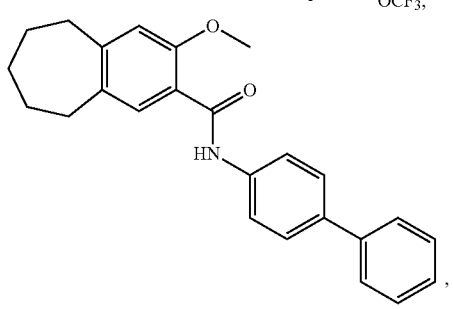
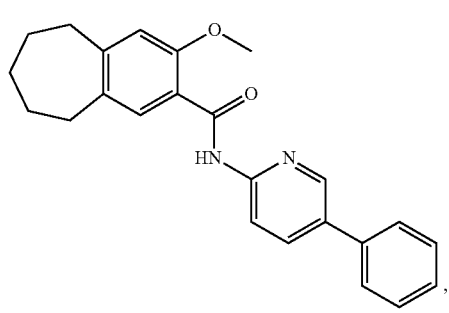
-continued
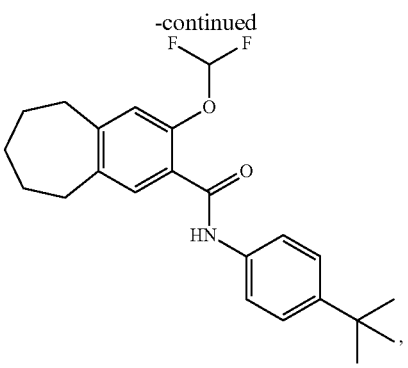
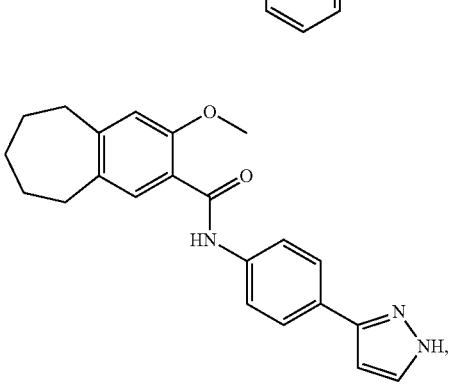
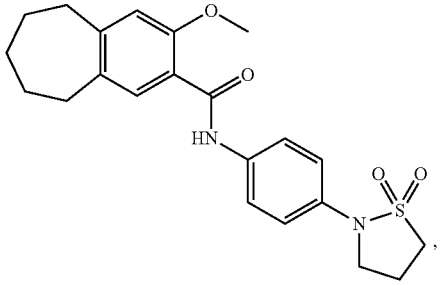
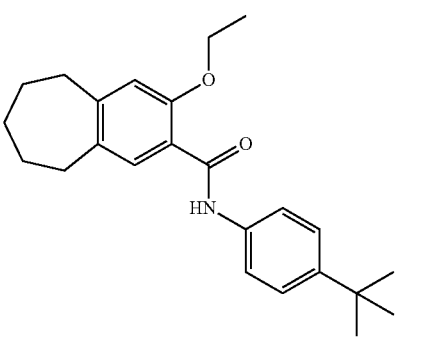

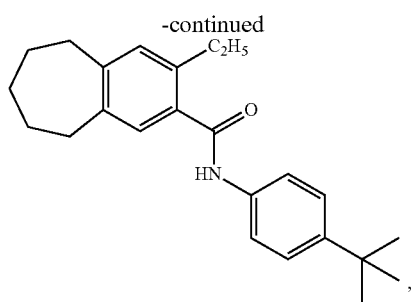
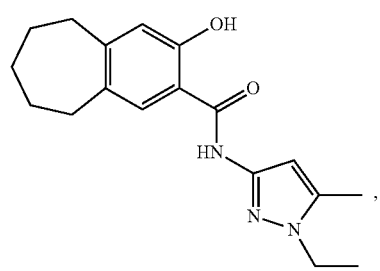
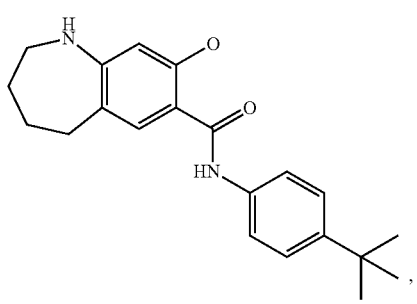
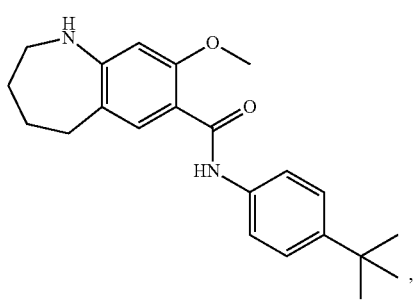
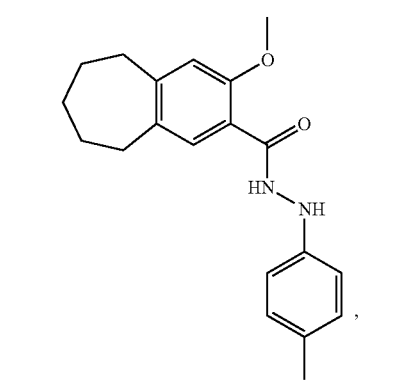
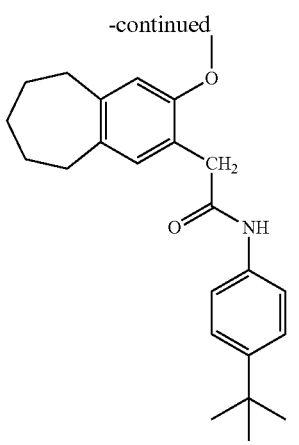
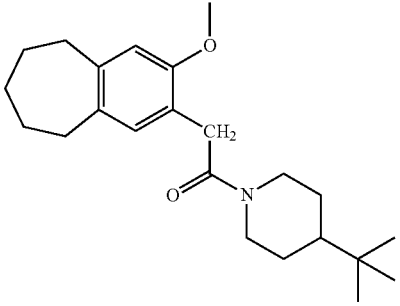
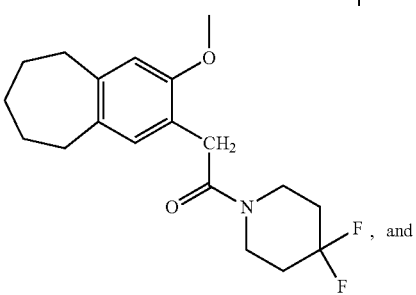
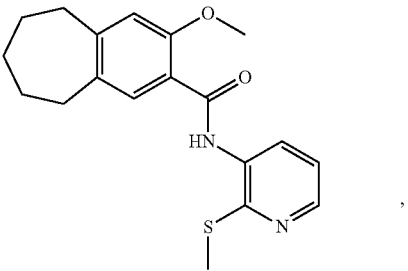
or a pharmaceutically acceptable salt thereof.
In one aspect, a compound can be present as one or more of the following structures:
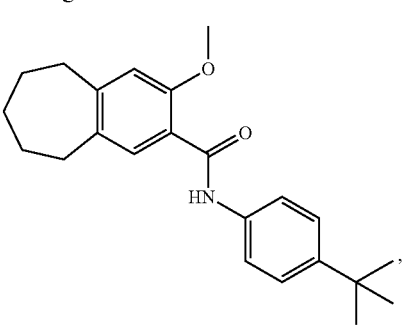

59
-continued
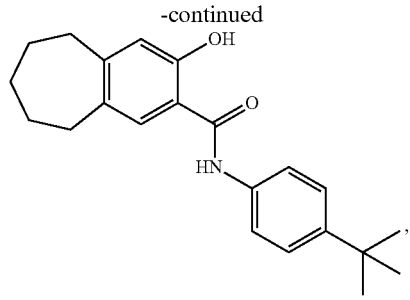
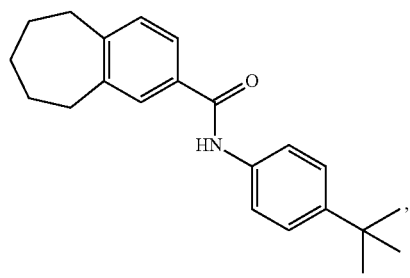
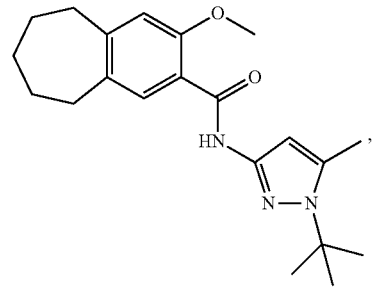
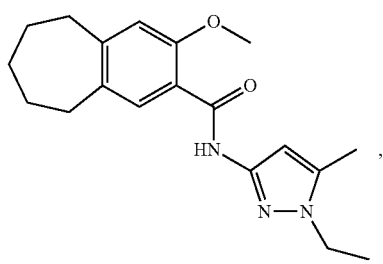
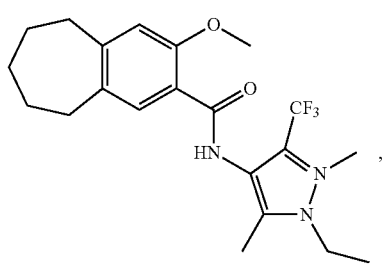
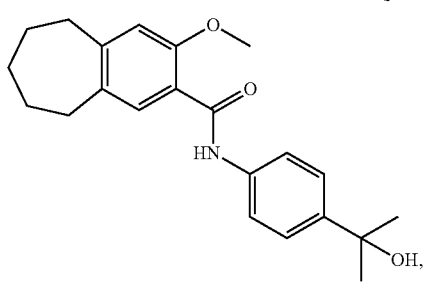
60
-continued
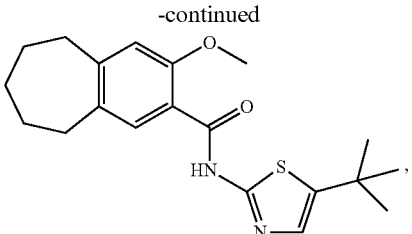
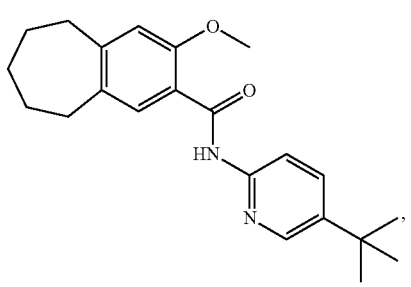
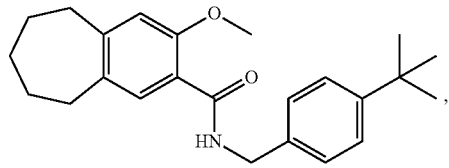
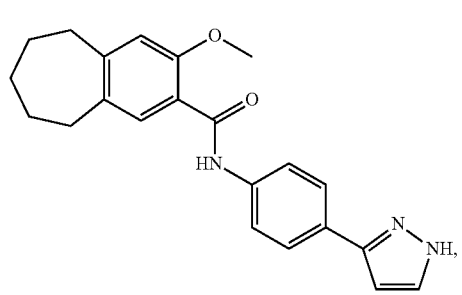
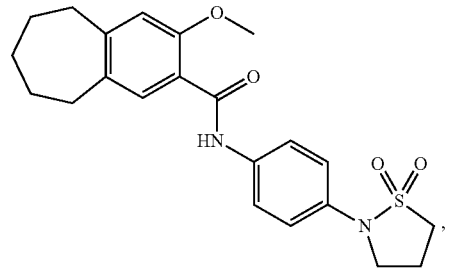
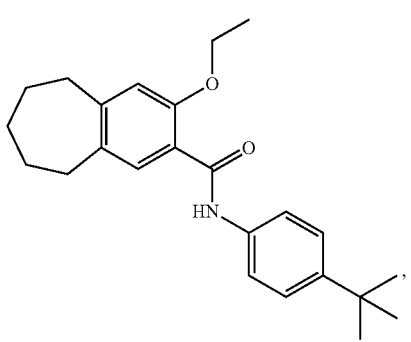

61
-continued
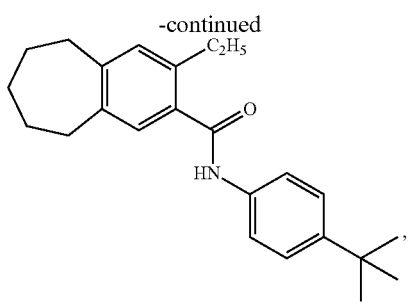
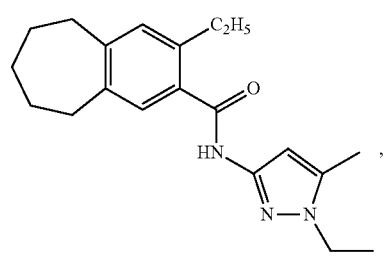
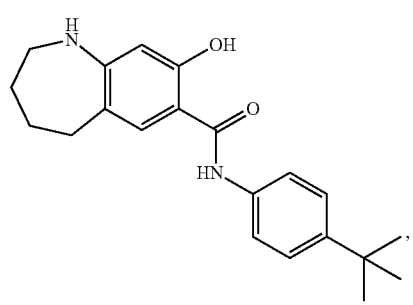
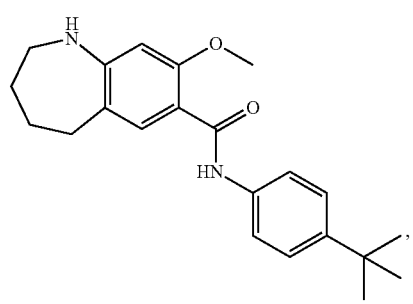
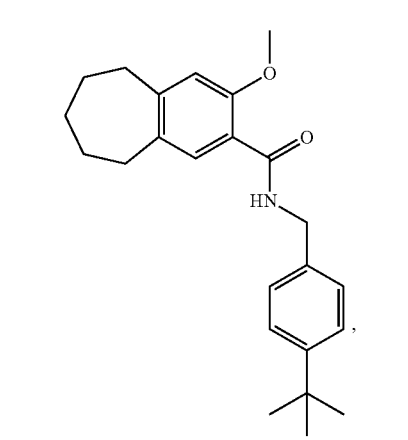
62
-continued
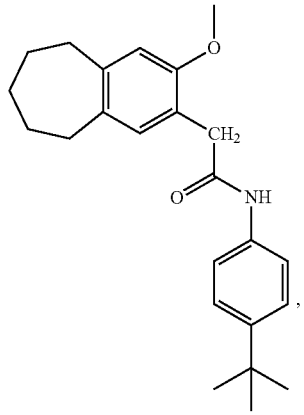
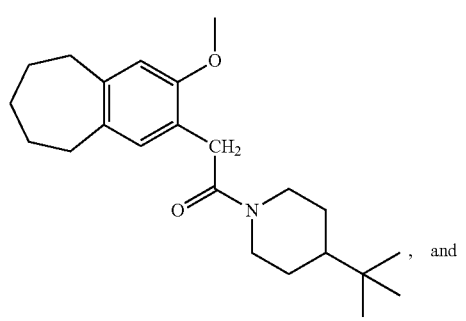
, and
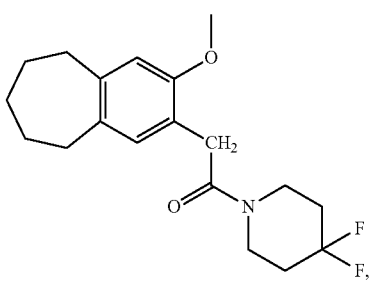
or a pharmaceutically acceptable salt thereof.
In one aspect, a compound can be present as one or more of the following structures:
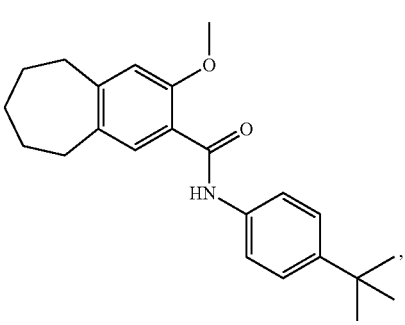

-continued

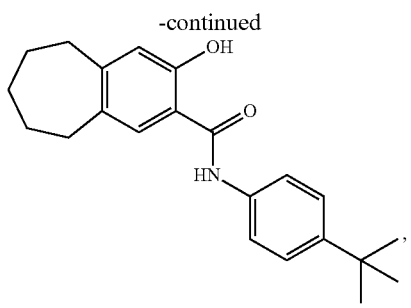
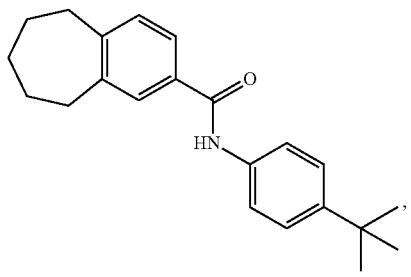
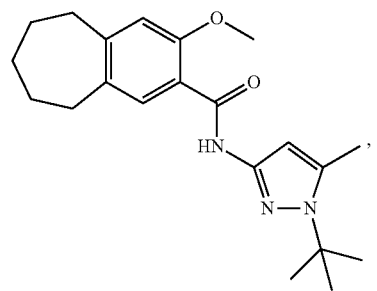
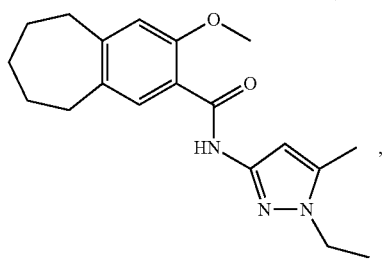
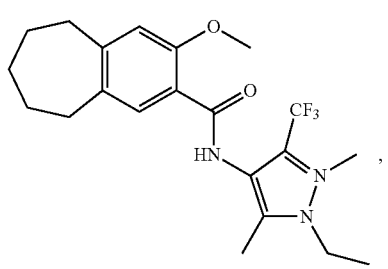
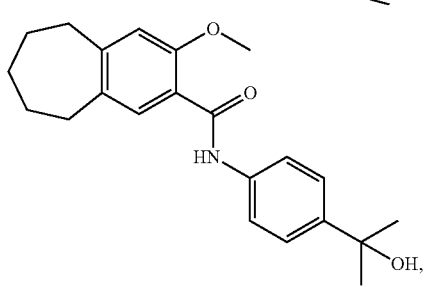

-continued

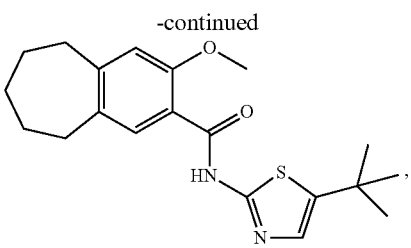
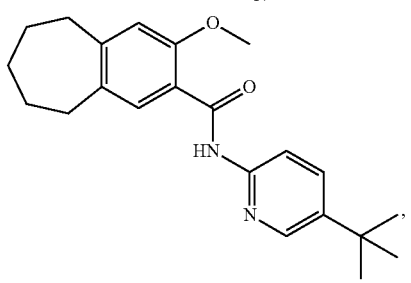
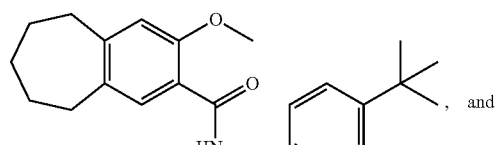
, and
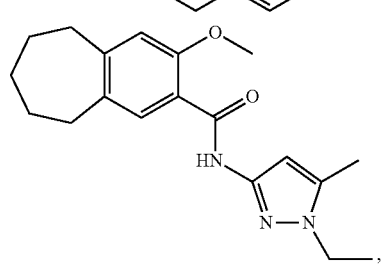

or a pharmaceutically acceptable salt thereof.

In one aspect, a compound can be present as:

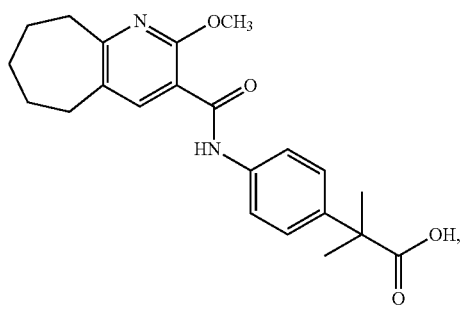 [SMILES: COc1nc2c(cc1C(=O)Nc1ccc(C(C)(C)C(=O)O)cc1)CCCCC2]

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of a viral infection, and such activity can be determined using the assay methods described herein below.

In one aspect, a compound can be selected from:

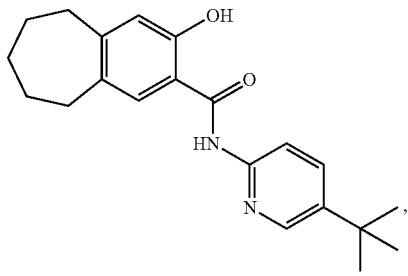

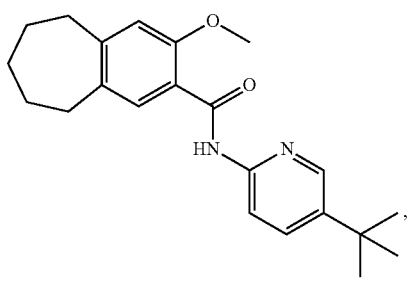

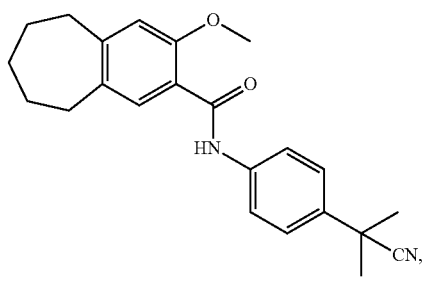

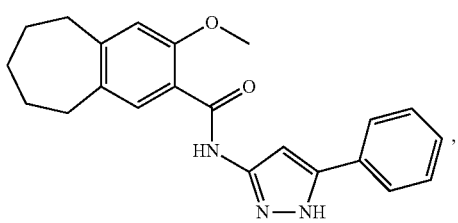

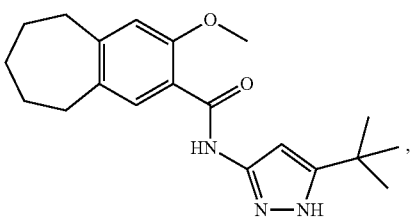

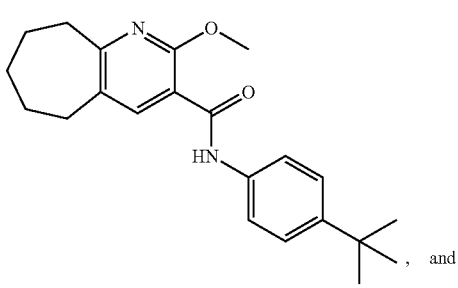, and

-continued

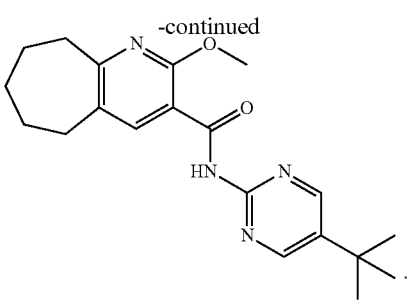

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Pharmaceutical Compositions

In one aspect, disclosed are pharmaceutical compositions comprising a disclosed compound, or a pharmaceutically acceptable salt thereof and a pharmaceutically acceptable carrier.

In one aspect, disclosed are pharmaceutical compositions comprising a pharmaceutically acceptable carrier and a therapeutically effective amount of at least one compounds having a structure represented by a formula:

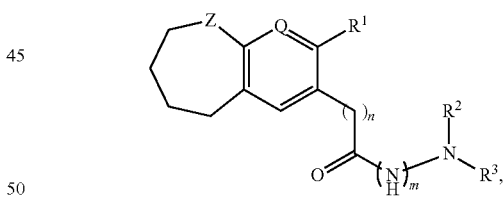

wherein each of m and n is independently selected from 0 and 1; wherein Q is selected from CH and N; wherein Z is selected from NH and CH$_2$; wherein R$^1$ is selected from hydrogen, —OH, C1-C4 alkyl, C1-C4 haloalkoxy, and C1-C4 alkoxy; wherein R$^2$ is hydrogen; and wherein R$^3$ is C2-C5 heteroaryl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar$^1$, and Ar$^1$; wherein Ar$^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein R$^3$ is a structure represented by a formula:

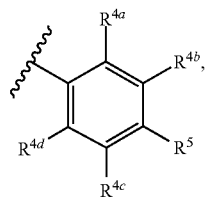

wherein each of $R^{4a}$, $R^{4b}$, $R^{4c}$, and $R^{4d}$ is independently selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar$^2$; wherein Ar$^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein R$^5$ is selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, —(C1-C4 alkyl)CO$_2$H, and Ar$^3$; and wherein Ar$^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of R$^2$ and R$^3$ are covalently bonded together and, together with the intermediate atoms, comprise a 3- to 6-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and R$^1$ is hydrogen, then R$^3$ is not pyridinyl, provided that when n is 1, then R$^5$ is not hydrogen, or provided that when R$^5$ is hydrogen, then R$^1$ is not hydrogen, or a pharmaceutically acceptable salt thereof.

In one aspect, disclosed are pharmaceutical compositions comprising a pharmaceutically acceptable carrier and a therapeutically effective amount of at least one compound having a structure represented by a formula:

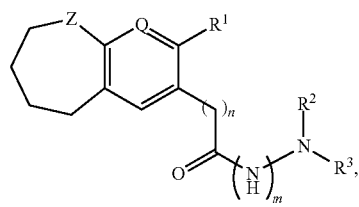

wherein each of m and n is independently selected from 0 and 1; wherein Q is selected from CH and N; wherein Z is selected from NH and CH$_2$; wherein R$^1$ is selected from hydrogen, —OH, C1-C4 alkyl, C1-C4 haloalkoxy, and C1-C4 alkoxy; wherein R$^2$ is hydrogen; and wherein R$^3$ is C2-C5 heteroaryl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar$^1$, and Ar$^1$; wherein Ar$^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein R$^3$ is a structure represented by a formula:

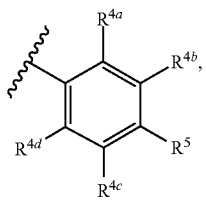

wherein each of $R^{4a}$, $R^{4b}$, $R^{4c}$, and $R^{4d}$ is independently selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar$^2$; wherein Ar$^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein R$^5$ is selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and Ar$^3$; and wherein Ar$^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of R$^2$ and R$^3$ are covalently bonded together and, together with the intermediate atoms, comprise a 3- to 6-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and R$^1$ is hydrogen, then R$^3$ is not pyridinyl, provided that when n is 1, then R$^5$ is not hydrogen, or provided that when R$^5$ is hydrogen, then R$^1$ is not hydrogen, or a pharmaceutically acceptable salt thereof.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouthwashes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a viral infection such as, for example, chikungunya, Venezuelan equine encephalitis, dengue, influenza, and zika.

It is understood that the disclosed compositions can be prepared from the disclosed compounds. It is also understood that the disclosed compositions can be employed in the disclosed methods of using.

D. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-XII, as described and exemplified below. The following examples are provided so that the invention might be more fully understood, are illustrative only, and should not be construed as limiting.

1. Route I

In one aspect, substituted benzoannulenes can be prepared as shown below.

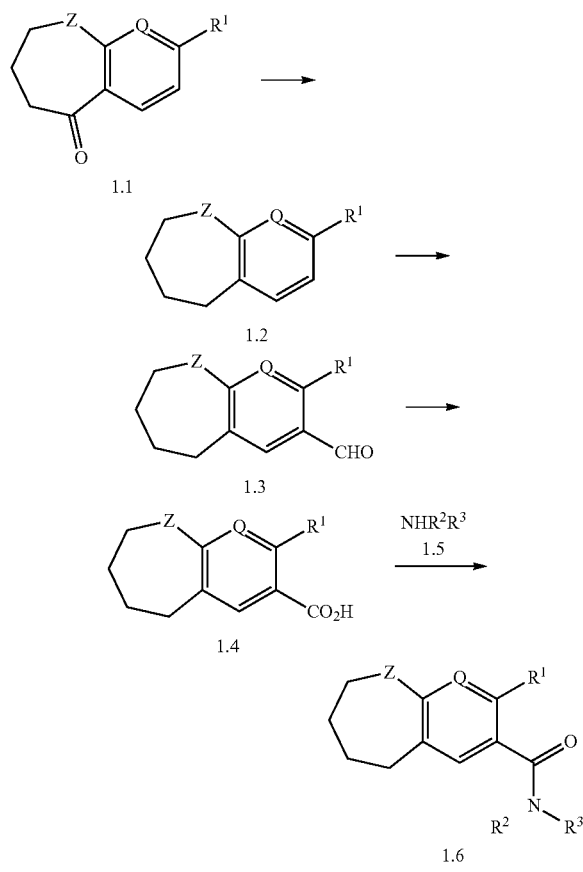

Compounds are represented in generic form, with substituents as noted in compound descriptions elsewhere herein. A more specific example is set forth below.

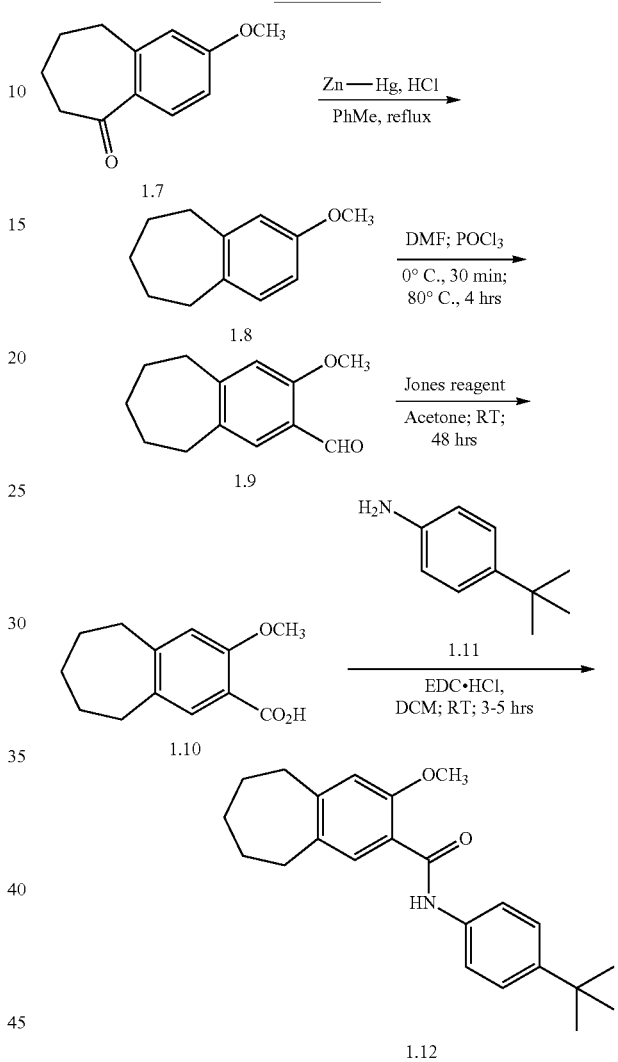

In one aspect, compounds of type 1.6, and similar compounds, can be prepared according to reaction Scheme 1B above. Thus, compounds of type 1.2 can be prepared by a reduction reaction of an appropriate carbonyl, e.g., 1.1 as shown above. Appropriate carbonyls are commercially available or prepared by methods known to one skilled in the art. The reduction reaction is carried out in the presence of an appropriate reducing agent, e.g., zinc amalgam, and an appropriate acid, e.g., hydrochloric acid, in an appropriate solvent, e.g., toluene. Compounds of type 1.3 can be prepared by an oxidation reaction of an appropriate aryl, e.g., 1.2 as shown above. The oxidation reaction is carried out in the presence of an appropriate oxidizing agent, e.g., phosphoryl chloride as shown above, in an appropriate solvent, e.g., dimethylformamide. Compounds of type 1.4 can be prepared by an oxidation reaction of an appropriate aldehyde, e.g., 1.3 as shown above. The oxidation reaction is carried out in the presence of an appropriate oxidizing agent, e.g., Jones reagent, in an appropriate solvent, e.g., acetone, for an appropriate period of time, e.g., 48 hours. Compounds of type 1.6 can be prepared by a coupling reaction between an appropriate carboxylic acid derivative, e.g., 1.4, and an appropriate amine, e.g., 1.5. Appropriate amines are commercially available or prepared by methods known to one skilled in the art. The coupling reaction is carried out in the presence of an appropriate coupling agent, e.g., N-(3-dimethylaminopropyl)-N'-ethylcarbodiimide hydrochloride, in an appropriate solvent, e.g., dichloromethane, for an appropriate period of time, e.g., 3-5 hours. As can be appreciated by one skilled in the art, the above reaction provides an example of a generalized approach wherein compounds similar in structure to the specific reactants above (compounds similar to compounds of type 1.7, 1.8, 1.9, 1.10, and 1.11), can be substituted in the reaction to provide substituted benzoannulene derivatives similar to Formula 1.12.

2. Route II

In one aspect, substituted benzoannulenes can be prepared as shown below.

SCHEME 2A.

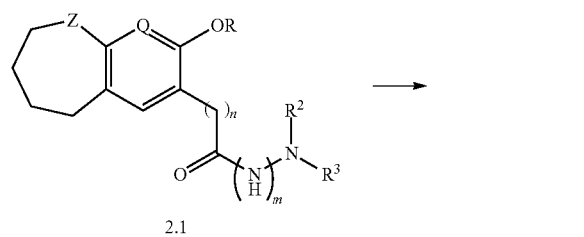

2.1

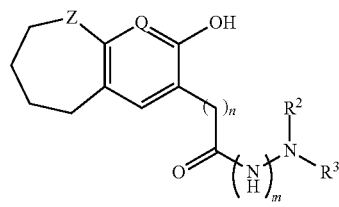

2.2

Compounds are represented in generic form, wherein R is C1-C4 alkyl or C1-C4 haloalkyl, and with substituents as noted in compound descriptions elsewhere herein. A more specific example is set forth below.

SCHEME 2B.

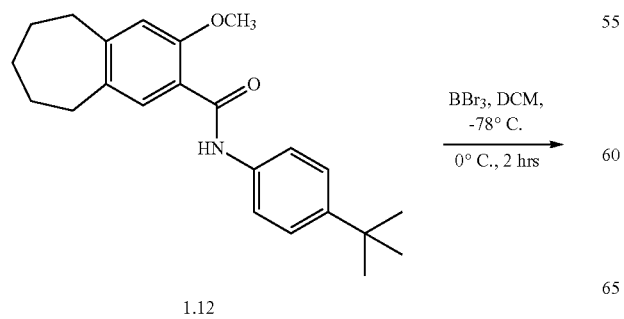

1.12

BBr$_3$, DCM, -78° C.

0° C., 2 hrs

-continued

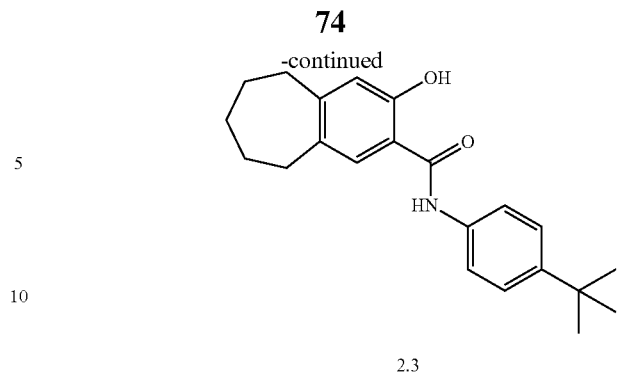

2.3

In one aspect, compounds of type 2.2, and similar compounds, can be prepared according to reaction Scheme 2B above. Thus, compounds of type 2.2 can be prepared by a reduction reaction of an appropriate alkoxy derivative, e.g., 2.1 as shown above. Appropriate alkoxy derivatives are commercially available or prepared by methods known to one skilled in the art. The reduction reaction is carried out in the presence of an appropriate reducing agent, e.g., boron tribromide, in an appropriate solvent, e.g., dichloromethane. As can be appreciated by one skilled in the art, the above reaction provides an example of a generalized approach wherein compounds similar in structure to the specific reactants above (compounds similar to compounds of type 1.12), can be substituted in the reaction to provide substituted benzoannulene derivatives similar to Formula 2.3.

3. Route III

In one aspect, substituted benzoannulenes can be prepared as shown below.

SCHEME 3A.

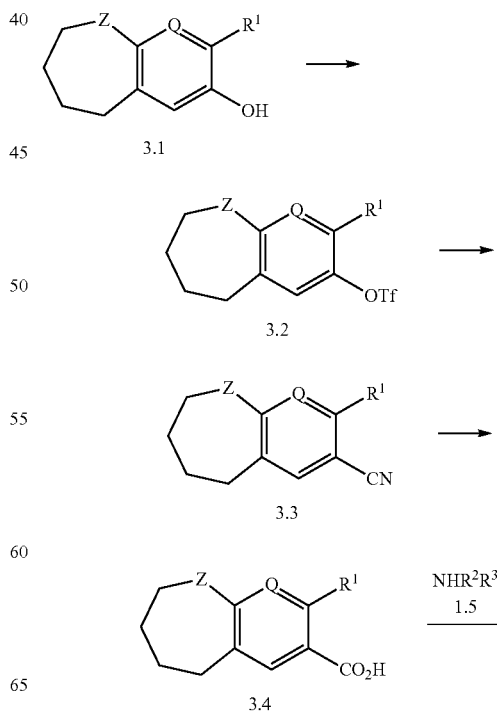

NHR$^2$R$^3$
1.5

-continued

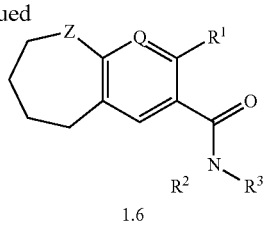
1.6

Compounds are represented in generic form, with substituents as noted in compound descriptions elsewhere herein. A more specific example is set forth below.

SCHEME 3B.

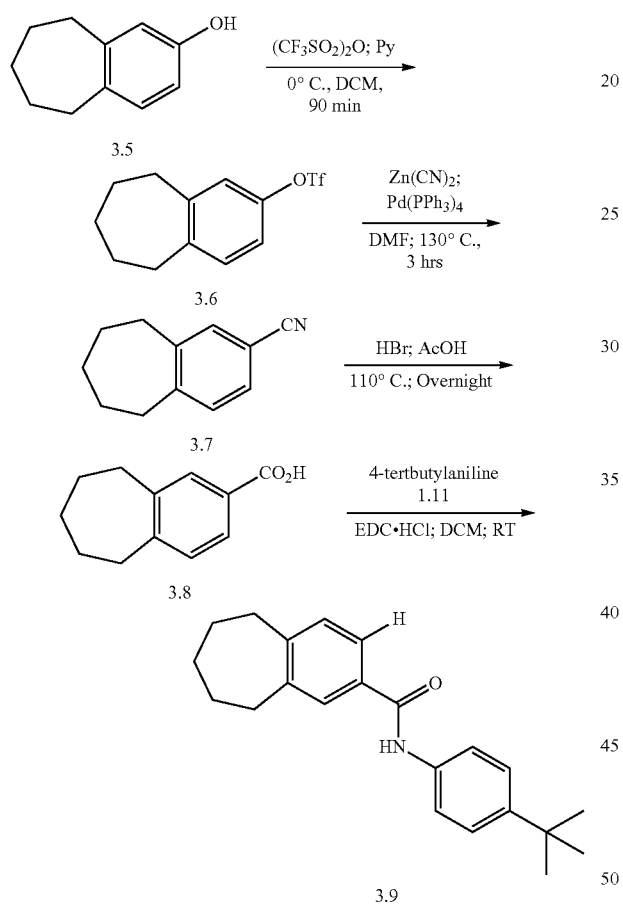

In one aspect, compounds of type, and similar compounds, can be prepared according to reaction Scheme 3B above. Thus, compounds of type 3.2 can be prepared by a sulfonylation reaction of an appropriate phenol derivative, e.g., 3.1 as shown above. Appropriate phenol derivatives are commercially available or prepared by methods known to one skilled in the art. The sulfonylation reaction is carried out in the presence of an appropriate nucleophile, e.g., trifluoromethanesulfonic anhydride, and an appropriate base, e.g., pyridine, in an appropriate solvent, e.g., dichloromethane, at an appropriate temperature, e.g., 0° C., for an appropriate period of time, e.g., 90 minutes. Compounds of type 3.3 can be prepared by reduction of an appropriate aryl, e.g., 3.2 as shown above. The reduction is carried out in the presence of an appropriate reducing agent, e.g., zinc cyanide as shown above, and an appropriate catalyst, e.g., tetrakis (triphenylphosphine)palladium (0), in an appropriate solvent, e.g., dimethylformamide, at an appropriate temperature, e.g., 130° C., for an appropriate period of time, 3 hours. Compounds of type 3.4 can be prepared by an oxidation reaction of an appropriate cyano derivative, e.g., 3.3 as shown above. The oxidation reaction is carried out in the presence of an appropriate acid, e.g., hydrobromic acid, in an appropriate solvent, e.g., acetic acid, at an appropriate temperature, e.g., 110° C. Compounds of type 1.6 can be prepared by a coupling reaction between an appropriate carboxylic acid derivative, e.g., 3.4, and an appropriate amine, e.g., 1.5. Appropriate amines are commercially available or prepared by methods known to one skilled in the art. The coupling reaction is carried out in the presence of an appropriate coupling agent, e.g., N-(3-dimethylaminopropyl)-N'-ethylcarbodiimide hydrochloride, in an appropriate solvent, e.g., dichloromethane. As can be appreciated by one skilled in the art, the above reaction provides an example of a generalized approach wherein compounds similar in structure to the specific reactants above (compounds similar to compounds of type 1.11, 3.5, 3.6, 3.7, and 3.8), can be substituted in the reaction to provide substituted benzoannulene derivatives similar to Formula 3.9.

4. Route IV

In one aspect, substituted benzoannulenes can be prepared as shown below.

SCHEME 4A.

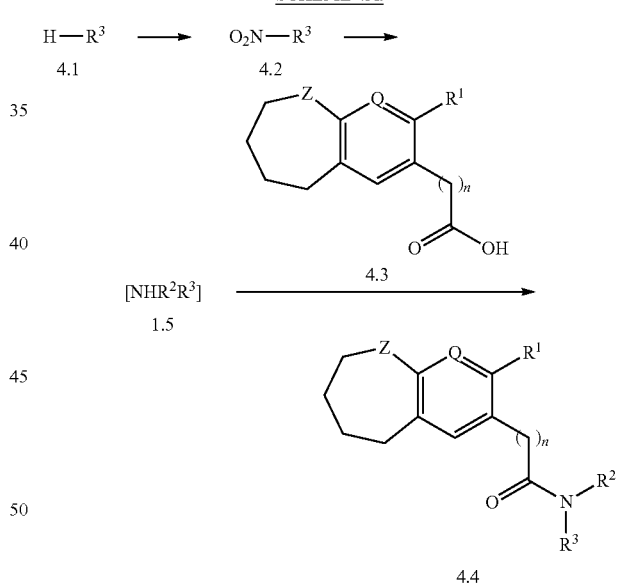

Compounds are represented in generic form, with substituents as noted in compound descriptions elsewhere herein. A more specific example is set forth below.

SCHEME 4B.

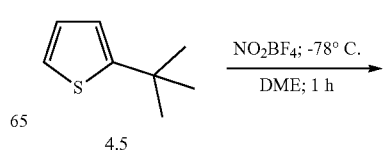

-continued

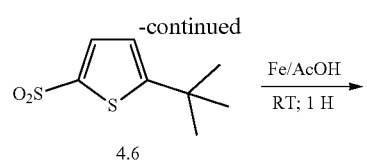

5. Route V

In one aspect, substituted benzoannulenes can be prepared as shown below.

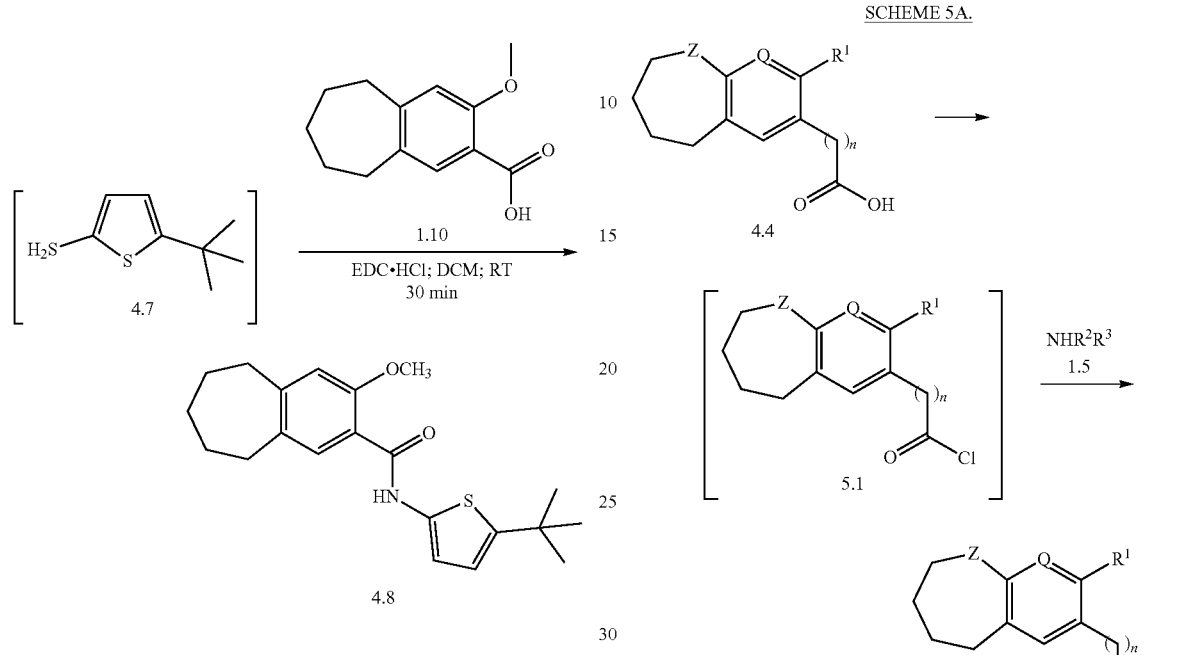

In one aspect, compounds of type 4.5, and similar compounds, can be prepared according to reaction Scheme 4B above. Thus, compounds of type 4.2 can be prepared by a nucleophilic substitution reaction of an appropriate aryl derivative, e.g., 4.1 as shown above. Appropriate aryls are commercially available or prepared by methods known to one skilled in the art. The nucleophilic substitution reaction is carried out in the presence of an appropriate nucleophilic agent, e.g., nitronium tetrafluoroborate as shown above, in an appropriate solvent, e.g., dimethyl ether, at an appropriate temperature, e.g., −78° C., for an appropriate period of time, e.g., 1 hour. Compounds of type 1.5 can be prepared by reduction of an appropriate nitrone, e.g., 4.2 as shown above. The reduction is carried out in the presence of an appropriate reducing agent, e.g., iron as shown above, in an appropriate solvent, e.g., acetic acid, for an appropriate period of time, e.g., 1 hour. Compounds of type 4.4 can be prepared by a coupling reaction between an appropriate carboxylic acid derivative, e.g., 4.3, and an appropriate amine, e.g., 1.5. Appropriate amines are commercially available or prepared by methods known to one skilled in the art. The coupling reaction is carried out in the presence of an appropriate coupling agent, e.g., N-(3-dimethylaminopropyl)-N'-ethylcarbodiimide hydrochloride, in an appropriate solvent, e.g., dichloromethane, for an appropriate period of time, e.g., 30 minutes. As can be appreciated by one skilled in the art, the above reaction provides an example of a generalized approach wherein compounds similar in structure to the specific reactants above (compounds similar to compounds of type 1.10, 4.5, 4.6, and 4.7), can be substituted in the reaction to provide substituted benzoannulene derivatives similar to Formula 4.8.

Compounds are represented in generic form, with substituents as noted in compound descriptions elsewhere herein. A more specific example is set forth below.

SCHEME 5B.

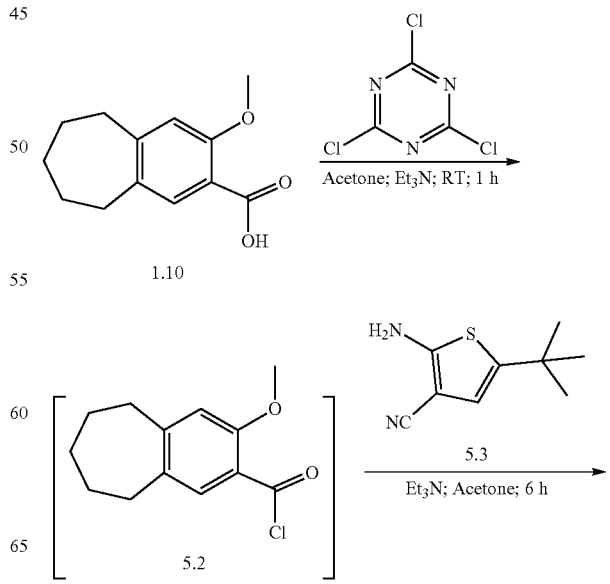

-continued

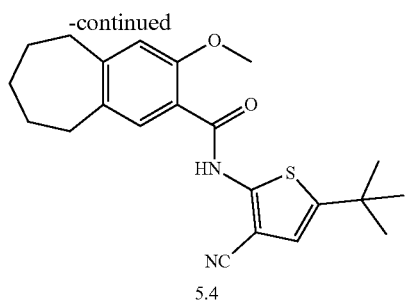

5.4

In one aspect, compounds of type 4.5, and similar compounds, can be prepared according to reaction Scheme 5B above. Thus, compounds of type 5.1 can be prepared by a nucleophilic substitution reaction of an appropriate carboxylic acid, e.g., 4.4 as shown above. Appropriate carboxylic acids are commercially available or prepared by methods known to one skilled in the art. The nucleophilic substitution reaction is carried out in the presence of an appropriate nucleophilic agent, e.g., 2,4,6-trichloro-1,3,5-triazine as shown above, and an appropriate base, e.g., triethylamine, in an appropriate solvent, e.g., acetone, for an appropriate period of time, e.g., 1 hour. Compounds of type 4.5 can be prepared by a coupling reaction between an appropriate acid chloride, e.g., 5.1, and an appropriate amine, e.g., 1.5. Appropriate amines are commercially available or prepared by methods known to one skilled in the art. The coupling reaction is carried out in the presence of an appropriate base, e.g., triethylamine, in an appropriate solvent, e.g., acetone, for an appropriate period of time, e.g., 6 hours. As can be appreciated by one skilled in the art, the above reaction provides an example of a generalized approach wherein compounds similar in structure to the specific reactants above (compounds similar to compounds of type 1.10, 5.2, and 5.3), can be substituted in the reaction to provide substituted benzoannulene derivatives similar to Formula 5.4.

6. Route VI

In one aspect, substituted benzoannulenes can be prepared as shown below.

SCHEME 6A.

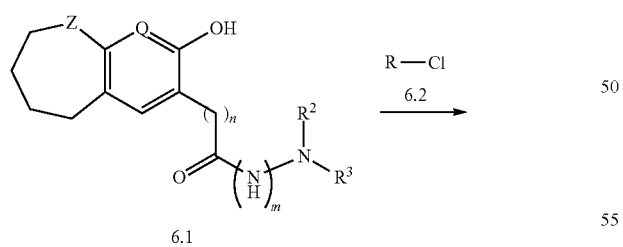

Compounds are represented in generic form, wherein R is C1-C4 alkyl or C1-C4 haloalkyl, and with substituents as noted in compound descriptions elsewhere herein. A more specific example is set forth below.

SCHEME 6B.

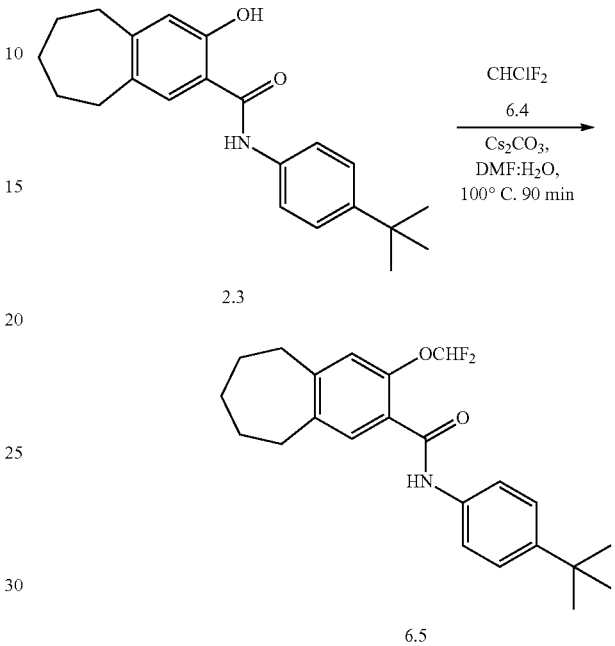

In one aspect, compounds of type 6.3, and similar compounds, can be prepared according to reaction Scheme 6B above. Thus, compounds of type 6.3 can be prepared by an alkylation reaction of an appropriate alcohol, e.g., 6.1 as shown above. The alkylation reaction is carried out in the presence of an appropriate alkyl halide, e.g., 6.4 as shown above, and an appropriate base, e.g., cesium carbonate, in an appropriate solvent system, e.g., dimethylformamide and water, at an appropriate temperature, e.g., 100° C., for an appropriate period of time, e.g., 90 minutes. As can be appreciated by one skilled in the art, the above reaction provides an example of a generalized approach wherein compounds similar in structure to the specific reactants above (compounds similar to compounds of type 2.3 and 6.4), can be substituted in the reaction to provide substituted benzoannulene derivatives similar to Formula 6.5.

7. Route VII

In one aspect, substituted benzoannulenes can be prepared as shown below.

SCHEME 7A.

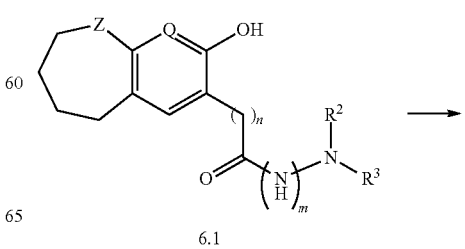

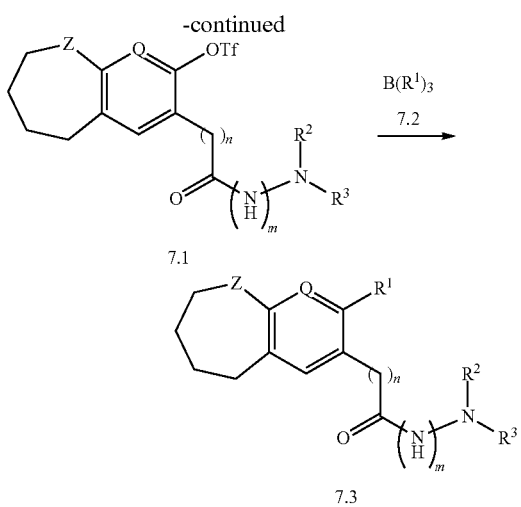

Compounds are represented in generic form, with substituents as noted in compound descriptions elsewhere herein. A more specific example is set forth below.

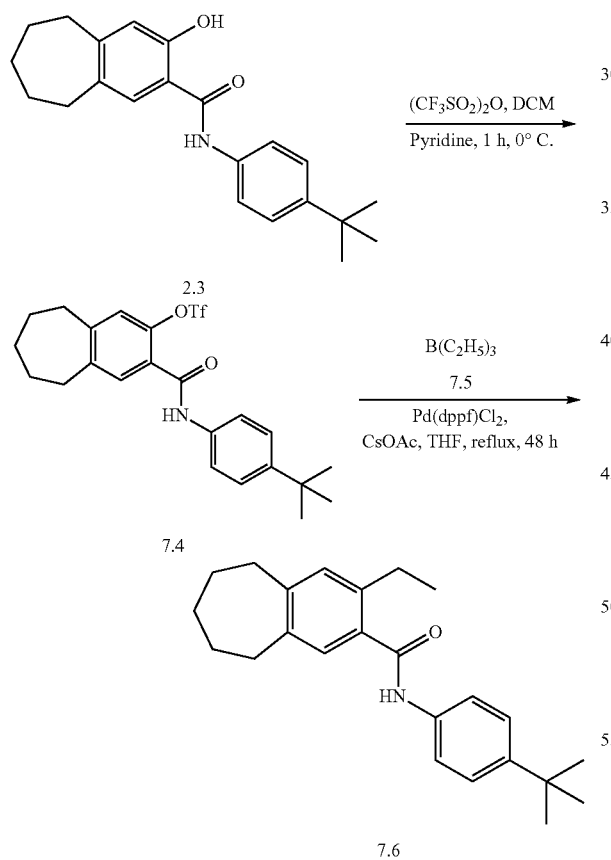

In one aspect, compounds of type 7.3, and similar compounds, can be prepared according to reaction Scheme 7B above. Thus, compounds of type 7.1 can be prepared by a sulfonylation reaction of an appropriate phenol derivative, e.g., 6.1 as shown above. The sulfonylation reaction is carried out in the presence of an appropriate nucleophile, e.g., trifluoromethanesulfonic anhydride, and an appropriate base, e.g., pyridine, in an appropriate solvent, e.g., dichloromethane, for an appropriate period of time, e.g., 1 hour, at an appropriate temperature, e.g., 0° C. Compounds of type 7.3 can be prepared by a substitution reaction of an appropriate aryl derivative, e.g., 7.1. The substitution reaction is carried out in the presence of an appropriate organoborane, e.g., triethylboron, an appropriate catalyst, e.g., [1,1'-bis(diphenylphosphino)ferrocene] dichloropalladium(II), and an appropriate base, e.g., cesium acetate, in an appropriate solvent, e.g., tetrahydrofuran, for an appropriate period of time, e.g., 48 hours. As can be appreciated by one skilled in the art, the above reaction provides an example of a generalized approach wherein compounds similar in structure to the specific reactants above (compounds similar to compounds of type 2.3, 7.4, and 7.5), can be substituted in the reaction to provide substituted benzoannulene derivatives similar to Formula 7.6.

8. Route VIII

In one aspect, substituted benzoannulenes can be prepared as shown below.

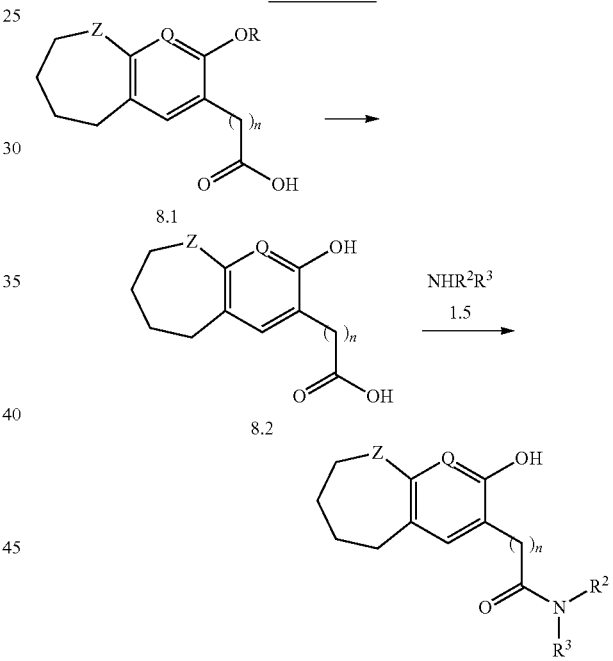

Compounds are represented in generic form, wherein R is C1-C4 alkyl or C1-C4 haloalkyl, and with substituents as noted in compound descriptions elsewhere herein. A more specific example is set forth below.

SCHEME 8B.

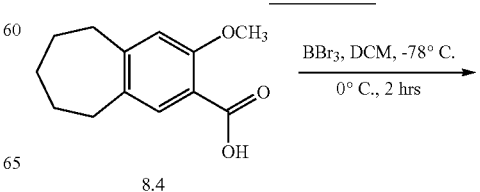

SCHEME 9A.

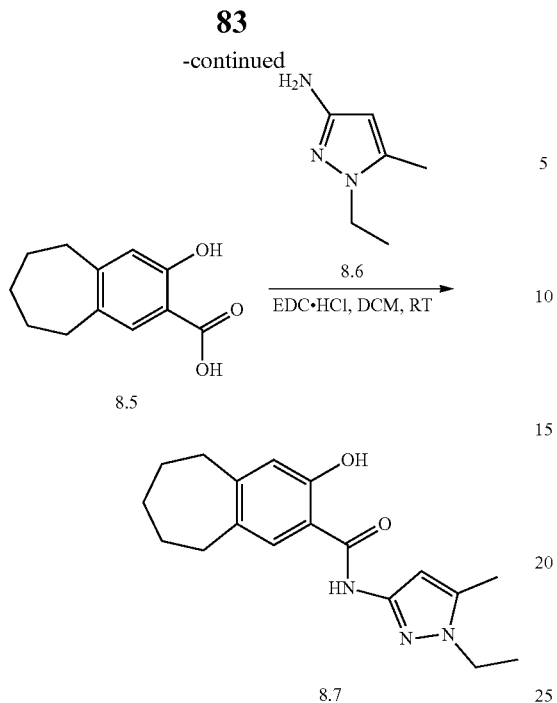

In one aspect, compounds of type 8.3, and similar compounds, can be prepared according to reaction Scheme 8B above. Thus, compounds of type 8.2 can be prepared by reduction of an appropriate alkoxy, e.g., 8.1 as shown above. The reduction is carried out in the presence of an appropriate reducing agent, e.g., boron tribromide, in an appropriate solvent, e.g., dichloromethane, for an appropriate period of time, e.g., 2 hours. Compounds of type 8.3 can be prepared by a coupling reaction between an appropriate carboxylic acid derivative, e.g., 8.2, and an appropriate amine, e.g., 1.5. Appropriate amines are commercially available or prepared by methods known to one skilled in the art. The coupling reaction is carried out in the presence of an appropriate coupling agent, e.g., N-(3-dimethylaminopropyl)-N'-ethyl-carbodiimide hydrochloride, in an appropriate solvent, e.g., dichloromethane. As can be appreciated by one skilled in the art, the above reaction provides an example of a generalized approach wherein compounds similar in structure to the specific reactants above (compounds similar to compounds of type 8.4, 8.5, and 8.6), can be substituted in the reaction to provide substituted benzoannulene derivatives similar to Formula 8.7.

9. Route IX

In one aspect, substituted benzoannulenes can be prepared as shown below.

Compounds are represented in generic form, wherein PG is an amine protecting group and with substituents as noted in compound descriptions elsewhere herein. A more specific example is set forth below.

SCHEME 9B.

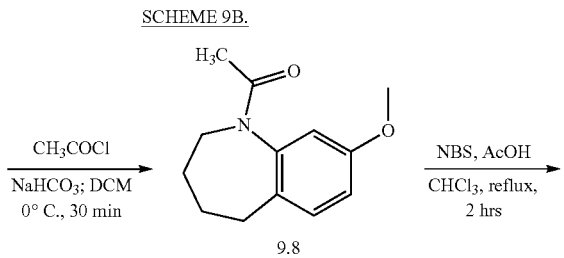

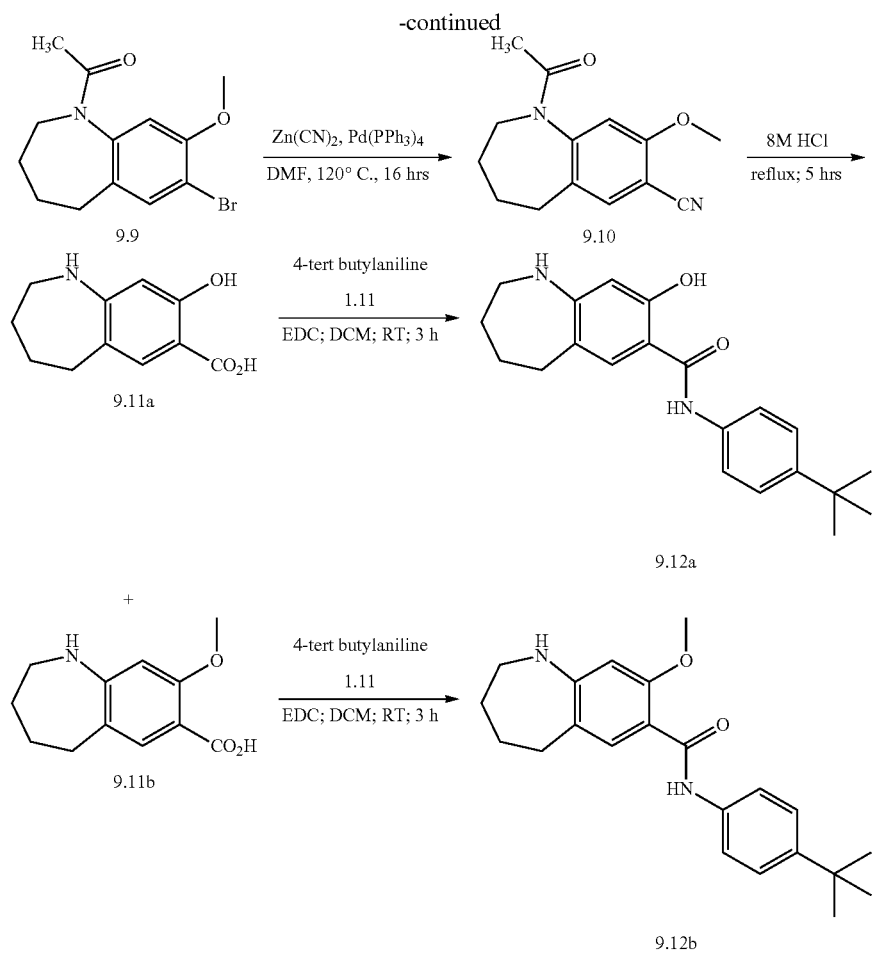

In one aspect, compounds of type 9.6, and similar compounds, can be prepared according to reaction Scheme 9B above. Thus, compounds of type 9.2 can be prepared by protection of an appropriate amine, e.g., 9.1 as shown above. The protection is carried out in the presence of an appropriate protecting group agent, e.g., acetyl chloride as shown above, and an appropriate base, e.g., sodium carbonate, in an appropriate solvent, e.g., dichloromethane, at an appropriate temperature, e.g., 0° C., for an appropriate period of time, e.g., 30 minutes. Compounds of type 9.3 can be prepared by a halogenation reaction of an appropriate aryl, e.g., 9.2 as shown above. The halogenation reaction is carried out in the presence of an appropriate halide source, e.g., N-bromosuccinimide, and an appropriate acid, e.g., acetic acid, in an appropriate solvent, e.g., chloroform, for an appropriate period of time, e.g., 2 hours. Compounds of type 9.4 can be prepared by a nucleophilic substitution of an appropriate halide, e.g., 9.3 as shown above. The nucleophilic substitution reaction is carried out in the presence of an appropriate nucleophilic agent, e.g., zinc cyanide, and an appropriate catalyst, e.g., tetrakis(triphenylphosphine)palladium (0), in an appropriate solvent, e.g., dimethylformamide, at an appropriate temperature, e.g., 120° C., for an appropriate period of time, e.g., 16 hours. Compounds of type 9.5 can be prepared by oxidation of an appropriate cyano compound, e.g., 9.4 as shown above. The oxidation is carried out in the presence of an appropriate aqueous acid, e.g., 8M hydrochloric acid as shown above, for an appropriate period of time, e.g., 5 hours. Compounds of type 9.6 can be prepared by a coupling reaction between an appropriate carboxylic acid derivative, e.g., 9.5, and an appropriate amine, e.g., 1.5. Appropriate amines are commercially available or prepared by methods known to one skilled in the art. The coupling reaction is carried out in the presence of an appropriate coupling agent, e.g., N-(3-dimethylaminopropyl)-N'-ethyl-carbodiimide hydrochloride, in an appropriate solvent, e.g., dichloromethane, for an appropriate period of time, e.g., 3 hours. As can be appreciated by one skilled in the art, the above reaction provides an example of a generalized approach wherein compounds similar in structure to the specific reactants above (compounds similar to compounds of type 1.11, 9.7, 9.8, 9.9, 9.10, 9.11a, and 9.11b), can be substituted in the reaction to provide substituted benzoannulene derivatives similar to Formulas 9.12a and 9.12b.

10. Route X

In one aspect, substituted benzoannulenes can be prepared as shown below.

SCHEME 10A.

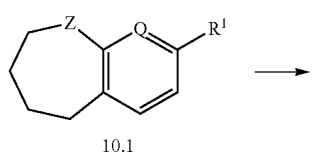

10.1

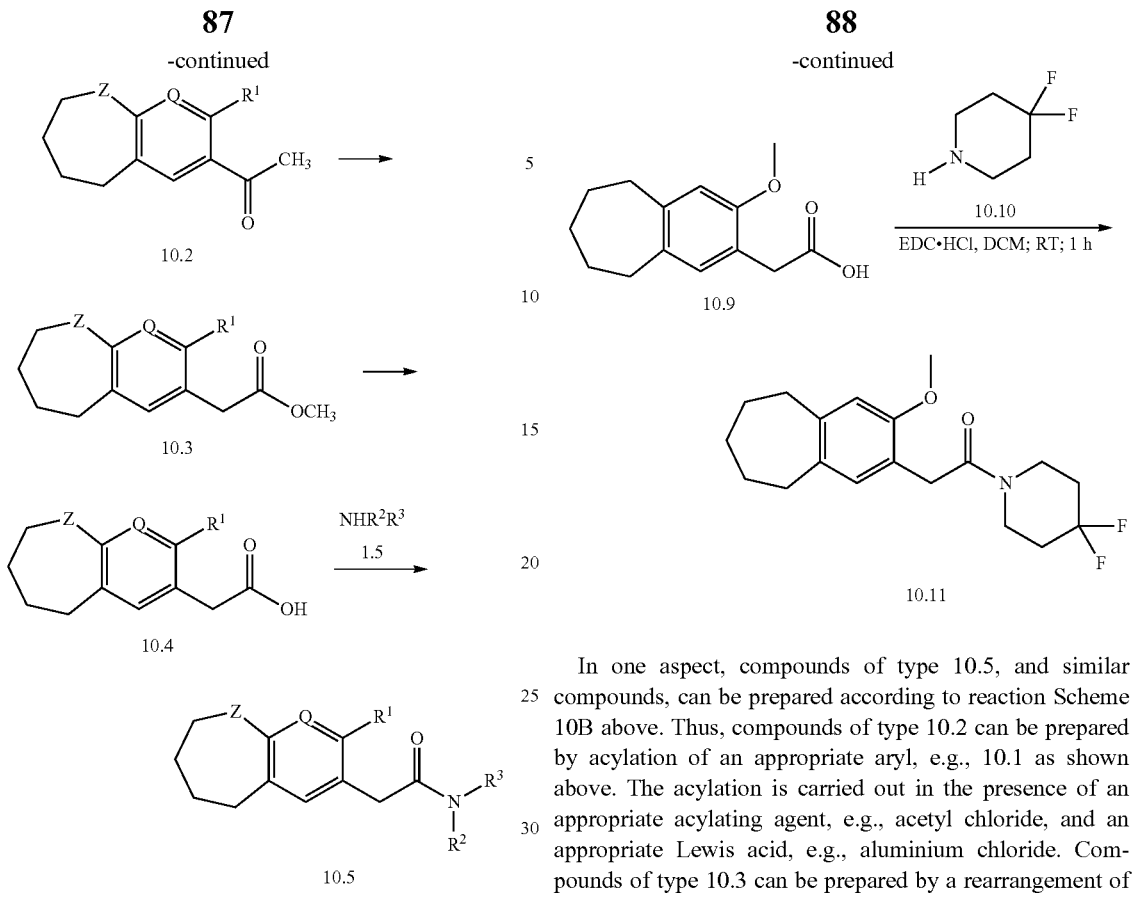

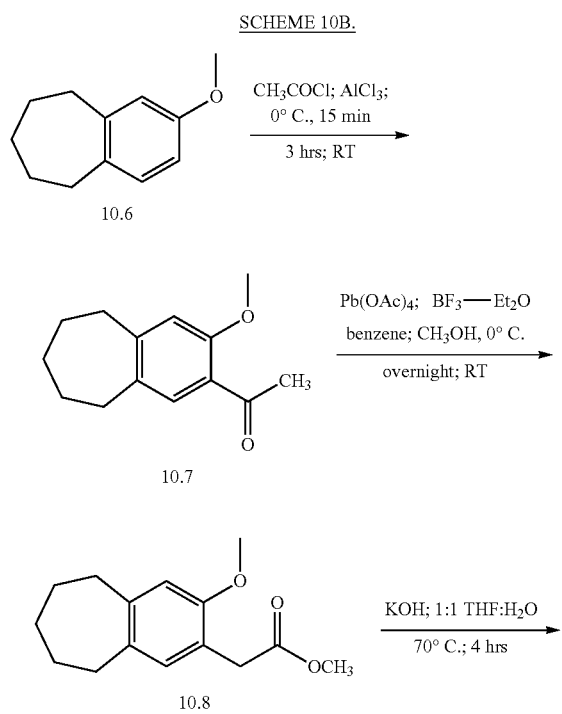

Compounds are represented in generic form, with substituents as noted in compound descriptions elsewhere herein. A more specific example is set forth below.

In one aspect, compounds of type 10.5, and similar compounds, can be prepared according to reaction Scheme 10B above. Thus, compounds of type 10.2 can be prepared by acylation of an appropriate aryl, e.g., 10.1 as shown above. The acylation is carried out in the presence of an appropriate acylating agent, e.g., acetyl chloride, and an appropriate Lewis acid, e.g., aluminium chloride. Compounds of type 10.3 can be prepared by a rearrangement of an appropriate aryl acetate, e.g., 10.2 as shown above. The rearrangement is carried out in the presence of an appropriate catalyst, e.g., lead (IV) acetate, an appropriate Lewis acid, e.g., boron trifluoride diethyl etherate, and an appropriate alcohol, e.g., methanol, in an appropriate solvent, e.g., benzene, at an appropriate temperature, e.g., 0° C. Compounds of type 10.4 can be prepared by hydrolysis of an appropriate ester, e.g., 10.3 as shown above. The hydrolysis is carried out in the presence of an appropriate base, e.g., potassium hydroxide, in an appropriate solvent system, e.g., tetrahydrofuran and water, at an appropriate temperature, e.g., 70° C., for an appropriate period of time, e.g., 4 hours. Compounds of type 10.5 can be prepared by a coupling reaction between an appropriate carboxylic acid derivative, e.g., 10.4, and an appropriate amine, e.g., 1.5. Appropriate amines are commercially available or prepared by methods known to one skilled in the art. The coupling reaction is carried out in the presence of an appropriate coupling agent, e.g., N-(3-dimethylaminopropyl)-N'-ethylcarbodiimide hydrochloride, in an appropriate solvent, e.g., dichloromethane, for an appropriate period of time, e.g., 1 hour. As can be appreciated by one skilled in the art, the above reaction provides an example of a generalized approach wherein compounds similar in structure to the specific reactants above (compounds similar to compounds of type 10.6, 10.7, 10.8, 10.9, and 10.10), can be substituted in the reaction to provide substituted benzoannulene derivatives similar to Formula 10.11.

11. Route XI

In one aspect, substituted benzoannulenes can be prepared as shown below.

SCHEME 11A.

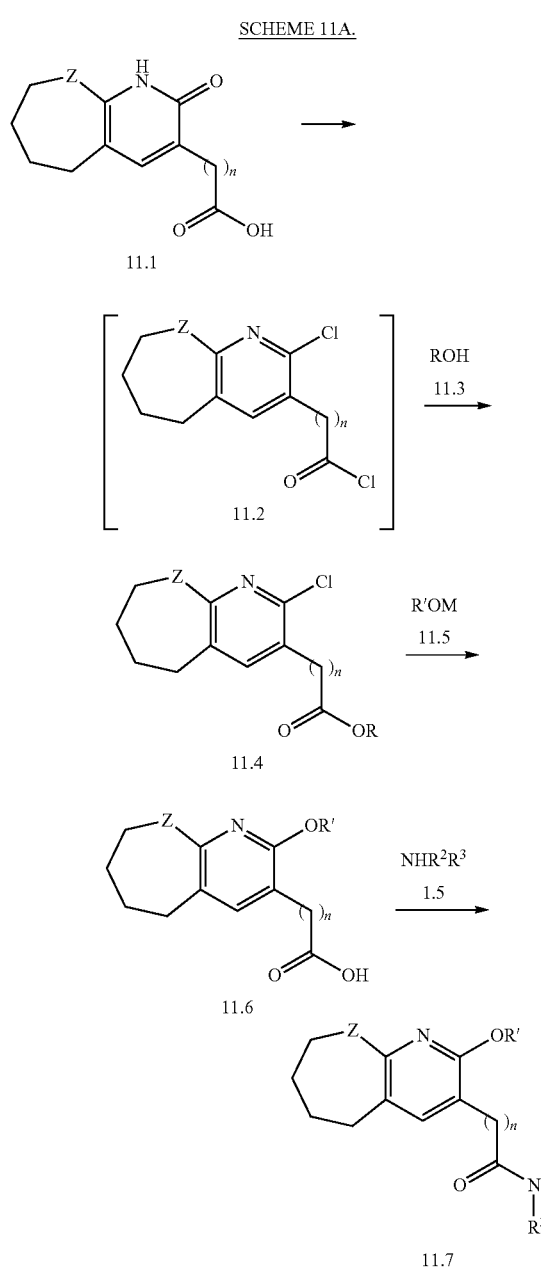

Compounds are represented in generic form, wherein R is C1-C4 alkyl, R' is C1-C4 alkyl or C1-C4 haloalkyl, and M is a metal, and with substituents as noted in compound descriptions elsewhere herein. A more specific example is set forth below.

SCHEME 11B.

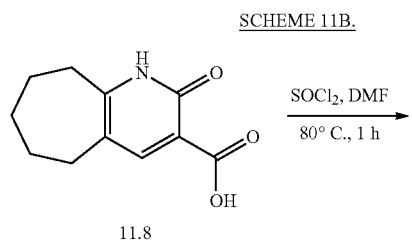

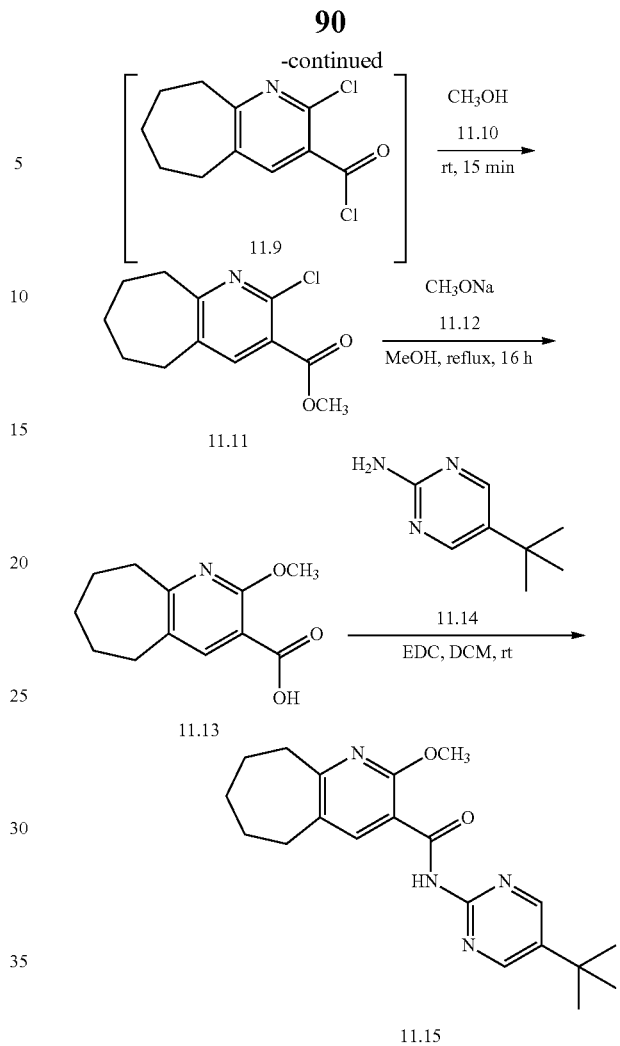

In one aspect, compounds of type 11.7, and similar compounds, can be prepared according to reaction Scheme 11B above. Thus, compounds of type 11.2 can be prepared by conversion of an appropriate carboxylic acid, e.g., 11.1 as shown above, into an acid chloride. The conversion is carried out in the presence of an appropriate halide source, e.g., thionyl chloride, in an appropriate solvent, e.g., dimethylformamide, for an appropriate period of time, e.g., 1 hour, at an appropriate temperature, e.g., 80° C. Compounds of type 11.4 can be prepared by a coupling reaction between an appropriate acid chloride, e.g., 11.2, and an appropriate alcohol, e.g., 11.3. Appropriate alcohols are commercially available or prepared by methods known to one skilled in the art. Compounds of type 11.6 can be prepared by a nucleophilic substitution reaction of an appropriate aryl halide, e.g., 11.4 as shown above. The nucleophilic substitution reaction is carried out in the presence of an appropriate metal oxide, e.g., 11.5 as shown above, in an appropriate protic solvent, e.g., methanol, for an appropriate period of time, e.g., 16 hours. Compounds of type 11.7 can be prepared by a coupling reaction between an appropriate carboxylic acid, e.g., 11.6 as shown above, and an appropriate amine, e.g., 1.5. Appropriate amines are commercially available or prepared by methods known to one skilled in the art. The coupling reaction is carried out in the presence of an appropriate coupling agent, e.g., N-(3-dimethylaminopropyl)-N'-ethylcarbodiimide hydrochloride, in an appropriate solvent, e.g., dichloromethane. As can be appreciated by one skilled in the art, the above reaction provides an example of a generalized approach wherein compounds similar in structure to the specific reactants above (compounds similar to compounds of type 11.8, 11.9, 11.10, 11.11, 11.12, 11.13, and 11.14), can be substituted in the reaction to provide substituted benzoannulene derivatives similar to Formula 11.15.

12. Route XII

In one aspect, substituted benzoannulenes can be prepared as shown below.

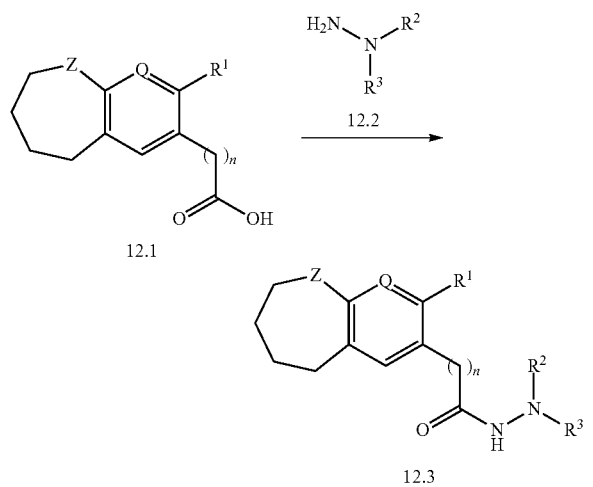

Compounds are represented in generic form, with substituents as noted in compound descriptions elsewhere herein. A more specific example is set forth below.

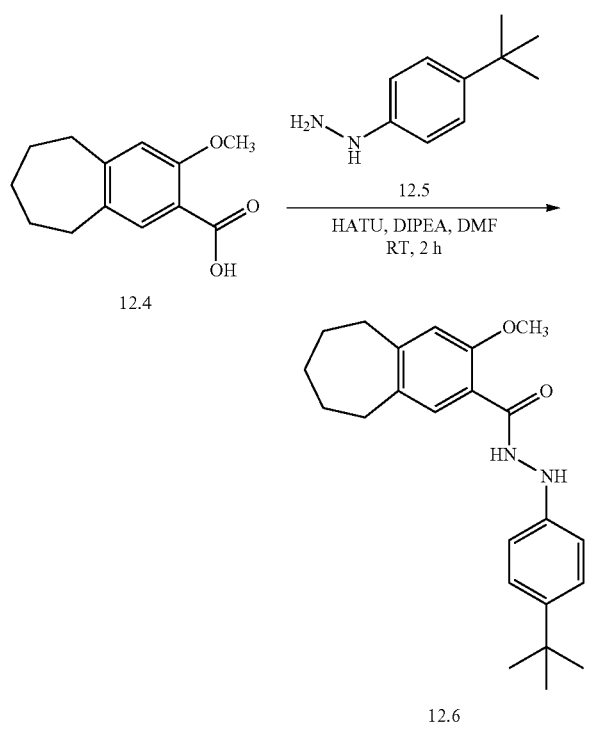

In one aspect, compounds of type 12.3, and similar compounds, can be prepared according to reaction Scheme 12B above. Thus, compounds of type 12.3 can be prepared by a coupling reaction between an appropriate carboxylic acid derivative, e.g., 8.2, and an appropriate hydrazine, e.g., 12.2. Appropriate hydrazines are commercially available or prepared by methods known to one skilled in the art. The coupling reaction is carried out in the presence of an appropriate coupling agent, e.g., 1-[bis(dimethylamino) methylene]-1H-1,2,3-triazolo[4,5-b]pyridinium 3-oxid hexafluorophosphate, and an appropriate base, e.g., diisopropylethylamine, in an appropriate solvent, e.g., dimethylformamide, for an appropriate period of time, e.g., 2 hours. As can be appreciated by one skilled in the art, the above reaction provides an example of a generalized approach wherein compounds similar in structure to the specific reactants above (compounds similar to compounds of type 12.4 and 12.5), can be substituted in the reaction to provide substituted benzoannulene derivatives similar to Formula 12.6.

E. Methods of Using the Compounds

The compounds and pharmaceutical compositions of the invention are useful in treating or controlling disorders associated with a viral infection, in particular, chikungunya, Venezuelan equine encephalitis, dengue, influenza, and zika.

Examples of viral infections for which the compounds and compositions can be useful in treating, include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a viral infection, such as chikungunya, Venezuelan equine encephalitis, dengue, influenza, and zika.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a viral infection, such as chikungunya, Venezuelan equine encephalitis, dengue, influenza, and zika.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with a viral infection, in particular, chikungunya, Venezuelan equine encephalitis, dengue, influenza, and zika. Thus, provided is a method comprising administering a therapeutically effective amount of a composition comprising a disclosed compound to a subject. In a further aspect, the method can be a method for treating a viral infection.

a. Treating a Viral Infection

In one aspect, disclosed are methods of treating a viral infection in a subject having the viral infection, the method comprising the step of administering to the subject a therapeutically effective amount of at least one disclosed compound, or a pharmaceutically acceptable salt thereof.

In one aspect, disclosed are methods for the treatment of a viral infection in a subject having the viral infection, the method comprising the step of administering to the subject a therapeutically effective amount of at least one compounds having a structure represented by a formula:

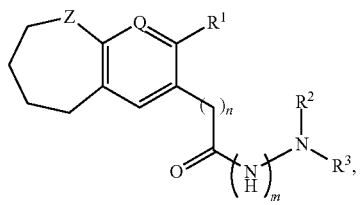

wherein each of m and n is independently selected from 0 and 1; wherein Q is selected from CH and N; wherein Z is selected from NH and CH$_2$; wherein R$^1$ is selected from hydrogen, —OH, C1-C4 alkyl, C1-C4 haloalkoxy, and C1-C4 alkoxy; wherein R$^2$ is hydrogen; and wherein R$^3$ is C2-C5 heteroaryl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar$^1$, and Ar$^1$; wherein Ar$^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein R$^3$ is a structure represented by a formula:

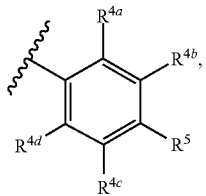

wherein each of R$^{4a}$, R$^{4b}$, R$^{4c}$, and R$^{4d}$ is independently selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4) (C1-C4) dialkylamino, and Ar$^2$; wherein Ar$^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein R$^5$ is selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, —(C1-C4 alkyl)CO$_2$H, and Ar$^3$; and wherein Ar$^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of R$^2$ and R$^3$ are covalently bonded together and, together with the intermediate atoms, comprise a 3- to 6-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and R$^1$ is hydrogen, then R$^3$ is not pyridinyl, provided that when n is 1, then R$^5$ is not hydrogen, or provided that when R$^5$ is hydrogen, then R$^1$ is not hydrogen, or a pharmaceutically acceptable salt thereof.

In one aspect, disclosed are methods for the treatment of a viral infection in a subject having the viral infection, the method comprising the step of administering to the subject a therapeutically effective amount of at least one compound having a structure represented by a formula:

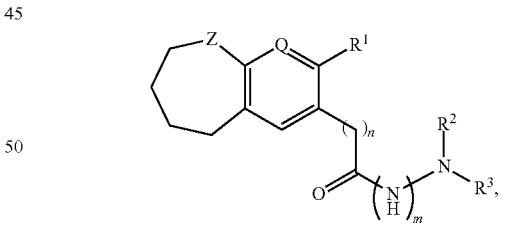

wherein each of m and n is independently selected from 0 and 1; wherein Q is selected from CH and N; wherein Z is selected from NH and CH$_2$; wherein R$^1$ is selected from hydrogen, —OH, C1-C4 alkyl, C1-C4 haloalkoxy, and C1-C4 alkoxy; wherein R$^2$ is hydrogen; and wherein R$^3$ is C2-C5 heteroaryl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4) (C1-C4) dialkylamino, (C1-C4 alkyl)Ar$^1$, and Ar$^1$; wherein Ar$^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein $R^3$ is a structure represented by a formula:

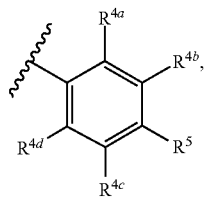

wherein each of $R^{4a}$, $R^{4b}$, $R^{4c}$, and $R^{4d}$ is independently selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and $Ar^2$; wherein $Ar^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; wherein $R^5$ is selected from hydrogen, halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and $Ar^3$; and wherein $Ar^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl; or wherein each of $R^2$ and $R^3$ are covalently bonded together and, together with the intermediate atoms, comprise a 3- to 6-membered heterocycloalkyl substituted with 0, 1, 2, or 3 groups independently selected from halogen, —CN, —NH$_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino; provided that when n is 1 and $R^1$ is hydrogen, then $R^3$ is not pyridinyl, provided that when n is 1, then $R^5$ is not hydrogen, or provided that when $R^5$ is hydrogen, then $R^1$ is not hydrogen, or a pharmaceutically acceptable salt thereof.

Examples of viral infections include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika.

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the viral infection.

In a further aspect, the disorder is associated with a viral infection. In a still further aspect, the viral infection is selected from human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika. In yet a further aspect, the viral infection is selected from chikungunya, Venezuelan equine encephalitis, dengue, influenza, and zika.

In a further aspect, the method further comprises the step of administering a therapeutically effective amount of at least one antiviral agent. In a still further aspect, the at least one agent is selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscamet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Inhibiting a Viral Infection in a Mammal

In one aspect, disclosed are methods of inhibiting a viral infection in a mammal, the method comprising the step of administering to the mammal a therapeutically effective amount of at least one disclosed compound, or a pharmaceutically acceptable salt thereof.

In a further aspect, the compound exhibits inhibition of a viral infection. In a still further aspect, the compound exhibits a decrease in a viral infection. In yet a further aspect, the viral infection is CHIKV.

In a further aspect, the compound exhibits inhibition of CHIKV activity with an EC$_{50}$ of less than about 30 μM. In a still further aspect, the compound exhibits inhibition of CHIKV activity with an EC$_{50}$ of less than about 25 μM. In yet a further aspect, the compound exhibits inhibition of CHIKV activity with an EC$_{50}$ of less than about 20 μM. In an even further aspect, the compound exhibits inhibition of CHIKV activity with an EC$_{50}$ of less than about 15 μM. In a still further aspect, the compound exhibits inhibition of CHIKV activity with an EC$_{50}$ of less than about 10 μM. In yet a further aspect, the compound exhibits inhibition of CHIKV activity with an EC$_{50}$ of less than about 5 μM. In an even further aspect, the compound exhibits inhibition of CHIKV activity with an EC$_{50}$ of less than about 1 μM. In a still further aspect, the compound exhibits inhibition of CHIKV activity with an EC$_{50}$ of less than about 0.5 μM.

In a further aspect, the subject is a mammal. In a still further aspect, the subject is a human.

In a further aspect, the subject has been diagnosed with a need for treatment of the disorder prior to the administering step. In a still further aspect, the method further comprises the step of identifying a subject in need of treatment of the disorder.

3. Methods of Inhibiting a Viral Infection in at Least One Cell

In one aspect, disclosed are methods for inhibiting a viral infection in at least one cell, the method comprising the step of contacting the at least one cell with an effective amount of at least one disclosed compound, or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

4. Use of Compounds

In one aspect, the invention relates to the use of a disclosed compound or a product of a disclosed method. In a further aspect, a use relates to the manufacture of a medicament for the treatment of a viral infection in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a viral infection in a subject. Also disclosed is the use of a compound for antagonism of a viral infection. In one aspect, the use is characterized in that the subject is a human. In one aspect, the use is characterized in that the disorder is a viral infection.

In a further aspect, the use relates to the manufacture of a medicament for the treatment of a viral infection in a subject.

In a further aspect, the use relates to antagonism of a viral infection in a subject. In a further aspect, the use relates to modulating viral activity in a subject. In a still further aspect, the use relates to modulating viral activity in a cell. In yet a further aspect, the subject is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a viral infection in a mammal. In a further aspect, the viral infection is selected from chikungunya, Venezuelan equine encephalitis, dengue, influenza, and zika.

5. Manufacture of a Medicament

In one aspect, the invention relates to a method for the manufacture of a medicament for treating a viral infection in a subject having the viral infection, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of a viral infection. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, disclosed are kits comprising at least one disclosed compound and one or more of: (a) at least one antiviral agent; (b) a instructions for administering the at least one compound in connection with treating a viral infection; (c) instructions for administering the at least one compound in connection with reducing the risk of viral infection; and (d) instructions for treating a viral infection.

In a further aspect, the viral infection is selected from human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika. In a still further aspect, the viral infection is selected from chikungunya, Venezuelan equine encephalitis, dengue, influenza, and zika.

In a still further aspect, the antiviral agent is selected from selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure.

Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals

A. General Experimental

The reactions were performed under a dry argon atmosphere and reaction temperatures were measured externally. Anhydrous solvents over molecular sieves were purchased from Aldrich and used as such in reactions. Purification of compounds was performed on an Isco Teledyne Combiflash Rf200 with four channels to carryout sequential purification. Universal RediSep solid sample loading pre-packed cartridges (5.0 g Silica) were used to absorb crude product and purified on 12 g silica RediSep Rf Gold Silica (20-40 μm spherical silica) columns using appropriate solvent gradients. Pure samples were dried overnight under high vacuum over $P_2O_5$ at 78° C. before analyses. The reactions were monitored by thin-layer chromatography (TLC) on pre-coated silica gel ($60F_{254}$) aluminium plates (0.25 mm) from E. Merck and visualized using UV light (254 nm). Pure samples were dried overnight under high vacuum over $P_2O_5$ at 78° C. before analyses. The HR-mass spectral data were obtained on an Agilent LC-MSTOF by electrospray ionization (ESI). $^1$H NMR spectra were recorded at 400 MHz on Agilent/Varian MR-400 spectrometer in $CDCl_3$ or DMSO-$d_6$ as solvents. The chemical shifts (δ) are in ppm downfield from standard tetramethylsilane (TMS). Coupling constants (J) are reported in Hertz (Hz). Purity of final compounds was checked by HPLC using Waters HPLC equipped with a 3100 Mass Detector using Sunfire C18 column (5 μm, 4.6×150 mm) using Acetonitrile-$H_2O$ (both containing 0.1% formic acid) 10-90% in 15 min.

b. Synthesis of Compound Nos. 1, 4-6, 8-12, 14, 15, 18-20, 24-26, 34, and 35

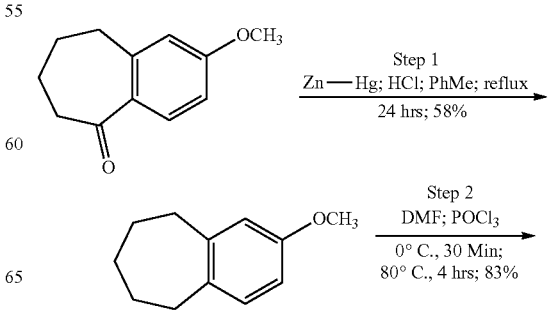

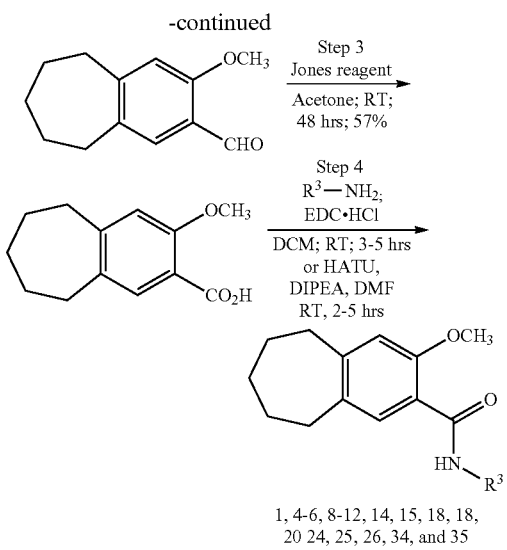

i. Step 1: Preparation of 2-methoxy-6,7,8,9-tetrahydro-5H-benzo[7]annulene

To a mixture of zinc (121 g, 1.86 mol) and mercury(II) chloride (11.42 g, 42 mmol) was added a solution of HCl [9.2 mL in 256 mL of deionized $H_2O$]. The reaction mixture was stirred at room temperature for 10 min and decanted. The resulted slurry was suspended in an aqueous solution of HCl [230 mL in 101 mL deionized water] and added toluene (130 mL) followed by 2-methoxy-6,7,8,9-tetrahydro-5H-benzo[7]annulen-5-one (16 g, 84 mmol). The reaction mixture was refluxed for 24h at 110° C. It was cooled to room temperature and poured into ice-cold water (1 L). The resulting mixture was extracted with EtOAc. The organic layer was dried over $Na_2SO_4$, filtered and solvent was evaporated. The crude residue was purified on a pre-packed Silica gel column using Teledyne ISCO flash chromatographic system by Hexanes:EtOAc (19:1). Yield: 8.60 g (58%). $^1$H NMR (400 MHz, $CDCl_3$) δ 7.03 (d, J=8.2 Hz, 1H), 6.71 (d, J=2.7 Hz, 1H), 6.64 (dd, J=8.2, 2.7 Hz, 1H), 3.80 (s, 3H), 2.77 (dd, J=11.0, 6.4 Hz, 4H), 1.84 (d, J=5.5 Hz, 2H), 1.66 (dd, J=12.9, 5.3 Hz, 4H).

ii. Step 2: Preparation of 3-methoxy-6,7,8,9-tetrahydro-5H-benzo[7]annulene-2-carbaldehyde DMF (2.62 mL, 33.92 mmol) and $POCl_3$ (2.88 mL, 30.96 mmol) were mixed at 0° C. under nitrogen atmosphere and stirred at same temperature for 30 min. 2-Methoxy-6,7,8,9-tetrahydro-5H-benzo[7]annulene (2.6 g, 14.76 mmol) was added to the above reaction mixture and heated at 80° C. for 4 hours. The reaction was diluted with ice-cold water and extracted with EtOAc. The organic layer was dried over anhydrous $Na_2SO_4$, filtered and concentrated under reduced pressure. The crude residue was purified on a pre-packed Silica gel column using Teledyne ISCO flash chromatographic system by Hexanes:EtOAc (19:1). Yield: 2.5 g (83%). $^1$H NMR (400 MHz, $CDCl_3$) δ 10.36 (s, 1H), 7.52 (s, 1H), 6.72 (s, 1H), 3.88 (s, 3H), 2.76 (ddd, J=19.8, 6.9, 4.1 Hz, 4H), 1.96-1.73 (m, 2H), 1.62 (ddd, J=21.5, 10.7, 5.5 Hz, 4H).

iii. Step 3: Preparation of 3-methoxy-6,7,8,9-tetrahydro-5H-benzo[7]annulene-2-carboxylic acid 3-Methoxy-6,7,8,9-tetrahydro-5H-benzo[7]annulene-2-carbaldehyde (900 mg, 4.4 mmol) was dissolved in 5 mL of acetone and to this solution, Jones reagent (2 mL, 26.4 mmol) was added at room temperature. The reaction mixture was stirred at room temperature for 24 h and after completion of the reaction, it was diluted with water and extracted with EtOAc. The organic layer was washed with brine and dried over anhydrous $Na_2SO_4$, filtered and concentrated under reduced pressure. The crude residue was purified on a pre-packed Silica gel column using Teledyne ISCO flash chromatographic system by Hexanes:EtOAc (6:4). Yield: 554 mg (57%). $^1$H NMR (400 MHz, $CDCl_3$) δ 10.83 (s, 1H), 7.83 (s, 1H), 6.78 (s, 1H), 4.02 (s, 3H), 2.77 (ddd, J=17.6, 6.9, 4.1 Hz, 4H), 1.80 (p, J=5.9 Hz, 2H), 1.61 (ddd, J=19.6, 10.2, 4.9 Hz, 4H).

IV. Step 4: General Amide Coupling Procedure

Product from Step-3 (1 mmol) was dissolved in 5 mL of anhydrous $CH_2Cl_2$. To this solution, corresponding amine (1.1 mmol) was added followed by EDC (2.2 mmol) and the reaction mixture was stirred for 2-3 h at room temperature. The reaction mixture was diluted with water and extracted with $CH_2Cl_2$. The organic layer was dried over anhydrous $Na_2SO_4$ and solvent was evaporated. The crude product was purified on a pre-packed Silica gel column using Teledyne ISCO flash chromatographic system.

(i) N-(4-(tert.-butyl)phenyl)-3-methoxy-6,7,8,9-tetrahydro-5H-benzo[7]annulene-2-carboxamide (1)

Yield: 15.7 mg (58%). $^1$H NMR ($CDC_3$) δ 7.99 (s, 1H), 7.68-7.45 (m, 2H), 7.46-7.28 (m, 2H), 6.77 (s, 1H), 4.01 (s, 3H), 2.94-2.60 (m, 4H), 1.93-1.75 (m, 2H), 1.65 (dt, J=9.8, 4.9 Hz, 4H), 1.32 (s, 9H). HR-ESIMS: m/z 352.2198 $[M+H]^+$ calcd for $C_{23}H_{30}NO_2$, found 352.2271. HPLC Purity: 100% (Retention Time=19.08 min).

(ii) N-(1-(tert.-butyl)-5-methyl-1H-pyrazol-3-yl)-3-methoxy-6,7,8,9-tetrahydro-5H-benzo[7]annulene-2-carboxamide (4)

Yield: 26.5 mg (63%). $^1$H NMR (400 MHz, $CDCl_3$) δ 9.94 (s, 1H), 7.97 (s, 1H), 6.74 (s, 1H), 6.61 (s, 1H), 4.00 (s, 3H), 3.00-2.64 (m, 4H), 2.44 (s, 3H), 2.25-1.00 (m, 15H). HR-ESIMS: m/z 356.2260 $[M+H]^+$ calcd for $C_{21}H_{30}N_3O_2$, found 356.23358. HPLC Purity: 97.3% (Retention Time=17.8 min).

(iii) N-(1-ethyl-5-methyl-1H-pyrazol-3-yl)-3-methoxy-6,7,8,9-tetrahydro-5H-benzo[7]annulene-2-carboxamide (5)

Yield: 12.5 mg (37.5%). $^1$H NMR (400 MHz, $CDCl_3$) δ 10.00 (s, 1H), 7.98 (s, 1H), 6.74 (s, 1H), 6.62 (s, 1H), 4.13-3.71 (m, 5H), 2.92-2.62 (m, 4H), 2.28 (d, J=0.6 Hz, 3H), 1.83 (s, 2H), 1.75-1.59 (m, 4H), 1.38 (t, J=7.2 Hz, 3H). HR-ESIMS: m/z 328.1947 $[M+H]^+$ calcd for $C_{19}H_{26}N_3O_2$, found 328.20196. HPLC Purity: 98.2% (Retention Time=15.9 min).

(iv) N-(1-ethyl-5-methyl-3-(trifluoromethyl)-1H-pyrazol-4-yl)-3-methoxy-6,7,8,9-tetrahydro-5H-benzo[7]annulene-2-carboxamide (6)

Yield: 28.2 mg (61%). $^1$H NMR (400 MHz, $CDCl_3$) δ 9.38 (s, 1H), 7.96 (s, 1H), 6.79 (s, 1H), 4.23-4.07 (m, 2H), 3.99 (s, 3H), 2.92-2.65 (m, 4H), 2.28 (s, 3H), 1.83 (d, J=5.3 Hz, 2H), 1.75-1.58 (m, 4H), 1.46 (t, J=7.3 Hz, 3H). HR- ESIMS: m/z 396.1821 [M+H]+ calcd for $C_{20}H_{25}F_3N_3O_2$, found 396.1898. HPLC Purity: 97.1% (Retention Time=17.2 min).

(v) N-(5-(tert.-butyl)thiazol-2-yl)-3-methoxy-6,7,8,9-tetrahydro-5H-benzo[7]annulene-2-carboxamide (8)

Yield: 27.1 mg (66%). $^1$H NMR (400 MHz, CDCl$_3$) δ 10.93 (s, 1H), 7.99 (s, 1H), 7.13 (d, J=0.7 Hz, 1H), 6.78 (s, 1H), 4.22-3.73 (m, 3H), 3.09-2.41 (m, 4H), 1.83 (d, J=5.3 Hz, 2H), 1.65 (dt, J=10.8, 5.1 Hz, 4H), 1.40 (d, J=0.7 Hz, 9H). HR-ESIMS: m/z 359.1715 [M+H]+ calcd for $C_{20}H_{27}N_2O_2S$, found 359.1787. HPLC Purity: 98.4% (Retention Time=20.4 min).

(vi) N-(2-(tert.-butyl)thiazol-5-yl)-3-methoxy-6,7,8,9-tetrahydro-5H-benzo[7]annulene-2-carboxamide (9)

Yield: 22.6 mg (55%). $^1$H NMR (400 MHz, CDCl$_3$) δ 10.31 (s, 1H), 7.98 (s, 1H), 7.42 (s, 1H), 6.78 (s, 1H), 4.04 (s, 3H), 3.07-2.48 (m, 4H), 1.83 (d, J=5.4 Hz, 2H), 1.75-1.53 (m, 4H), 1.40 (d, J=31.3 Hz, 9H). HR-ESIMS: m/z 359.1715 [M+H]+ calcd for $C_{20}H_{27}N_2O_2S$, found 359.1779. HPLC Purity: 97.3% (Retention Time=17.8 min).

(vii) N-(4-(2-hydroxypropan-2-yl)phenyl)-3-methoxy-6,7,8,9-tetrahydro-5H-benzo[7]annulene-2-carboxamide (10)

Yield: 23.3 mg (51%). $^1$H NMR (400 MHz, CDCl$_3$) δ 9.80 (s, 1H), 7.99 (s, 1H), 7.63 (d, J=8.7 Hz, 2H), 7.47 (d, J=8.6 Hz, 2H), 6.77 (s, 1H), 4.02 (d, J=1.1 Hz, 3H), 2.95-2.63 (m, 4H), 1.83 (d, J=5.5 Hz, 2H), 1.77-1.60 (m, 4H), 1.59 (d, J=0.8 Hz, 6H). HR-ESIMS: m/z 354.1991 [M+H]+ calcd for $C_{22}H_{28}NO_3$, found 354.2065. HPLC Purity: 97.2% (Retention Time=16 min).

(viii) N-(5-(tert.-butyl)pyridin-2-yl)-3-methoxy-6,7,8,9-tetrahydro-5H-benzo[7]annulene-2-carboxamide (11)

Yield: 24.6 mg (61%). $^1$H NMR (400 MHz, CDCl$_3$) δ 10.30 (s, 1H), 8.47-8.21 (m, 2H), 7.98 (s, 1H), 7.73 (ddd, J=8.7, 2.6, 0.4 Hz, 1H), 6.78 (s, 1H), 4.04 (s, 3H), 2.92-2.68 (m, 4H), 1.84 (t, J=5.7 Hz, 2H), 1.73-1.63 (m, 4H), 1.34 (s, 9H). HR-ESIMS: m/z 353.2151 [M+H]+ calcd for $C_{22}H_{29}N_2O_2$, found 353.2219. HPLC Purity: 99.5% (Retention Time=20.5 min).

(ix) N-(4-(1,1,1,3,3,3-hexafluoro-2-hydroxypropan-2-yl)phenyl)-3-methoxy-6,7,8,9-tetrahydro-5H-benzo[7]annulene-2-carboxamide (12)

Yield: 23.8 mg (45%). $^1$H NMR (400 MHz, CDCl$_3$) δ 9.95 (s, 1H), 7.98 (s, 1H), 7.88-7.47 (m, 4H), 6.78 (s, 1H), 4.04 (s, 3H), 2.95-2.63 (m, 4H), 1.84 (d, J=5.2 Hz, 2H), 1.64 (d, J=4.9 Hz, 4H). HR-ESIMS: m/z 462.1426 [M+H]+ calcd for $C_{22}H_{22}F_6NO_3$, found 462.1491. HPLC Purity: 99.3% (Retention Time=18.7 min).

(x) 3-methoxy-N-(4-(trifluoromethoxy)phenyl)-6,7,8,9-tetrahydro-5H-benzo[7]annulene-2-carboxamide (14)

Yield: 25.8 mg (68%). $^1$H NMR (400 MHz, CDCl$_3$) δ 7.98 (s, 1H), 7.83-7.53 (m, 2H), 7.26-7.01 (m, 2H), 6.78 (s, 1H), 4.03 (s, 3H), 3.05-2.58 (m, 4H), 1.95-1.77 (m, 2H), 1.80-1.58 (m, 4H). HR-ESIMS: m/z 380.1395 [M+H]+ calcd for $C_{20}H_{21}F_3NO_3$, found 380.1456. HPLC Purity: 99.5% (Retention Time=20.29 min).

(xi) N-([1,1'-biphenyl]-4-yl)-3-methoxy-6,7,8,9-tetrahydro-5H-benzo[7]annulene-2-carboxamide (15)

Yield: 40.4 mg (65%). $^1$H NMR (400 MHz, CDCl$_3$) δ 9.89 (s, 1H), 8.01 (s, 1H), 7.87-7.68 (m, 2H), 7.70-7.49 (m, 4H), 7.44 (t, J=7.8 Hz, 2H), 7.39-7.26 (m, 1H), 6.79 (s, 1H), 4.05 (s, 3H), 3.09-2.57 (m, 4H), 1.84 (d, J=5.6 Hz, 2H), 1.66 (dd, J=9.0, 4.7 Hz, 4H). HR-ESIMS: m/z 372.1885 [M+H]+ calcd for $C_{25}H_{26}NO_2$, found 372.1953. HPLC Purity: 95.2% (Retention Time=20.7 min).

(xii) N-(4-(tert.-butyl)benzyl)-3-methoxy-6,7,8,9-tetrahydro-5H-benzo[7]annulene-2-carboxamide (18)

Yield: 28.3 mg (71%). $^1$H NMR (400 MHz, CDCl$_3$) δ 8.17 (s, 1H), 7.96 (s, 1H), 7.44-7.30 (m, 2H), 7.29-7.25 (m, 2H), 6.71 (s, 1H), 4.65 (d, J=5.7 Hz, 2H), 3.89 (s, 3H), 2.93-2.60 (m, 4H), 1.89-1.72 (m, 2H), 1.73-1.55 (m, 4H), 1.55-0.99 (m, 9H). HR-ESIMS: m/z 366.2355 [M+H]+ calcd for $C_{24}H_{32}NO_2$, found 366.2418. HPLC Purity: 97.9% (Retention Time=20.21 min).

(xiii) N-(4-(1H-pyrazol-3-yl)phenyl)-3-methoxy-6,7,8,9-tetrahydro-5H-benzo[7]annulene-2-carboxamide (19)

Yield: 17.2 mg (21%). $^1$H NMR (400 MHz, CDCl$_3$) δ 9.91 (s, 1H), 7.95 (s, 1H), 7.86-7.56 (m, 4H), 7.57 (dd, J=2.2, 0.6 Hz, 1H), 6.76 (s, 1H), 6.55 (d, J=2.1 Hz, 1H), 4.02 (s, 3H), 2.95-2.64 (m, 4H), 1.81 (d, J=5.3 Hz, 2H), 1.63 (dt, J=9.5, 5.1 Hz, 4H). HR-ESIMS: m/z 362.1790 [M+H]+ calcd for $C_{22}H_{24}N_3O_2$, found 362.1861. HPLC Purity: 99.8% (Retention Time=15.9 min).

(xiv) N-(4-(1,1-dioxidoisothiazolidin-2-yl)phenyl)-3-methoxy-6,7,8,9-tetrahydro-5H-benzo[7]annulene-2-carboxamide (20)

Yield: 8.9 mg (81%). $^1$H NMR (400 MHz, CDCl$_3$) δ 7.98 (s, 1H), 7.85-7.50 (m, 2H), 7.27 (d, J=8.9 Hz, 2H), 6.77 (s, 1H), 4.02 (s, 3H), 3.77 (t, J=6.6 Hz, 2H), 3.51-3.27 (m, 2H), 2.99-2.65 (m, 4H), 2.53 (dd, J=7.9, 7.0 Hz, 2H), 1.83 (s, 2H), 1.75-1.58 (m, 4H). HR-ESIMS: m/z 415.1613 [M+H]+ calcd for $C_{22}H_{27}N_2O_4S$, found 415.1689. HPLC Purity: 98.3% (Retention Time=15.8 min).

(xv) N-(4-(2-cyanopropan-2-yl)phenyl)-3-methoxy-6,7,8,9-tetrahydro-5H-benzo[7]annulene-2-carboxamide (24)

Yield: 90 mg (73%). $^1$H NMR (400 MHz, CDCl$_3$) δ 9.85 (s, 1H), 7.97 (s, 1H), 7.83-7.51 (m, 2H), 7.57-7.26 (m, 2H), 6.77 (s, 1H), 4.02 (s, 3H), 2.97-2.61 (m, 4H), 2.06-1.33 (m, 12H). HR-ESIMS: m/z 363.1994 [M+H]+ calcd for $C_{23}H_{27}N_2O_2$, found 363.2067. HPLC Purity: 99.1% (Retention Time=18.3 min).

(xvi) 3-methoxy-N-(5-phenyl-1H-pyrazol-3-yl)-6,7,8,9-tetrahydro-5H-benzo[7]annulene-2-carboxamide (25)

Yield: 70 mg (43%). $^1$H NMR (400 MHz, CDCl$_3$) δ 12.87 (s, 1H), 10.17 (s, 1H), 7.94-7.51 (m, 3H), 7.56-7.17 (m, 3H), 7.00 (s, 2H), 3.95 (s, 3H), 2.78 (dd, J=23.8, 10.4 Hz, 4H), 1.78 (s, 2H), 1.74-1.21 (m, 4H). HR-ESIMS: m/z 362.1790 [M+H]⁺ calcd for $C_{22}H_{24}N_3O_2$, found 362.1869. HPLC Purity: 99% (Retention Time=18.51 min).

(xvii) N-(5-(tert.-butyl)-1H-pyrazol-3-yl)-3-methoxy-6,7,8,9-tetrahydro-5H-benzo[7]annulene-2-carboxamide (26)

Yield: 78 mg (51%). ¹H NMR (400 MHz, CDCl₃) δ 10.16 (s, 1H), 7.97 (s, 1H), 6.74 (s, 1H), 6.56 (s, 1H), 3.93 (s, 3H), 3.24-2.48 (m, 4H), 1.81 (d, J=5.4 Hz, 2H), 1.64 (dt, J=9.3, 5.0 Hz, 4H), 1.33 (s, 9H). HR-ESIMS: m/z 342.2103 [M+H]⁺ calcd for $C_{20}H_{28}N_3O_2$, found 342.2180. HPLC Purity: 99.3% (Retention Time=15.4 min).

(xviii) 3-methoxy-N-(2-(methylthio)pyridin-3-yl)-6,7,8,9-tetrahydro-5H-benzo[7]annulene-2-carboxamide (34)

Yield: 45 mg (29%). ¹H NMR (400 MHz, CDCl₃) δ 10.20 (s, 1H), 8.65 (dd, J=8.1, 1.5 Hz, 1H), 8.24 (dd, J=4.7, 1.6 Hz, 1H), 7.99 (s, 1H), 7.09 (ddd, J=8.1, 4.7, 0.4 Hz, 1H), 6.80 (s, 1H), 4.11 (s, 3H), 3.11-2.34 (m, 6H), 1.84 (q, J=6.1 Hz, 2H), 1.79-1.58 (m, 5H). HR-ESIMS: m/z 343.1402 [M+H]⁺ calcd for $C_{19}H_{23}N_2O_2S$, found 343.1479. HPLC Purity: 99.4% (Retention Time=19 min).

(xix) N-(1-ethyl-1H-pyrazol-3-yl)-3-methoxy-6,7,8,9-tetrahydro-5H-benzo[7]annulene-2-carboxamide (35)

Yield: 50 mg (69%). ¹H NMR (400 MHz, CDCl₃) δ 10.38 (s, 1H), 8.92 (s, 2H), 8.41 (s, 1H), 6.69 (s, 1H), 3.92 (s, 3H), 2.78 (dd, J=18.2, 10.9 Hz, 3H), 1.82 (s, 2H), 1.64 (s, 3H), 1.42 (s, 7H). HR-ESIMS: m/z 314.1790 [M+H]⁺ calcd for $C_{18}H_{24}N_3O_2$, found 315.1812. HPLC Purity: 99.4% (Retention Time=15.8 min).

c. Synthesis of N-(4-(tert.-butyl)phenyl)-3-hydroxy-6,7,8,9-tetrahydro-5H-benzo[7]annulene-2-carboxamide (2)

N-(4-(tert.-butyl)phenyl)-3-methoxy-6,7,8,9-tetrahydro-5H-benzo[7]annulene-2-carboxamide (70 mg, 0.199 mmol) was dissolved in dry dichloromethane and to this solution, BBr₃ (0.075 mL, 0.797 mmol) was added dropwise at −78° C. under nitrogen atmosphere. After 15 min at −78° C., temperature raised to 0° C. and stirred for additional 2 h. The reaction was quenched with addition of 2 mL MeOH, concentrated under reduced pressure, diluted with water (50 mL) and extracted with CH₂C2 (2×50) mL. The organic layer was dried over anhydrous Na₂SO₄ and solvent was evaporated under reduced pressure. The crude product was purified on a pre-packed Silica gel column using Teledyne ISCO flash chromatographic system by Hexanes:EtOAc (8:2). Yield: 52.8 g (77%). ¹H NMR (400 MHz, CDCl₃): δ 11.88 (s, 1H), 7.83 (s, 1H), 7.48 (d, J=8.8 Hz, 2H), 7.40 (d, J=8.8 Hz, 2H), 7.19 (s, 1H), 6.78 (s, 1H), 2.76 (dt, J=7.3, 3.9 Hz, 4H), 1.83 (s, 2H), 1.76-1.57 (m, 4H), 1.33 (s, 9H). HR-ESIMS: m/z 338.2042 [M+H]⁺ calcd for $C_{22}H_{28}NO_2$, found 338.2111. HPLC Purity: 98.3% (Retention Time=21.1 min).

d. Synthesis of N-(4-(tert.-butyl)phenyl)-6,7,8,9-tetrahydro-5H-benzo[7]annulene-2-carboxamide (3)

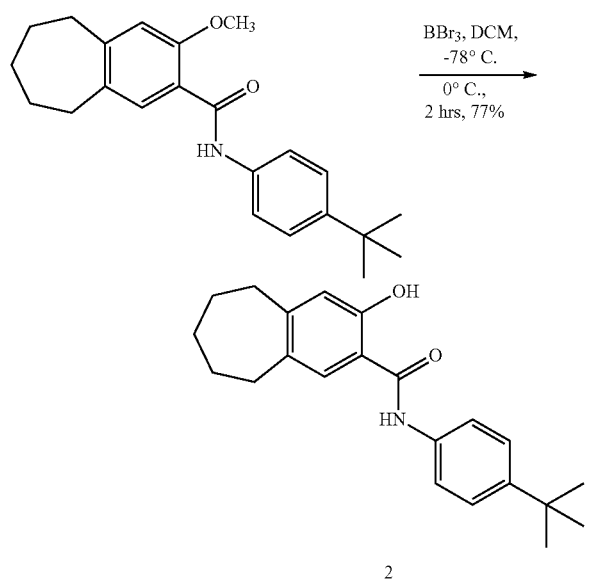

i. Step 1: Preparation of 6,7,8,9-tetrahydro-5H-benzo[7]annulen-2-yl trifluoromethane-sulfonate 6,7,8,9-Tetrahydro-5H-benzo[7]annulen-2-ol (2 g, 12.33 mmol) was dissolved in 9 mL dry dichloromethane. To this solution, pyridine (1.95 g, 24.66 mmol) was added under nitrogen atmosphere followed by drop wise addition of trifluoro-methanesulfonic anhydride (3.83 g, 13.56 mmol) at 0-5° C. The reaction mixture was stirred for 90 min at the same temperature. The reaction mixture was diluted with 1M HCl and extracted with dichloromethane. The organic layer was washed with aq. NaHCO$_3$, brine and concentrated. The crude product was purified on a pre-packed Silica gel column using Teledyne ISCO flash chromatographic system by Hexanes:EtOAc (19:1). Yield: (3.1 g, 87%). $^1$H NMR (400 MHz, CDCl$_3$): δ 7.13 (d, J=8.2 Hz, 1H), 7.06-6.81 (m, 2H), 2.97-2.58 (m, 4H), 1.84 (q, J=6.1 Hz, 2H), 1.65 (dt, J=11.0, 5.7 Hz, 4H).

ii. Step 2: Preparation of 6,7,8,9-tetrahydro-5H-benzo[7]annulene-2-carbonitrile 6,7,8,9-Tetrahydro-5H-benzo[7]annulen-2-yl trifluoromethanesulfonate (200 mg, 0.68 mmol) was dissolved in dry DMF under argon and to this solution, added dicyanozinc (47.9 mg, 0.408 mmol) followed by tetrakis(triphenylphosphine)palladium(0) (79 mg, 0.068 mmol). The reaction mixture was heated at 130° C. for 3 h, diluted with water and extracted with EtOAc. The organic layer was washed with ice-cold water (50×3 mL), followed by brine and dried over anhydrous Na$_2$SO$_4$. The organic layer was concentrated under reduced pressure followed by purification of crude product on a pre-packed Silica gel column using Teledyne ISCO flash chromatographic system by Hexanes:EtOAc (9:1). Yield: (82.6 mg, 71%). $^1$H NMR (400 MHz, CDCl$_3$) δ 7.40-7.33 (m, 1H), 7.16 (dd, J=14.9, 8.2 Hz, 1H), 7.06-6.93 (m, 1H), 2.95-2.66 (m, 4H), 1.84 (dt, J=5.9, 3.1 Hz, 2H), 1.76-1.54 (m, 4H).

iii. Step 3: Preparation of 6,7,8,9-tetrahydro-5H-benzo[7]annulene-2-carboxylic acid 6,7,8,9-Tetrahydro-5H-benzo[7]annulene-2-carbonitrile (82.6 mg, 0.48 mmol) was dissolved in HBr (3 mL):AcOH (1 mL). The reaction mixture was heated overnight. The reaction mixture was neutralized with the slow addition of 1N NaOH to pH=7-8. It was extracted with EtOAc, organic layer dried over anhydrous Na$_2$SO$_4$, filtered and concentrated under reduced pressure. Crude product was purified on a pre-packed Silica gel column using Teledyne ISCO flash chromatographic system by Hexanes:EtOAc (7:3). Yield: (60 mg, 65%). $^1$H NMR (400 MHz, CDCl$_3$) δ 7.92-7.74 (m, 2H), 7.19 (d, J=8.4 Hz, 1H), 2.96-2.65 (m, 4H), 1.86 (t, J=5.6 Hz, 2H), 1.77-1.52 (m, 4H).

iv. Step 4: Preparation of N-(4-(tert.-butyl)phenyl)-6,7,8,9-tetrahydro-5H-benzo[7]annulene-2-carboxamide (3)

6,7,8,9-Tetrahydro-5H-benzo[7]annulene-2-carboxylic acid (30 mg, 0.158 mmol) was dissolved in dry DCM and to this solution, 4-(tert.-butyl)aniline (25.9 mg, 0.173 mmol) was added followed by EDC (66.5 mg, 0.347 mmol). The reaction mass was stirred at room temperature for 3 h, after completion of reaction, it was diluted with water and extracted with DCM. The organic layer was dried over anhydrous Na$_2$SO$_4$, filtered, concentrated under reduced pressure. The crude product was purified on a pre-packed Silica gel column using Teledyne ISCO flash chromatographic system by Hexanes:EtOAc (9:1). Yield: 32.3 mg (63%). $^1$H NMR (400 MHz, CDCl$_3$) δ 7.80 (s, 1H), 7.61 (d, J=1.9 Hz, 1H), 7.56 (dd, J=8.2, 2.4 Hz, 3H), 7.41-7.35 (m, 2H), 7.18 (d, J=7.8 Hz, 1H), 2.97-2.74 (m, 4H), 1.89-1.79 (m, 2H), 1.64 (d, J=14.8 Hz, 4H), 1.39-1.26 (m, 9H). HR-ESIMS: m/z 322.2093 [M+H]$^+$ calcd for C$_{22}$H$_{28}$NO, found 323.2163. HPLC Purity: 99.2% (Retention Time=19.7 min).

e. Synthesis of N-(5-(tert.-butyl)thiophen-2-yl)-3-methoxy-6,7,8,9-tetrahydro-5H-benzo[7]annulene-2-carboxamide (7)

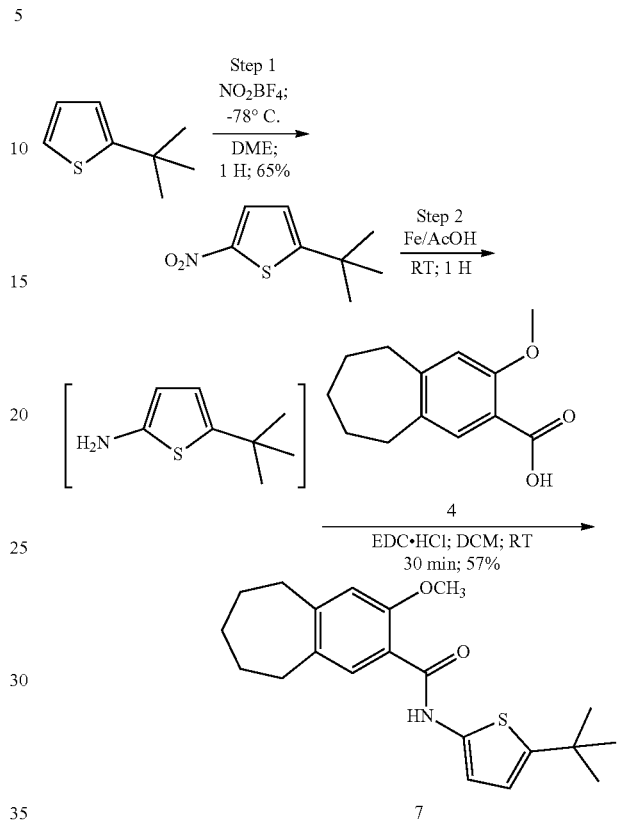

i. Step 1: Preparation of 2-(tert.-butyl)-5-nitrothiophene

Nitronium tetrafluoroborate (178 mg, 1.34 mmol) was taken in an oven dried vial and placed at −78° C. under nitrogen atmosphere. Dry 1,2-dimethoxyethane (2 mL) was added to the vial and stirred at the same temperature for 5 mins. To the above solution, 2-(tert.-butyl)thiophene (250 mg, 1.78 mmol) in 1 mL of 1,2-dimethoxyethane was added dropwise and the reaction mass was stirred at −78° C. for additional 1 h. Water was added to the reaction mixture and extracted with dichloromethane. The organic layer was dried over anhydrous Na$_2$SO$_4$, filtered and concentrated under reduced pressure. The crude product was purified on a pre-packed Silica gel column using Teledyne ISCO flash chromatographic system by 100% Hexanes. Yield: (215 mg, 65%). $^1$H NMR (400 MHz, CDCl$_3$) δ 7.77 (d, J=4.2 Hz, 1H), 6.82 (d, J=4.2 Hz, 1H), 1.41 (d, J=1.3 Hz, 9H).

ii. Steps 2 and 3: Preparation of N-(5-(tert.-butyl)thiophen-2-yl)-3-methoxy-6,7,8,9-tetrahydro-5H-benzo[7]annulene-2-carboxamide (7)

2-(tert.-Butyl)-5-nitrothiophene (50 mg, 0.27 mmol) was dissolved in AcOH (5 mL) and to this solution was added Fe powder (15.07 mg, 0.27 mmol). The reaction mass was stirred at room temperature for 30 min, filtered through short pad of celite and washed with EtOAc. The filtrate was diluted with aq. NaHCO$_3$ and extracted with EtOAc. The organic layer was dried over anhydrous Na$_2$SO$_4$, filtered and concentrated under reduced pressure. This crude amino intermediate was immediately used for coupling reaction. This crude amino intermediate was dissolved in 3 mL dry dichloromethane and to this solution was added 3-methoxy-6,7,8,9-tetrahydro-5H-benzo[7]annulene-2-carboxylic acid (59.5 mg, 0.270 mmol) followed by EDC (114 mg, 0.594 mmol). The reaction mass was stirred at room temperature for 1 h. After completion of reaction, the crude product was directly loaded on a pre-packed Silica gel column. Purified using Teledyne ISCO flash chromatographic system by Hexanes:EtOAc (19:1). Yield: 55.6 mg (57%). $^1$H NMR (400 MHz, CDCl$_3$) δ 10.28 (s, 1H), 8.01 (s, 1H), 6.76 (s, 1H), 6.59 (d, J=3.8 Hz, 1H), 6.52 (d, J=3.8 Hz, 1H), 4.02 (s, 3H), 2.81 (dt, J=7.5, 4.3 Hz, 4H), 1.83-1.83 (m, 2H), 1.70-1.58 (m, 4H), 1.39 (s, 9H). HR-ESIMS: m/z 358.1762 [M+H]$^+$ calcd for C$_2$H$_{28}$NO$_2$S, found 358.1836. HPLC Purity: 99.2% (Retention Time=20.7 min).

f. Synthesis of N-(5-(tert.-butyl)-3-cyanothiophen-2-yl)-3-methoxy-6,7,8,9-tetrahydro-5H-benzo[7]annulene-2-carboxamide (13)

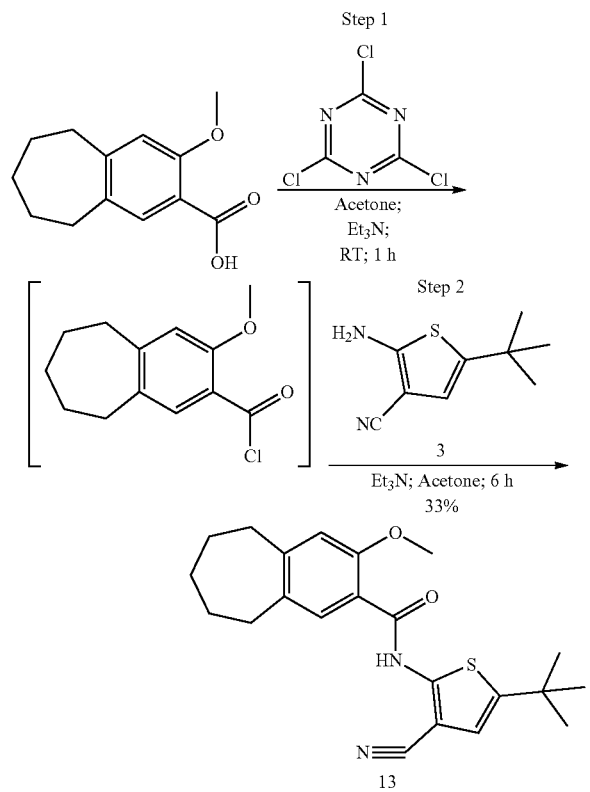

3-Methoxy-6,7,8,9-tetrahydro-5H-benzo[7]annulene-2-carboxylic acid (25 mg, 0.113 mmol) was dissolved in acetone and to this solution, 2,4,6-trichloro-1,3,5-triazine (41.9 mg, 0.227 mmol) was added under nitrogen. The reaction mass was stirred for 30 min at room temperature. TLC indicated formation of acid chloride and at this point, 2-amino-5-(tert.-butyl)thiophene-3-carbonitrile (20.46 mg, 0.113 mmol) was added followed by 1 eq. of triethylamine. The reaction mass was stirred for 6 h at room temperature. The reaction mixture was filtered, diluted with water and extracted with dichloromethane. The organic layer was dried over anhydrous Na$_2$SO$_4$, filtered and concentrated under reduced pressure. The crude product was purified on a pre-packed Silica gel column using Teledyne ISCO flash chromatographic system by Hexanes:EtOAc (8:2). Yield: 15 mg (33%). $^1$H NMR (400 MHz, CDCl$_3$) δ 11.41 (s, 1H), 7.98 (s, 1H), 6.81 (s, 1H), 6.67 (d, J=0.9 Hz, 1H), 4.12 (s, 3H), 3.08-2.58 (m, 4H), 1.94-1.77 (m, 2H), 1.76-1.57 (m, 4H), 1.38 (s, 9H). HR-ESIMS: m/z 383.1715 [M+H]$^+$ calcd. for C$_{22}$H$_{27}$N$_2$O$_2$S, found 383.1775. HPLC Purity: 95% (Retention Time=19.3 min).

g. Synthesis of 3-methoxy-N-(5-phenylpyridin-2-yl)-6,7,8,9-tetrahydro-5H-benzo[7]annulene-2-carboxamide (16)

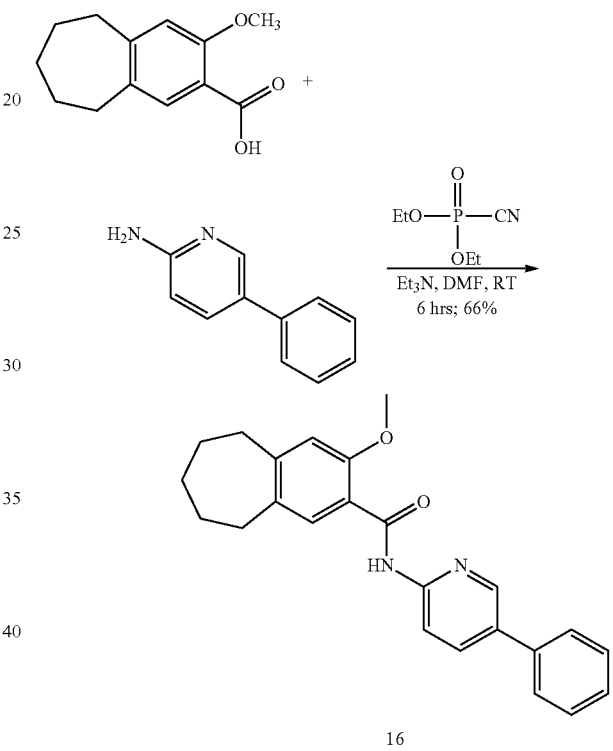

3-Methoxy-6,7,8,9-tetrahydro-5H-benzo[7]annulene-2-carboxylic acid (25 mg, 0.113 mmol) was dissolved in DMF and to this solution, diethyl phosphorocyanidate (18.51 mg, 0.113 mmol) was added followed by Et$_3$N (0.016 mL, 0.113 mmol). The reaction mass was stirred at room temperature for 10 min. After which, 5-phenylpyridin-2-amine (23.18 mg, 0.136 mmol) was added to the reaction mass and it was again stirred for 6 hours. The reaction mixture was diluted with 1N HCl and extracted with EtOAc. The organic layer was dried over anhydrous Na$_2$SO$_4$, filtered and concentrated under reduced pressure followed by purification on a pre-packed Silica gel column using Teledyne ISCO flash chromatographic system by Hexanes:EtOAc (7:3). Yield: 28.5 mg (66%). $^1$H NMR (400 MHz, CDCl$_3$) δ 10.43 (s, 1H), 8.63-8.37 (m, 2H), 8.00 (s, 2H), 7.68-7.53 (m, 2H), 7.47 (t, J=7.7 Hz, 2H), 7.38 (s, 1H), 6.80 (s, 1H), 4.19-3.83 (m, 3H), 2.97-2.65 (m, 4H), 1.85 (s, 2H), 1.75-1.58 (m, 4H). HR-ESIMS: m/z 373.1838 [M+H]$^+$ calcd for C$_{24}$H$_{25}$N$_2$O$_2$, found 373.1904. HPLC Purity: 99.9% (Retention Time=20.5 min).

h. Synthesis of N-(4-(tert.-butyl)phenyl)-3-(difluoromethoxy)-6,7,8,9-tetrahydro-5H-benzo[7]annulene-2-carboxamide (17)

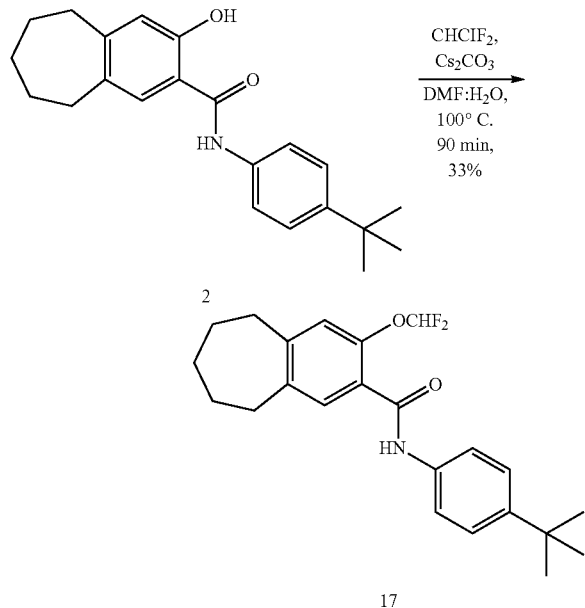

N-(4-(tert.-Butyl)phenyl)-3-hydroxy-6,7,8,9-tetrahydro-5H-benzo[7]annulene-2-carboxamide (22.00 mg, 0.065 mmol) was dissolved in DMF and H₂O (3:1). To this solution, Cs₂CO₃ (21.24 mg, 0.065 mmol) was added followed by the addition of 2-chloro-2,2-difluoroacetic acid (19.56 mg, 0.15 mmol), and the reaction mass was heated at 100° C. for 90 min. After completion of reaction, it was diluted with aq. NH₄Cl and extracted with EtOAc. The organic layer was dried over anhydrous Na₂SO₄, filtered concentrated under reduced pressure. The crude product was purified on a pre-packed Silica gel column using Teledyne ISCO flash chromatographic system by Hexanes:EtOAc (8:2). Yield: 8.42 mg (33%). ¹H NMR (400 MHz, CDCl₃): δ 8.81 (s, 1H), 7.92 (s, 1H), 7.67-7.47 (m, 2H), 7.47-7.29 (m, 2H), 6.90 (s, 1H), 6.50 (d, J=73.2 Hz, 1H), 2.83 (t, J=11.2 Hz, 4H), 1.98-1.78 (m, 2H), 1.77-1.54 (m, 4H), 1.32 (s, 9H). HR-ESIMS: m/z 388.2010 [M+H]⁺ calcd for C₂₃H₂₈F₂NO₂, found 388.2083. HPLC Purity: 99.3% (Retention Time=20.3 min).

i. Synthesis of N-(4-(tert.-butyl)phenyl)-3-ethoxy-6,7,8,9-tetrahydro-5H-benzo[7]annulene-2-carboxamide (21)

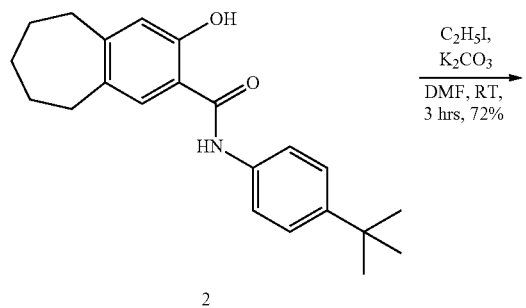

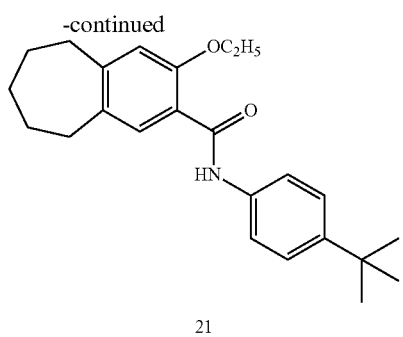

N-(4-(tert.-butyl)phenyl)-3-hydroxy-6,7,8,9-tetrahydro-5H-benzo[7]annulene-2-carboxamide (47 mg, 0.139 mmol) was dissolved in dry DMF (5 mL) and to this solution added iodoethane (0.012 mL, 0.153 mmol) under nitrogen atmosphere followed by the addition of K₂CO₃ (42.3 mg, 0.306 mmol). The reaction mixture was stirred at room temperature for 3 h. After completion, the reaction was diluted with water and extracted with EtOAc. The organic layer was dried over anhydrous Na₂SO₄, filtered, concentrated under reduced pressure followed by purification on a pre-packed Silica gel column using Teledyne ISCO flash chromatographic system by Hexanes:EtOAc (19:1). Yield: 36.7 mg (72%). ¹H NMR (400 MHz, CDCl₃): δ 10.08 (s, 1H), 8.00 (s, 1H), 7.73-7.46 (m, 2H), 7.49-7.27 (m, 2H), 6.74 (s, 1H), 4.24 (q, J=7.0 Hz, 2H), 3.04-2.41 (m, 4H), 1.82 (d, J=5.4 Hz, 2H), 1.61 (dt, J=13.9, 7.7 Hz, 7H), 1.32 (s, 9H). HR-ESIMS: m/z 366.2355 [M+H]⁺ calcd for C₂₄H₃₂NO₂, found 366.2427. HPLC Purity: 98.7% (Retention Time=21.8 min).

j. Synthesis of N-(4-(tert.-butyl)phenyl)-3-ethyl-6,7,8,9-tetrahydro-5H-benzo[7]annulene-2-carboxamide (22)

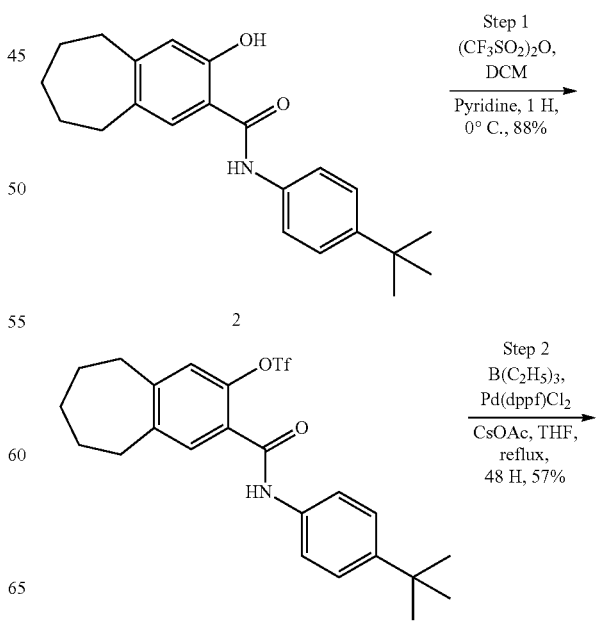

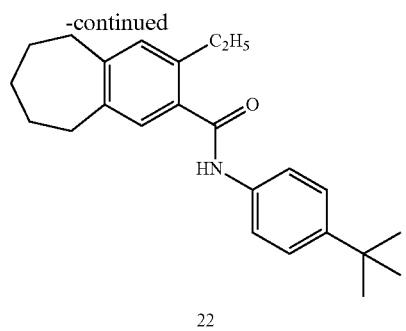

22 k. Synthesis of Compounds Nos. 23 and 27

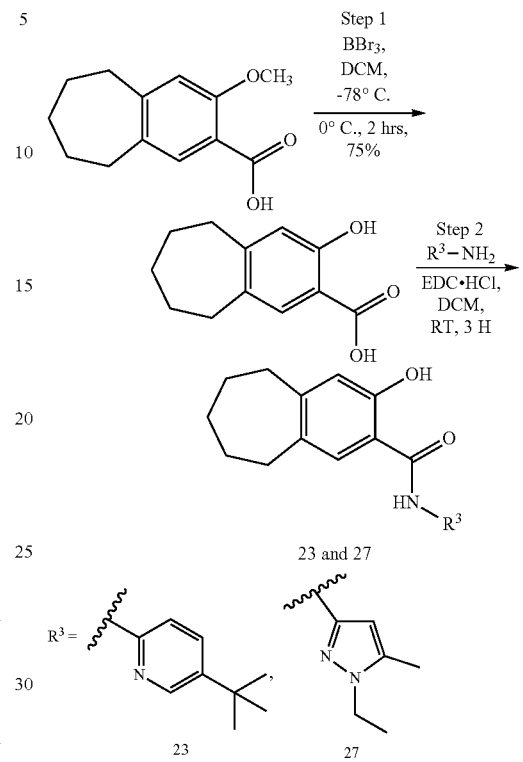

i. Step 1: Preparation of 3-((4-(tert.-butyl)phenyl)carbamoyl)-6,7,8,9-tetrahydro-5H-benzo[7]annulen-2-yl trifluoromethanesulfonate N-(4-(tert.-butyl)phenyl)-3-hydroxy-6,7,8,9-tetrahydro-5H-benzo[7]annulene-2-carboxamide (50 mg, 0.148 mmol) was dissolved in 3 mL dry dichloromethane and to this solution, under nitrogen atmosphere, added trifluoromethanesulfonic anhydride (41.8 mg, 0.148 mmol) drop wise at 0-5° C. The reaction mixture was stirred for 1 h at the same temperature. After completion of the reaction, it was diluted with 1M HCl and extracted with dichloromethane. The organic layer was washed with aq. NaHCO$_3$ followed by brine and dried over Na$_2$SO$_4$. The organic layer was concentrated and the crude product was purified on a pre-packed Silica gel column using Teledyne ISCO flash chromatographic system by Hexanes:EtOAc (19:1). Yield: 61.2 mg (88%). $^1$H NMR (400 MHz, CDCl$_3$) δ 8.16 (s, 1H), 7.97-7.72 (m, 2H), 7.64-7.41 (m, 2H), 7.04 (s, 1H), 2.97-2.61 (m, 4H), 1.84 (d, J=5.1 Hz, 2H), 1.66 (d, J=5.4 Hz, 4H), 1.45 (d, J=76.0 Hz, 9H). ESIMS: m/z 470.1 [M+H]$^+$.

ii. Step 2: preparation of N-(4-(tert.-butyl)phenyl)-3-ethyl-6,7,8,9-tetrahydro-5H-benzo[7]annulene-2-carboxamide (22)

3-((4-(tert.-Butyl)phenyl)carbamoyl)-6,7,8,9-tetrahydro-5H-benzo[7]annulen-2-yl trifluoromethanesulfonate (47 mg, 0.1 mmol) was dissolved in dry THF and to this solution under nitrogen, cesium acetate (38.4 mg, 0.2 mmol) was added, followed by dichloro [1,1'-bis(diphenylphosphino) ferrocene] palladium(II), Pd (1.46 mg, 2.002 μmol) and triethylborane (0.2 mL 1M solution in THF). The reaction mixture was refluxed for 48 h. After completion of the reaction, it was diluted with water and extracted with EtOAc. The organic layer was dried over anhydrous Na$_2$SO$_4$, filtered and concentrated under reduced pressure. The crude product was purified on a pre-packed Silica gel column using Teledyne ISCO flash chromatographic system by Hexanes:EtOAc (19:1). Yield: 20 mg (57%). $^1$H NMR (400 MHz, CDCl$_3$) δ 7.53 (d, J=8.6 Hz, 2H), 7.39 (t, J=8.7 Hz, 2H), 7.19 (s, 1H), 7.02 (s, 1H), 3.02-2.40 (m, 6H), 1.96-1.76 (m, 2H), 1.65 (d, J=4.9 Hz, 4H), 1.32 (s, 9H), 1.24 (t, J=7.6 Hz, 3H). HR-ESIMS: m/z 350.2406[M+H]$^+$ calcd for C$_{24}$H$_{32}$NO, found 350.2472. HPLC Purity: 99.6% (Retention Time=20.5 min).

i. Step 1: preparation of 3-hydroxy-6,7,8,9-tetrahydro-5H-benzo[7]annulene-2-carboxylic acid 3-Methoxy-6,7,8,9-tetrahydro-5H-benzo[7]annulene-2-carboxylic acid (100 mg, 0.45 mmol) was dissolved in dry DCM and to this solution BBr$_3$ (1.35 mL, 1.35 mmol) was added dropwise at −78° C. under N$_2$ atmosphere. After 15 min at −78° C., reaction temperature was raised to 0° C. and stirred for additional 2 h. The reaction was quenched with MeOH (3 mL) and concentrated under reduced pressure. The crude material was diluted with 0.5 mL EtOAc and directly loaded on a pre-packed Silica gel column. Purified using Teledyne ISCO flash chromatographic system by Hexanes:EtOAc (1:1). Yield: 70.2 mg (75%): $^1$H NMR (400 MHz, CDCl$_3$): δ 7.58 (s, 1H), 6.71 (s, 1H), 3.16-2.19 (m, 4H), 2.13-1.67 (m, 2H), 1.80-1.29 (m, 4H).

ii. Step 2: General Procedure for Amide Coupling

3-Hydroxy-6,7,8,9-tetrahydro-5H-benzo[7]annulene-2-carboxylic acid (1 mmol) was dissolved in 3 mL of dry CH$_2$Cl$_2$ under inert atmosphere and to this solution, EDC.HCl (2.2 mmol) was added. The resulting mixture was stirred at room temperature for 10 min and at this point of time appropriate amine (1 mmol) was introduced to the reaction. The reaction mass was stirred at room temperature for 3 h. After completion of the reaction it was diluted with ice-cold water and extracted with CH$_2$C2. The organic layer was dried over anhydrous Na$_2$SO$_4$, filtered, concentrated under reduced pressure and purified.

(i) N-(5-(tert.-butyl)pyridin-2-yl)-3-hydroxy-6,7,8,9-tetrahydro-5H-benzo[7]annulene-2-carboxamide (23)

Purified on a pre-packed Silica gel column using Teledyne ISCO flash chromatographic system by Hexanes:EtOAc (8:2). Yield: 35 mg (60%). $^1$H NMR (400 MHz, CDCl$_3$): δ 11.94 (s, 1H), 8.95 (s, 1H), 8.34 (s, 1H), 8.23 (d, J=8.4 Hz, 1H), 7.78 (dd, J=8.7, 2.6 Hz, 1H), 7.37 (s, 1H), 6.78 (s, 1H), 2.75 (dt, J=7.2, 3.5 Hz, 4H), 1.82 (p, J=5.9 Hz, 2H), 1.74-1.55 (m, 4H), 1.36 (s, 9H). HR-ESIMS: m/z 339.1994 [M+H]$^+$ calcd for C$_{21}$H$_{27}$N$_2$O$_2$, found 339.2069. HPLC Purity: 98.9% (Retention Time=19.24 min).

(ii) N-(1-ethyl-5-methyl-1H-pyrazol-3-yl)-3-hydroxy-6,7,8,9-tetrahydro-5H-benzo[7]annulene-2-carboxamide (27)

Purified on a pre-packed Silica gel column using Teledyne ISCO flash chromatographic system by Hexanes:EtOAc (7:3). Yield: 13 mg (17%). $^1$H NMR (400 MHz, CDCl$_3$): δ 11.91 (s, 1H), 8.53 (s, 1H), 7.19 (s, 1H), 6.76 (s, 1H), 6.53 (s, 1H), 3.99 (q, J=7.3 Hz, 2H), 2.72 (ddd, J=17.7, 7.0, 4.0 Hz, 4H), 2.53-1.95 (m, 3H), 1.97-1.69 (m, 2H), 1.78-1.48 (m, 4H), 1.62-1.20 (m, 3H). HR-ESIMS: m/z 314.1790 [M+H]$^+$ calcd for C$_{18}$H$_{24}$N$_3$O$_2$, found 314.1865. HPLC Purity: 98.6% (Retention Time=15.05 min).

l. Synthesis of Compounds Nos. 28 and 29

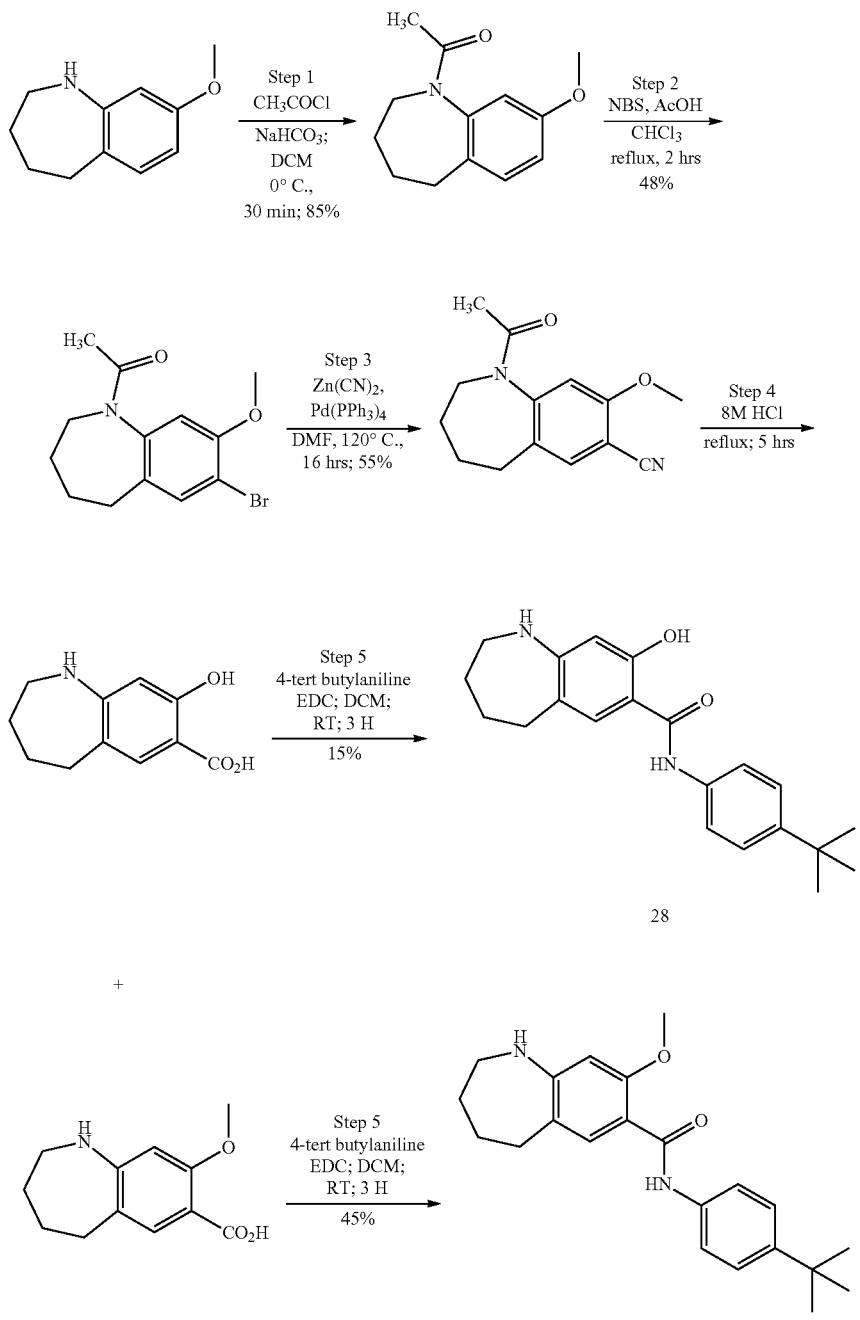

i. Step 1: Preparation of 1-(8-methoxy-2,3,4,5-tetrahydro-1H-benzo[b]azepin-1-yl)ethan-1-one 8-Methoxy-2,3,4,5-tetrahydro-1H-benzo[b]azepine (150 mg, 0.846 mmol) was dissolved in DCM under argon atmosphere. To this solution was added sodium bicarbonate (213 mg, 2.54 mmol) followed by the dropwise addition of acetyl chloride (66.3 mg, 0.845 mmol) at 0° C. The reaction mixture then stirred at room temperature for 30 min and then diluted with water. The reaction mixture was extracted with DCM, organic layer was dried over anhydrous $Na_2SO_4$, filtered and concentrated under reduced pressure. The crude product was used for next step without purification. $^1$H NMR (400 MHz, $CDCl_3$): δ 7.13 (d, J=8.3 Hz, 1H), 6.76 (dd, J=8.3, 2.7 Hz, 1H), 6.68 (d, J=2.7 Hz, 1H), 4.74-4.60 (m, 1H), 3.79 (s, 3H), 2.81-2.50 (m, 3H), 1.88 (s, 7H). ESIMS: m/z 220.1 [M+H]$^+$.

ii. Step 2: preparation of 1-(7-bromo-8-methoxy-2,3,4,5-tetrahydro-1H-benzo[b]azepin-1-yl)ethan-1-one 1-(8-Methoxy-2,3,4,5-tetrahydro-1H-benzo[b]azepin-1-yl)ethan-1-one (180 mg, 0.82 mmol) was dissolved in a mixture of 2 mL $CHCl_3$ and 0.2 mL AcOH under argon atmosphere. To this reaction mixture was added NBS (165 mg, 0.930 mmol) and the reaction mass was refluxed for 2 h. After completion of reaction, it was diluted with water and extracted with DCM. The organic layer was dried over anhydrous $Na_2SO_4$, filtered and concentrated under reduced pressure. The crude product was purified on a pre-packed Silica gel column using Teledyne ISCO flash chromatographic system by Hexanes:EtOAc (8:2). Yield: (117 mg, 48%): $^1$H NMR (400 MHz, $CDCl_3$): δ 7.42 (s, 1H), 6.68 (s, 1H), 3.86 (s, 3H), 2.64 (d, J=24.1 Hz, 4H), 1.91 (d, J=26.7 Hz, 7H). ESIMS: m/z 300.1 [M+2]+.

iii. Step 3: Preparation of 1-acetyl-8-methoxy-2,3,4,5-tetrahydro-1H-benzo[b]azepine-7-carbonitrile 1-(7-Bromo-8-methoxy-2,3,4,5-tetrahydro-1H-benzo[b]azepin-1-yl)ethanone (100 mg, 0.335 mmol) was dissolved in dry DMF under argon at room temperature and to this solution dicyanozinc (59.1 mg, 0.503 mmol) was added followed by tetrakis triphenylphosphine palladium(0) (3.88 mg, 3.35 µmol). The reaction mass was stirred at 120° C. for 16 hours. After completion of reaction quenched with water and extracted with EtOAc. The organic layer was washed with brine, dried over anhydrous $Na_2SO_4$, filtered and concentrated under reduced pressure. The crude product was purified on a pre-packed Silica gel column using Teledyne ISCO flash chromatographic system by 1:1 (Hexanes:EtOAc). Yield: 45 mg (55%): $^1$H NMR (400 MHz, $CDCl_3$): δ 7.46 (s, 1H), 6.76 (s, 1H), 3.92 (s, 3H), 2.77-2.51 (m, 3H), 1.90 (s, 6H), 1.25 (s, 2H). ESIMS: m/z 244.2 [M+H]$^+$.

iv. Step 4: Preparation of 8-hydroxy-2,3,4,5-tetrahydro-1H-benzo[b]azepine-7-carboxylic acid and 8-methoxy-2,3,4,5-tetrahydro-1H-benzo[b]azepine-7-carboxylic Acid 1-Acetyl-8-methoxy-2,3,4,5-tetrahydro-1H-benzo[b]azepine-7-carbonitrile (40 mg, 0.164 mmol) was dissolved in 8M HCl (4 mL) and refluxed for 5 hours. The reaction mixture was neutralized with 10% NaOH aq. solution and extracted with EtOAc. The organic layer was dried over anhydrous $Na_2SO_4$, filtered and concentrated under reduced pressure. The mixture of these two intermediates was inseparable and this mixture was used as such for next step.

v. Step 5: General Procedure of EDC Coupling

Crude product from Step-4 (1 mmol) was dissolved in 5 mL of anhydrous $CH_2Cl_2$. To this solution, corresponding amine (1.1 mmol) was added followed by EDC (2.2 mmol) and the reaction mixture was stirred for 2-3 h at room temperature. The reaction mixture was diluted with water and extracted with $CH_2Cl_2$. The organic layer was dried over anhydrous $Na_2SO_4$ and solvent was evaporated. The crude product was purified on a pre-packed Silica gel column using Teledyne ISCO flash chromatographic system.

(i) N-(4-(tert.-butyl)phenyl)-8-hydroxy-2,3,4,5-tetrahydro-1H-benzo[b]azepine-7-carboxamide (28)

Purified on 2000 µM normal phase preparative TLC plate using Hexanes:EtOAc (7:3). Yield: (8.3 mg, 15%): $^1$H NMR (400 MHz, $CDCl_3$): δ 7.64 (s, 1H), 7.52 (d, J=8.4 Hz, 2H), 7.38 (d, J=8.6 Hz, 2H), 6.30 (s, 1H), 3.14-3.03 (m, 2H), 2.76 (d, J=10.8 Hz, 2H), 1.79 (s, 2H), 1.70 (s, 2H), 1.35-1.28 (m, 9H). HR-ESIMS: m/z 339.1994 [M+H]$^+$ calcd for $C_{21}H_{27}N_2O_2$, found 339.2066. HPLC Purity: 96.7% (Retention Time=17.9 min).

(ii) N-(4-(tert.-butyl)phenyl)-8-methoxy-2,3,4,5-tetrahydro-1H-benzo[b]azepine-7-carboxamide (29)

Purified on 2000 µM normal phase preparative TLC plate using Hexanes:EtOAc (7:3). Yield: (26 mg, 45%). $^1$H NMR (400 MHz, $CDCl_3$) δ 8.08 (s, 1H), 7.80 (d, J=8.4 Hz, 2H), 7.53 (d, J=8.4 Hz, 2H), 6.48 (s, 1H), 3.88 (s, 3H), 3.13-2.95 (m, 2H), 2.75 (s, 2H), 1.90-1.76 (m, 2H), 1.66 (q, J=5.5 Hz, 2H), 1.37 (s, 9H). HR-ESIMS: m/z 353.2151 [M+H]$^+$ calcd for $C_{22}H_{29}N_2O_2$, found 353.2223. HPLC Purity: 99.4% (Retention Time=16.59 min).

m. Synthesis of N-(4-(tert.-butyl)phenyl)-3-methoxy-6,7,8,9-tetrahydro-5H-benzo[7]annulene-2-carbohydrazide(30)

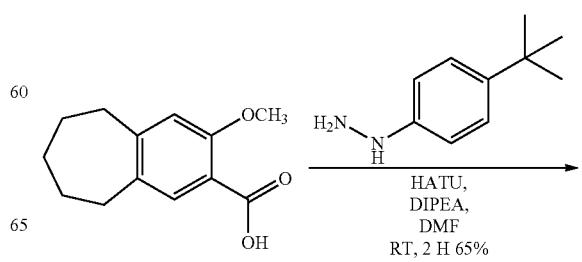

119

-continued

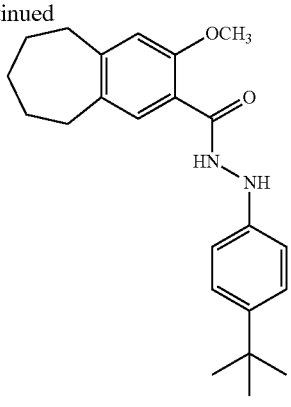

30

3-Methoxy-6,7,8,9-tetrahydro-5H-benzo[7]annulene-2-carboxylic acid (75 mg, 0.34 mmol) was dissolved in 3 mL dry DMF under inert atmosphere and to this solution, HATU (193.8 mg, 0.51 mmol) was added followed by the addition of DIPEA (0.177 mL, 1.02 mmol). The reaction mixture was stirred at room temperature for 10 mins and at this point of time, (4-(tert.-butyl)phenyl)hydrazine (61.3 mg, 0.374 mmol) was introduced to the reaction. The reaction mixture was stirred at room temperature for 2 h. The reaction was diluted with ice-cold water, aqueous layer was extracted with EtOAc. Organic layer was dried over anhydrous $Na_2SO_4$, filtered and concentrated under reduced pressure. The crude product was purified on a pre-packed Silica gel column using Teledyne ISCO flash chromatographic system by Hexanes:EtOAc (8:2). Yield: 81 mg (65%): $^1$H NMR (400 MHz, $CDCl_3$): δ 9.41 (s, 1H), 7.90 (s, 1H), 7.35-7.13 (m, 2H), 6.97-6.80 (m, 2H), 6.77 (s, 1H), 3.99 (s, 3H), 2.80 (ddd, J=13.4, 7.0, 4.1 Hz, 4H), 2.02-1.73 (m, 2H), 1.77-1.35 (m, 4H), 1.27 (s, 9H). HR-ESIMS: m/z 367.2307 $[M+H]^+$ calcd for $C_{23}H_{31}N_2O_2$, found 367.2386. HPLC Purity: 99.4% (Retention Time=18.98 min).

n. Synthesis of Compound Nos. 31-33

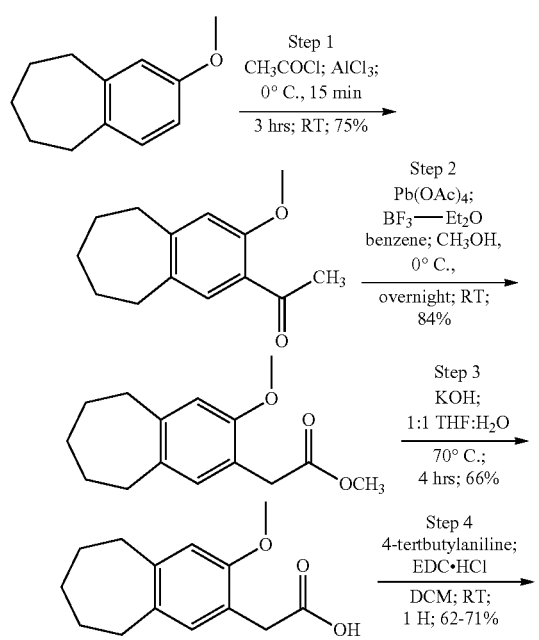

120

-continued

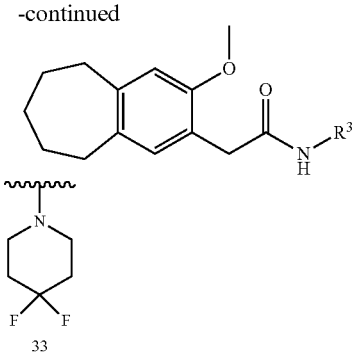

i. Step 1: Preparation of 1-(3-methoxy-6,7,8,9-tetra-hydro-5H-benzo[7]annulen-2-yl)ethan-1-one Acetyl chloride (151 μL, 2.128 mmol) was slowly added to a solution of aluminum trichloride (284 mg, 2.128 mmol) in 5 mL dry DCM at 0° C. After stirring at the same temperature for 15 min, 2-methoxy-6,7,8,9-tetrahydro-5H-benzo[7]annulene (250 mg, 1.418 mmol) in 3 mL anhydrous DCM was added dropwise to the reaction mixture. The reaction mixture was stirred at RT for 3 h. The reaction mixture was poured in to ice-cold water and extracted with DCM. The organic layer was washed with brine, dried over anhydrous $Na_2SO_4$, filtered and concentrated under reduced pressure. The crude product was purified on a pre-packed Silica gel column using Teledyne ISCO flash chromatographic system by Hexanes:EtOAc (19:1). Yield: 75 mg (65%). $^1$H NMR (400 MHz, $CDCl_3$) 7.51 (s, 1H), 6.71 (s, 1H), 3.88 (s, 3H), 3.07-2.59 (m, 4H), 2.58 (s, 3H), 2.06-1.18 (m, 6H). ESIMS: m/z 219.1 $[M+H]^+$.

ii. Step 2: Preparation of Methyl 2-(3-methoxy-6,7,8,9-tetrahydro-5H-benzo[7]annulen-2-yl)acetate To a suspension of lead tetraacetate (942 mg, 2.125 mmol) in benzene (5 mL) was added a solution of 1-(3-methoxy-6,7,8,9-tetrahydro-5H-benzo[7]annulen-2-yl)ethanone (300 mg, 1.374 mmol) in 0.5 MeOH followed by the drop wise addition of $BF_3.OEt_2$ (0.92 ml, 7.26 mmol) under $N_2$ atmosphere, at 0° C. The reaction mixture was stirred at room temperature overnight. The reaction mixture was quenched with ice-cold water and extracted with EtOAc. The organic layer was dried over anhydrous $Na_2SO_4$ filtered and concentrated under reduced pressure. The crude product was purified on a pre-packed Silica gel column using Teledyne ISCO flash chromatographic system by Hexanes:EtOAc (19:1). Yield: 188 mg (55%). $^1$H NMR (400 MHz, $CDCl_3$) 6.90 (s, 1H), 6.64 (s, 1H), 3.79 (s, 3H), 3.69 (s, 3H), 3.57 (s, 2H), 2.73 (ddd, J=17.9, 7.1, 3.9 Hz, 4H), 1.82 (p, J=5.9 Hz, 2H), 1.72-1.55 (m, 4H).

iii. Step 3: Preparation of 2-(3-methoxy-6,7,8,9-tetrahydro-5H-benzo[7]annulen-2-yl)acetic Acid Methyl 2-(3-methoxy-6,7,8,9-tetrahydro-5H-benzo[7]annulen-2-yl)acetate (188 mg, 0.757 mmol) was dissolved in THF:$H_2O$ (1:1) and to this solution at room temperature was added KOH (127 mg, 2.271 mmol) powder. The reaction mass was heated at 70° C. for 6 h. After completion of reaction, it was neutralized to pH=6 using 1M HCl and subsequently compound precipitated out. The solid was filtered, washed with water (10 mL) and dried under vacuum. Yield: (117 mg, 66%). $^1$H NMR (400 MHz, CDCl$_3$) δ 6.91 (s, 1H), 6.66 (s, 1H), 3.81 (s, 3H), 3.60 (s, 2H), 2.73 (ddd, J=19.1, 7.0, 4.0 Hz, 4H), 1.80 (d, J=5.5 Hz, 2H), 1.74-1.47 (m, 4H).

iv. Step 4: General Procedure for EDC Coupling Reactions 2-(3-Methoxy-6,7,8,9-tetrahydro-5H-benzo[7]annulen-2-yl)acetic acid (1 mmol) was dissolved in dry CH$_2$Cl$_2$, under inert atmosphere to this solution EDC.HCl (2.2 mmol) was added. The resulting mixture was stirred at room temperature for 10 min. The appropriate amine (1.1 mmol) was introduced to the reaction and the reaction mass was stirred at room temperature until completion (monitored by TLC). After completion of the reaction, it was diluted with ice-cold water and extracted with CH$_2$C2. The organic layer was dried over anhydrous Na$_2$SO$_4$, filtered and concentrated under reduced pressure. The crude product was purified on a pre-packed Silica gel column using Teledyne ISCO flash chromatographic system.

(i) N-(4-(tert.-butyl)phenyl)-2-(3-methoxy-6,7,8,9-tetrahydro-5H-benzo[7]annulen-2-yl)acetamide (31)

Purification on a pre-packed Silica gel column using Teledyne ISCO flash chromatographic system by Hexanes: EtOAc (19:1). Yield: (66%): $^1$H NMR (400 MHz, CDCl$_3$): δ 7.87-7.57 (m, 2H), 7.57-7.32 (m, 2H), 7.06 (s, 1H), 6.66 (s, 1H), 4.57 (d, J=5.7 Hz, 2H), 3.85 (s, 3H), 2.74 (dd, J=19.1, 10.9 Hz, 4H), 1.96-1.71 (m, 2H), 1.60 (s, 4H), 1.32 (s, 9H). HR-ESIMS: m/z 366.2355 [M+H]$^+$ calcd for C$_{24}$H$_{32}$NO$_2$, found 366.2422. HPLC Purity: 98.15% (Retention Time=19.3 min).

(ii) 1-(4-(tert.-butyl)piperidin-1-yl)-2-(3-methoxy-6,7,8,9-tetrahydro-5H-benzo[7]annulen-2-yl)ethan-1-one (32)

Purification on a pre-packed Silica gel column using Teledyne ISCO flash chromatographic system by Hexanes: EtOAc (1:1). Yield: (62%): $^1$H NMR (400 MHz, CDCl$_3$): δ 6.94 (s, 1H), 6.62 (s, 1H), 4.80-4.65 (m, 1H), 3.99-3.83 (m, 1H), 3.80 (s, 3H), 3.71-3.53 (m, 2H), 2.92-2.64 (m, 4H), 2.44 (s, 1H), 1.88-1.48 (m, 8H), 1.16 (dd, J=8.8, 2.8 Hz, 4H), 0.81 (s, 9H). HR-ESIMS: m/z 358.2668 [M+H]$^+$ calcd for C23H$_{36}$NO$_2$, found 358.2163. HPLC Purity: 98.7% (Retention Time=20.3 min).

(iii) 1-(4,4-difluoropiperidin-1-yl)-2-(3-methoxy-6,7,8,9-tetrahydro-5H-benzo[7]annulen-2-yl)ethan-1-one (33)

Purification on a pre-packed Silica gel column using Teledyne ISCO flash chromatographic system by Hexanes: EtOAc (7:3). Yield: 22.9 mg, (53%): $^1$H NMR (400 MHz, CDCl$_3$): δ 6.95 (s, 1H), 6.63 (s, 1H), 3.80 (s, 3H), 3.78-3.67 (m, 2H), 3.66 (s, 2H), 3.62-3.50 (m, 2H), 2.72 (ddd, J=20.9, 7.0, 3.9 Hz, 4H), 2.03-1.47 (m, 1OH). HR-ESIMS: m/z 338.1853 [M+H]$^+$ calcd for C$_{19}$H$_{26}$F$_2$NO$_2$, found 338.1921. HPLC Purity: 97.5% (Retention Time=16.2 min).

o. Synthesis of Compound Nos. 36-40

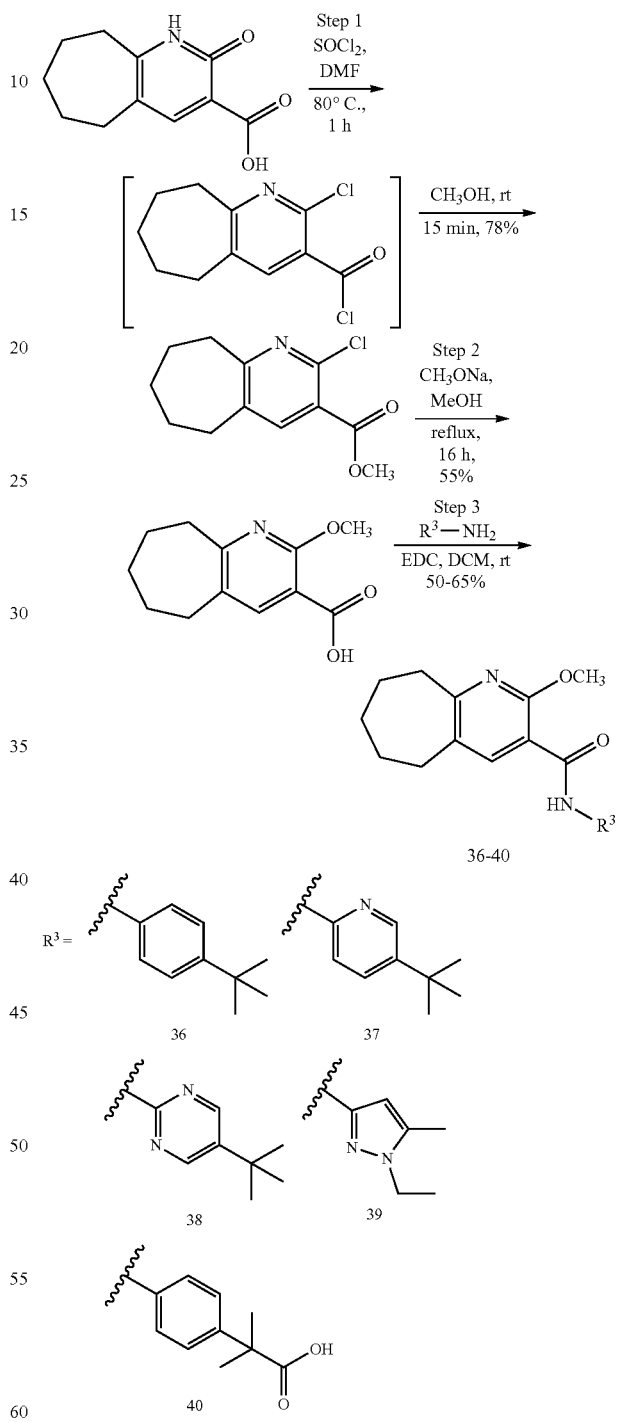

i. Step 1: Preparation of methyl 2-chloro-6,7,8,9-tetrahydro-5H-cyclohepta[b]pyridine-3-carboxylate 2-Oxo-2,5,6,7,8,9-hexahydro-1H-cyclohepta[b]pyridine-3-carboxylic acid (650 mg, 3.14 mmol) was dissolved in anhydrous DMF (0.243 mL, 3.14 mmol) and to it was added SOCl$_2$ (5.6 mL, 77 mmol). The reaction mass was heated at 80° C. for 1 hour, and after completion of reaction, concentrated under vacuo. To this crude mixture, 10 mL CH$_3$OH was added and stirred at room temperature for 15 mins and concentrated under reduced pressure. It was diluted with ice-cold water and extracted with DCM. The organic layer was dried over anhydrous Na$_2$SO$_4$, filtered and concentrated under reduced pressure. The crude product was purified on a pre-packed Silica gel column using Teledyne ISCO flash chromatographic system by Hexanes:EtOAc (9:1). Yield: (586 mg, 78%): $^1$H NMR (400 MHz, CDCl$_3$): δ 7.88 (s, 1H), 3.93 (s, 3H), 3.20-2.86 (m, 2H), 2.92-2.61 (m, 2H), 1.87 (d, J=5.5 Hz, 2H), 1.81-1.31 (m, 4H). ESIMS: m/z 240.6 [M+H]$^+$.

ii. Step 2: synthesis of 2-methoxy-6,7,8,9-tetrahydro-5H-cyclohepta[b]pyridine-3-carboxylic acid Methyl 2-chloro-6,7,8,9-tetrahydro-5H-cyclohepta[b]pyridine-3-carboxylate (500 mg, 2.086 mmol) was dissolved in MeOH under nitrogen atmosphere at room temperature. To this solution, sodium methanolate (0.954 mL, 16.69 mmol) (sodium methoxide, 25% wt. solution) was added drop wise and the reaction mixture was refluxed overnight. After completion of reaction, it was concentrated under reduced pressure, crude reaction mass quenched with 1N HCl to pH=4-5, subsequently compound precipitated out, filtered through cintered glass funnel, solid material dried under vaccuo, used for next step without further purification. Yield: (254 mg, 55%): $^1$H NMR (400 MHz, CDCl$_3$): δ 8.12 (s, 1H), 4.15 (s, 3H), 3.43-2.54 (m, 4H), 2.14-1.75 (m, 2H), 1.66 (dt, J=18.8, 5.3 Hz, 4H). ESIMS: m/z 222.2 [M+H]$^+$.

iii. Step 3: General Procedure for EDC Coupling Reactions

2-Methoxy-6,7,8,9-tetrahydro-5H-cyclohepta[b]pyridine-3-carboxylic acid (1 mmol) was dissolved in anhydrous CH$_2$Cl$_2$ under inert atmosphere and to this was added EDC.HCl (2.2 mmol). The resulting mixture was stirred at room temperature for 10 min and at this point of time appropriate aniline (1.1 mmol) was introduced to the reaction. The reaction mass was stirred at room temperature until its completion (monitored by TLC). After completion of the reaction, it was diluted with ice-cold water and extracted with CH$_2$Cl$_2$. The organic layer was dried over anhydrous Na$_2$SO$_4$, filtered and concentrated under reduced pressure followed by purification.

(i) N-(4-(tert.-butyl)phenyl)-2-methoxy-6,7,8,9-tetrahydro-5H-cyclohepta[b]pyridine-3-carboxamide (36)

Purification on a pre-packed Silica gel column using Teledyne ISCO flash chromatographic system by Hexanes:EtOAc (7:3). Yield: 26.3 mg, 33%. $^1$H NMR (400 MHz, CDCl$_3$): δ 9.79 (s, 1H), 8.25 (s, 1H), 7.71-7.48 (m, 2H), 7.52-7.28 (m, 2H), 4.14 (s, 3H), 3.06-2.87 (m, 2H), 2.88-2.64 (m, 2H), 1.87 (d, J=5.4 Hz, 2H), 1.79-1.55 (m, 4H), 1.32 (s, 9H). HR-ESIMS: m/z 353.2151 [M+H]$^+$ calcd for C$_{22}$H$_{29}$N$_2$O$_2$, found 353.2220. HPLC Purity: 99.4% (Retention Time=21.6 min).

(ii) N-(5-(tert.-butyl)pyridin-2-yl)-2-methoxy-6,7,8,9-tetrahydro-5H-cyclohepta[b]pyridine-3-carboxamide (37)

Purification on a pre-packed Silica gel column using Teledyne ISCO flash chromatographic system by Hexanes:EtOAc (6:4). Yield: 22.4 mg, 31%. $^1$H NMR (400 MHz, CDCl$_3$): δ 10.32 (s, 1H), 8.55-8.05 (m, 3H), 7.85-7.54 (m, 1H), 3.08-2.87 (m, 2H), 2.90-2.64 (m, 2H), 1.86 (q, J=6.0 Hz, 2H), 1.68 (ddd, J=22.3, 10.9, 5.3 Hz, 4H), 1.34 (s, 9H). HR-ESIMS: m/z 354.2103 [M+H]$^+$ calcd for C$_{21}$H$_{28}$N$_3$O$_2$, found 354.2178. HPLC Purity: 99.24% (Retention Time=21.18 min).

(iii) N-(5-(tert.-butyl)pyrimidin-2-yl)-2-methoxy-6,7,8,9-tetrahydro-5H-cyclohepta[b]pyridine-3-carboxamide (38)

Purification on a pre-packed Silica gel column using Teledyne ISCO flash chromatographic system by Hexanes:EtOAc (7:3). Yield: 26 mg, 32.4%. $^1$H NMR (400 MHz, CDCl$_3$): δ 10.32 (s, 1H), 8.55-8.05 (m, 3H), 7.85-7.54 (m, 1H), 3.08-2.87 (m, 2H), 2.90-2.64 (m, 2H), 1.86 (q, J=6.0 Hz, 2H), 1.68 (ddd, J=22.3, 10.9, 5.3 Hz, 4H), 1.34 (s, 9H). HR-ESIMS: m/z 355.2056 [M+H]$^+$ calcd for C$_{20}$H$_{27}$N$_4$O$_2$, found 355.2121. HPLC Purity: 96.31% (Retention Time=17.2 min).

(iv) N-(1-ethyl-5-methyl-1H-pyrazol-3-yl)-2-methoxy-6,7,8,9-tetrahydro-5H-cyclohepta[b]pyridine-3-carboxamide (39)

Purification on a pre-packed Silica gel column using Teledyne ISCO flash chromatographic system by CHCl$_3$:MeOH (9:1). Yield: 58 mg, 73.5%. $^1$H NMR (400 MHz, CDCl$_3$): δ 10.03 (s, 1H), 8.22 (s, 1H), 6.60 (s, 1H), 4.13 (d, J=4.7 Hz, 3H), 4.09-3.93 (m, 2H), 3.11-2.86 (m, 2H), 2.86-2.72 (m, 2H), 2.28 (s, 3H), 1.86 (s, 2H), 1.76-1.57 (m, 4H), 1.38 (t, J=7.2 Hz, 3H). HR-ESIMS: m/z 329.1899 [M+H]$^+$ calcd for C$_{18}$H$_{25}$N$_4$O$_2$, found 329.1971. HPLC Purity: 94.61% (Retention Time=15.0 min).

(v) 2-(4-(2-methoxy-6,7,8,9-tetrahydro-5H-cyclohepta[b]pyridine-3-carboxamido)phenyl)-2-methylpropanoic acid (40)

Purification on a pre-packed Silica gel column using Teledyne ISCO flash chromatographic system by Hexanes:EtOAc (1:1). Yield: 32 mg, 54.8%. $^1$H NMR (400 MHz, CDCl$_3$): $^1$H NMR (400 MHz, DMSO-d$_6$) δ 12.29 (s, 1H), 10.01 (s, 1H), 8.15-7.49 (m, 3H), 7.30 (d, J=7.7 Hz, 2H), 3.96 (s, 3H), 2.85 (d, J=71.4 Hz, 4H), 1.78 (d, J=30.0 Hz, 2H), 1.58 (s, 4H), 1.45 (s, 6H). HR-ESIMS: m/z 383.1893 [M+H]$^+$ calcd for C$_{22}$H$_{27}$N$_2$O$_4$ found 383.1971. HPLC Purity: 99.17% (Retention Time=13.3 min).

2. Characterization of Antiviral Agents

A list of compounds evaluated for antiviral activity is shown in Table 1 below.

TABLE 1

| No. | Structure | MW | EC$_{50}$ (μM) | CC$_{50}$ (μM) |
|---|---|---|---|---|
| 1 | 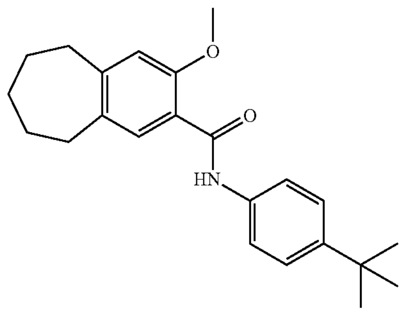 [SMILES: COc1cc2c(cc1C(=O)Nc1ccc(C(C)(C)C)cc1)CCCCC2] | 351.4 | 0.32 | >40 |
| 2 | 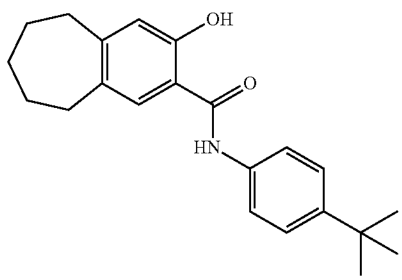 | 337.5 | 1.1 | 9.8 |
| 3 | 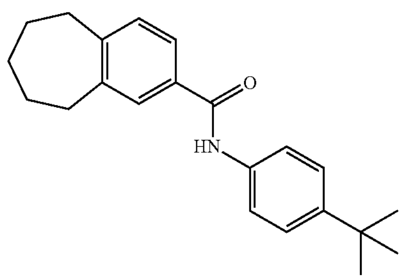 [SMILES: CC(C)(C)c1ccc(NC(=O)c2ccc3c(c2)CCCCC3)cc1] | 321.5 | 1.09 | >40 |
| 4 | 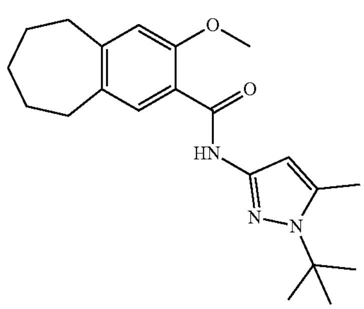 [SMILES: COc1cc2c(cc1C(=O)Nc1cc(C)n(C(C)(C)C)n1)CCCCC2] | 355.5 | 3.9 | 22.3 |
| 5 | 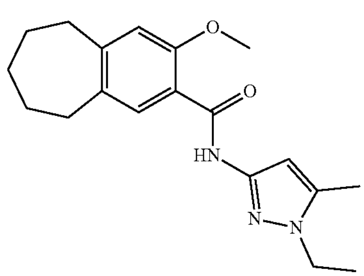 [SMILES: CCn1nc(NC(=O)c2cc3c(cc2OC)CCCCC3)cc1C] | 327.4 | 9.9 | >40 |

TABLE 1-continued

| No. | Structure | MW | EC$_{50}$ (μM) | CC$_{50}$ (μM) |
|---|---|---|---|---|
| 6 | 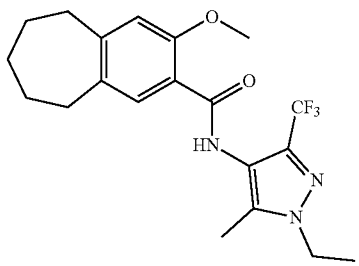 [SMILES: CCn1nc(C(F)(F)F)c(NC(=O)c2cc3c(cc2OC)CCCCC3)c1C] | 395.4 | 35.2 | >40 |
| 7 | 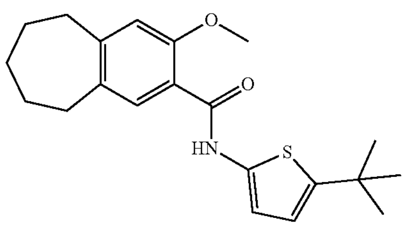 [SMILES: COc1cc2c(cc1C(=O)Nc1ccc(C(C)(C)C)s1)CCCCC2] | 357.5 | >40 | >40 |
| 8 | 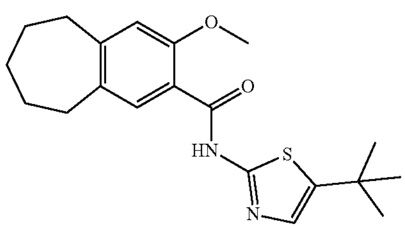 [SMILES: COc1cc2c(cc1C(=O)Nc1ncc(C(C)(C)C)s1)CCCCC2] | 358.5 | 9.63 | >40 |
| 9 | 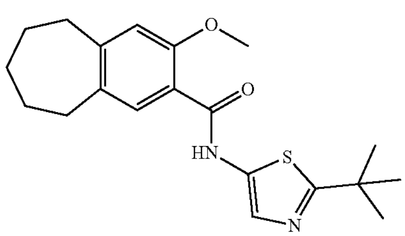 [SMILES: COc1cc2c(cc1C(=O)Nc1cnc(C(C)(C)C)s1)CCCCC2] | 358.5 | >40 | >40 |
| 10 | 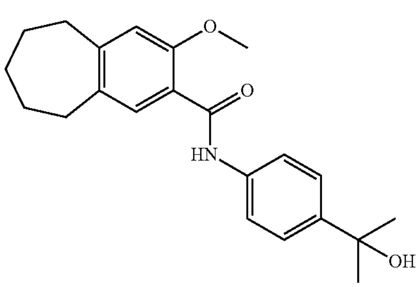 | 353.5 | 1.8 | 24.9 |
| 11 | 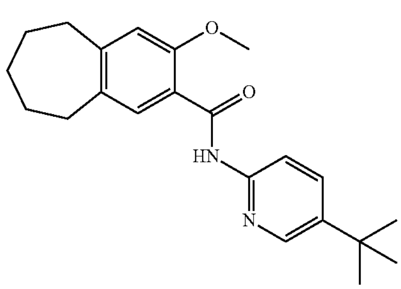 [SMILES: COc1cc2c(cc1C(=O)Nc1ccc(C(C)(C)C)cn1)CCCCC2] | 352.4 | 1.14 | >40 |

TABLE 1-continued

| No. | Structure | MW | EC$_{50}$ (µM) | CC$_{50}$ (µM) |
|---|---|---|---|---|
| 12 | 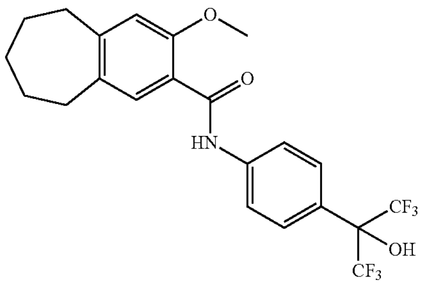 [SMILES: COc1cc2c(cc1C(=O)Nc1ccc(C(O)(C(F)(F)F)C(F)(F)F)cc1)CCCCC2] | 461.4 | >40 | >40 |
| 13 | 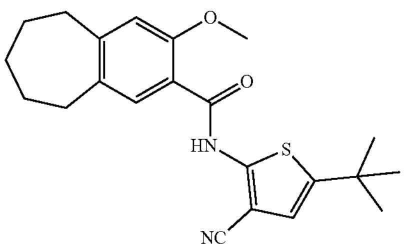 [SMILES: COc1cc2c(cc1C(=O)Nc1sc(C(C)(C)C)cc1C#N)CCCCC2] | 382.5 | >40 | >40 |
| 14 | 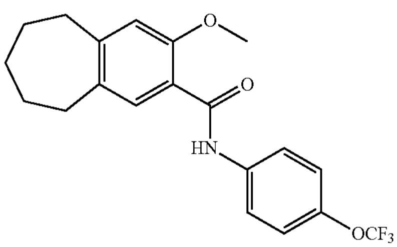 [SMILES: COc1cc2c(cc1C(=O)Nc1ccc(OC(F)(F)F)cc1)CCCCC2] | 379.4 | >40 | >40 |
| 15 | 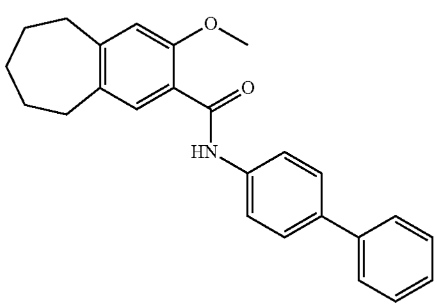 [SMILES: COc1cc2c(cc1C(=O)Nc1ccc(-c3ccccc3)cc1)CCCCC2] | 371.4 | >40 | >40 |
| 16 | 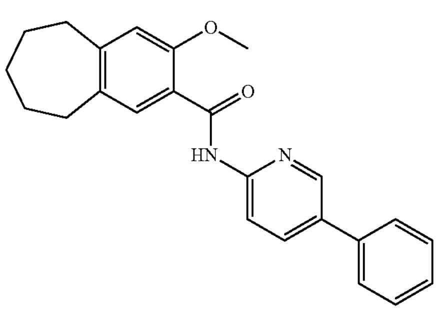 [SMILES: COc1cc2c(cc1C(=O)Nc1ccc(-c3ccccc3)cn1)CCCCC2] | 372.4 | >40 | >40 |

TABLE 1-continued

| No. | Structure | MW | EC$_{50}$ (μM) | CC$_{50}$ (μM) |
|---|---|---|---|---|
| 17 | 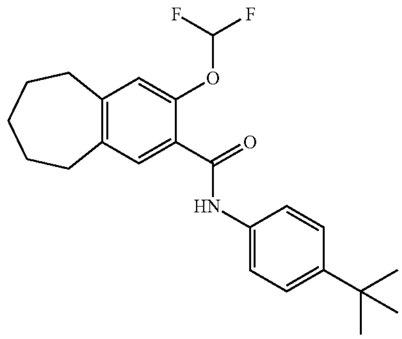 [SMILES: CC(C)(C)c1ccc(NC(=O)c2cc3c(cc2OC(F)F)CCCCC3)cc1] | 387.4 | >40 | >40 |
| 18 | 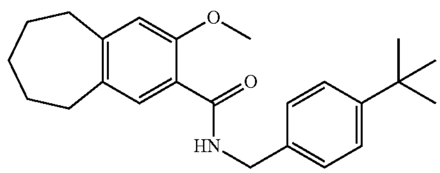 [SMILES: COc1cc2c(cc1C(=O)NCc1ccc(C(C)(C)C)cc1)CCCCC2] | 365.5 | 3.5 | >40 |
| 19 | 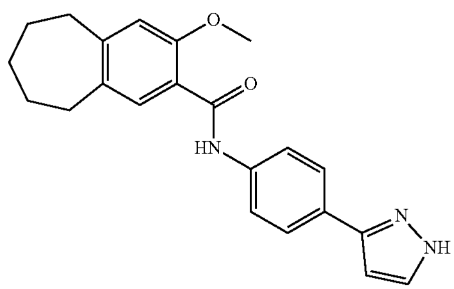 [SMILES: COc1cc2c(cc1C(=O)Nc1ccc(-c3cc[nH]n3)cc1)CCCCC2] | 361.4 | 3.65 | 23.25 |
| 20 | 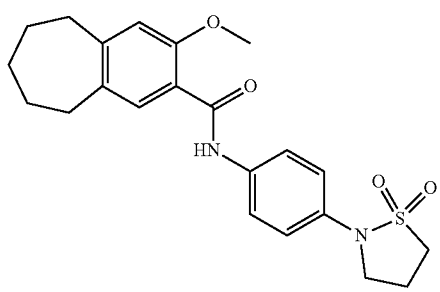 [SMILES: COc1cc2c(cc1C(=O)Nc1ccc(N3CCCS3(=O)=O)cc1)CCCCC2] | 414.5 | >5 | >40 |
| 21 | 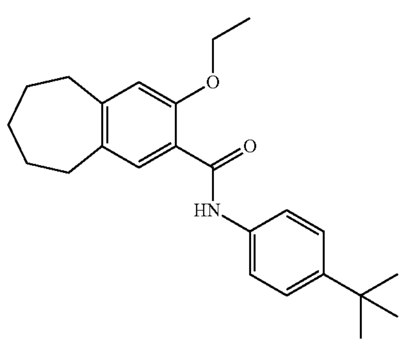 [SMILES: CCOc1cc2c(cc1C(=O)Nc1ccc(C(C)(C)C)cc1)CCCCC2] | 365.5 | 29.9 | >40 |

TABLE 1-continued

| No. | Structure | MW | EC$_{50}$ (μM) | CC$_{50}$ (μM) |
|---|---|---|---|---|
| 22 | 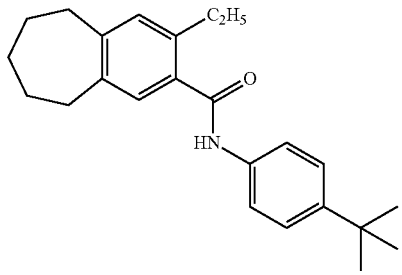 [SMILES: CCc1cc2c(cc1C(=O)Nc1ccc(C(C)(C)C)cc1)CCCCC2] | 349.5 | >40 | >40 |
| 23 | 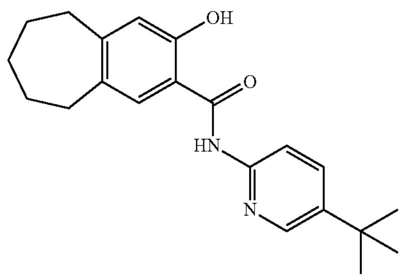 [SMILES: CC(C)(C)c1ccc(NC(=O)c2cc3c(cc2O)CCCCC3)nc1] | 338.4 | 3.8 | >40 |
| 24 | 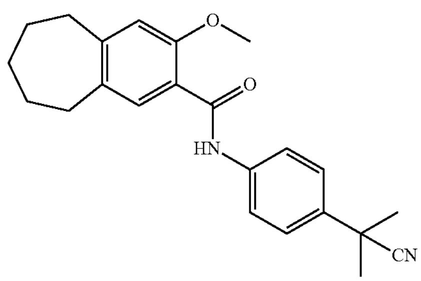 [SMILES: COc1cc2c(cc1C(=O)Nc1ccc(C(C)(C)C#N)cc1)CCCCC2] | 362.4 | 0.20 | >40 |
| 25 | 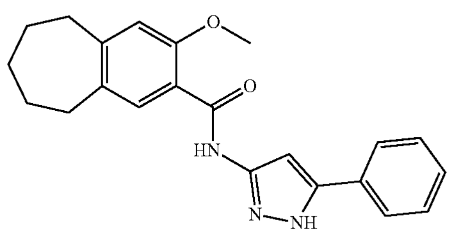 [SMILES: COc1cc2c(cc1C(=O)Nc1cc(-c3ccccc3)[nH]n1)CCCCC2] | 361.1 | >40 | >40 |
| 26 | 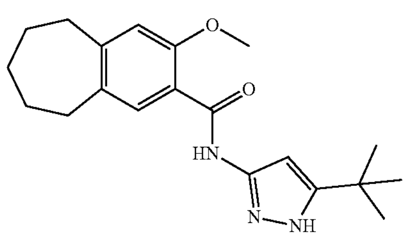 [SMILES: COc1cc2c(cc1C(=O)Nc1cc(C(C)(C)C)[nH]n1)CCCCC2] | 341.2 | 7.03 | 15.5 |
| 27 | 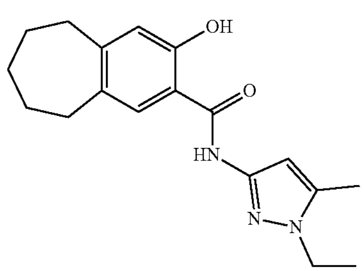 [SMILES: CCn1nc(NC(=O)c2cc3c(cc2O)CCCCC3)cc1C] | 313.3 | >40 | >40 |

TABLE 1-continued
| No. | Structure | MW | EC$_{50}$ (μM) | CC$_{50}$ (μM) |
| --- | --- | --- | --- | --- |
| 28 | 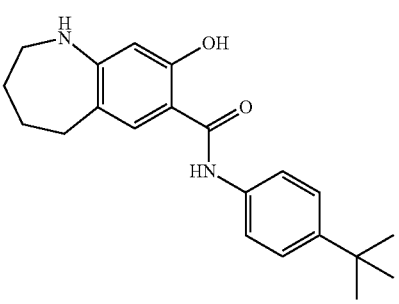 [SMILES: CC(C)(C)c1ccc(NC(=O)c2cc3c(cc2O)NCCCC3)cc1] | 338.4 | 1.47 | >40 |
| 29 | 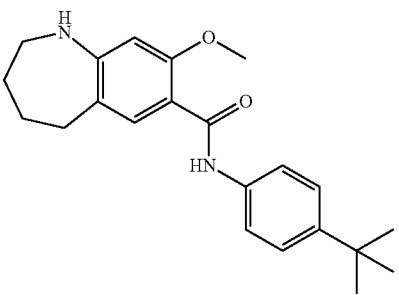 [SMILES: COc1cc2c(cc1C(=O)Nc1ccc(C(C)(C)C)cc1)CCCCN2] | 352.4 | 24.4 | >40 |
| 30 | 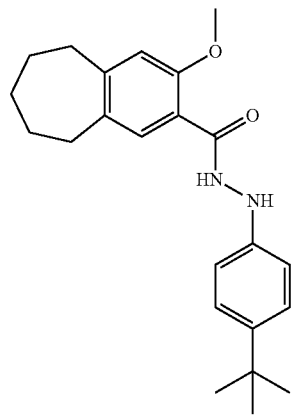 [SMILES: COc1cc2c(cc1C(=O)NNc1ccc(C(C)(C)C)cc1)CCCCC2] | 366.4 | >40 | >40 |
| 31 | 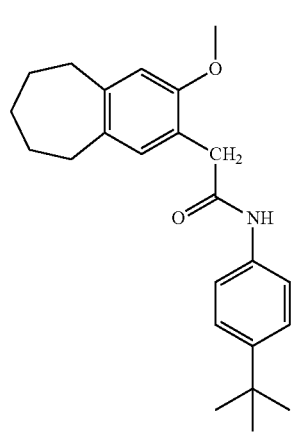 [SMILES: COc1cc2c(cc1CC(=O)Nc1ccc(C(C)(C)C)cc1)CCCCC2] | 365.5 | 30.4 | >40 |

TABLE 1-continued

| No. | Structure | MW | EC$_{50}$ (μM) | CC$_{50}$ (μM) |
|---|---|---|---|---|
| 32 | 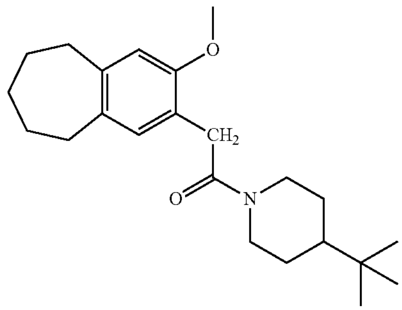 [SMILES: COc1cc2c(cc1CC(=O)N1CCC(C(C)(C)C)CC1)CCCCC2] | 357.5 | 12.6 | 17.3 |
| 33 | 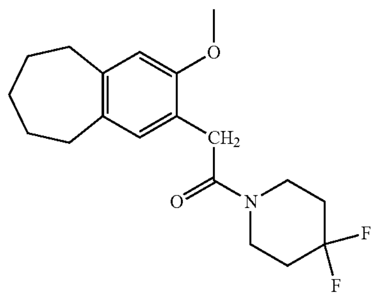 [SMILES: COc1cc2c(cc1CC(=O)N1CCC(F)(F)CC1)CCCCC2] | 337.4 | >40 | >40 |
| 34 | 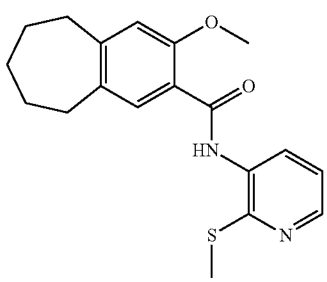 [SMILES: COc1cc2c(cc1C(=O)Nc1cccnc1SC)CCCCC2] | 342.4 | >40 | >40 |
| 35 | 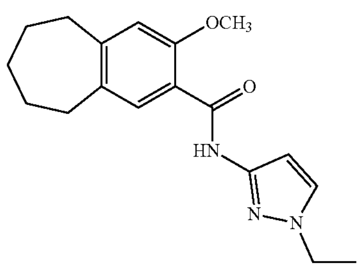 [SMILES: CCn1ccc(NC(=O)c2cc3c(cc2OC)CCCCC3)n1] | 313.4 | 17.4 | >40 |
| 36 | 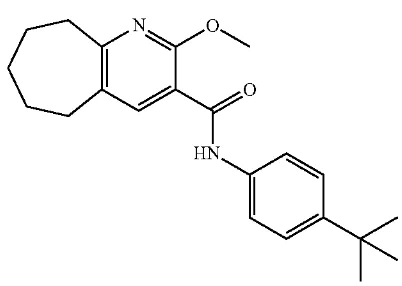 [SMILES: COc1nc2c(cc1C(=O)Nc1ccc(C(C)(C)C)cc1)CCCCC2] | 352.5 | 1.71 | >40 |

TABLE 1-continued

| No. | Structure | MW | EC$_{50}$ (μM) | CC$_{50}$ (μM) |
|---|---|---|---|---|
| 37 | 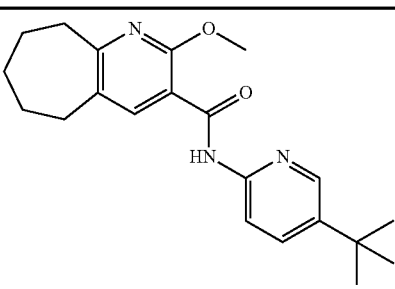 | 353.5 | 13.6 | >40 |
| 38 | 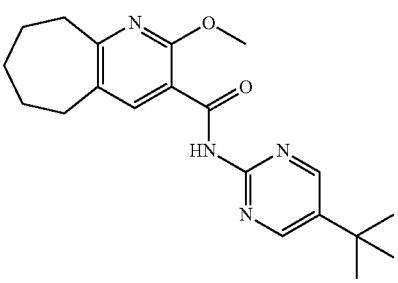 [SMILES: COc1nc2c(cc1C(=O)Nc1ncc(C(C)(C)C)cn1)CCCCC2] | 354.5 | 19.4 | >40 |
| 39 | 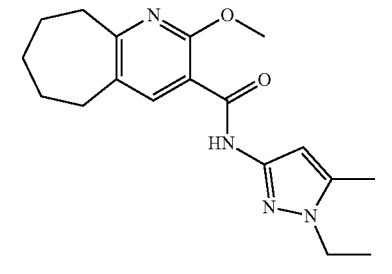 [SMILES: CCn1nc(NC(=O)c2cc3c(nc2OC)CCCCC3)cc1C] | 328.4 | 30.72 | >40 |
| 40 | 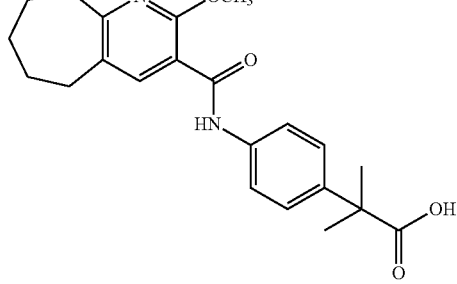 | 382.4 | >40 | >40 |

G. Prophetic Examples

1. Pharmacokinetic/Brain Penetration Study in Sprague Dawley Rats

Each study in rats will include three groups of animals with indwelling jugular vein cannulas, consisting of three male Sprague Dawley rats per group, aged 8-12 weeks and weighing 200-250 grams. Each animal will be given a single dose (e.g., iv or po) of test compound at a dose level to be determined (TBD). Without wishing to be bound by theory, it is anticipated that the dose level of each compound given orally will be in the range of 10-20 mg/kg, and that given iv, 2-5 mg/kg, or as limited by the solubility of the test compound. Each test compound will be formulated in an appropriate vehicle for administration to animals. Study procedures will include clinical observations, measurement of body weights and collection of blood for plasma drug level determinations. For animals in Groups 1 and 2, blood (<0.45 mL) will be collected from an indwelling jugular vein cannula prior to dosing and at specified time points after dosing (see below). For animals in Group 3, blood (<0.45 mL) will be collected from an indwelling jugular vein cannula at 1 hour after dosing. Importantly, dose administration (iv administration) and blood collection will occur via separate jugular vein ports. Immediately after final blood collection, each animal will be euthanized by CO$_2$ asphyxiation; the brain will be collected from each animal in Group 3 only and immediately frozen in liquid nitrogen. Each blood sample will be centrifuged to separate plasma. Plasma and brain samples will be analyzed by HLPC/MS/MS for levels of unchanged test compound and metabolites, as appropriate. Relevant pharmacokinetic parameters, oral bioavailability, and plasma/brain ratio will be calculated for each test compound via WinNonlin®.

2. Pharmacokinetic/Brain Penetration Study in Cd-1 Mice

Each study will include two groups, consisting of 12 male mice/group, aged 6-7 weeks and weighing 22-24 grams for a total of 24 animals. Each mouse will be given a single dose of test compound (e.g., iv or po) of test compound. The vehicle for test compound administration, as well as the dose level of test compound will be determined as described above for the rat PK study. Mice in each dose group will be divided into four subgroups consisting of three mice per subgroup. Study procedures will include clinical observations, measurement of body weights and collection of blood for plasma drug level determinations. Blood (~0.25 mL) will be collected from the submandibular vein in each subgroup at alternating time points, such that each mouse is bled no more than twice. Following final blood collection, animals will be euthanized by $CO_2$ asphyxiation. The brain will be collected from three animals in each of four subgroups (A-D) in Group 1 that are euthanized at 1, 4, 8, or 24 hours after iv dosing. Brains will be immediately frozen in liquid nitrogen, and each blood sample will be centrifuged to separate plasma. Plasma and brain samples will be stored at <-80° C. and subsequently analyzed by HPLC/MS/MS for levels of unchanged test compound and metabolites, as appropriate. Relevant pharmacokinetic parameters, oral bioavailability, and plasma/brain ratio will be calculated for each test compound via WinNonlin®.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

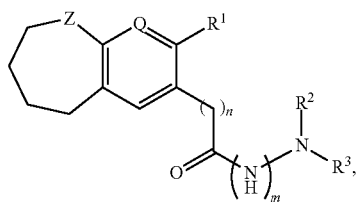

wherein each of m and n is independently selected from 0 and 1;
wherein Q is selected from CH and N;
wherein Z is selected from NH and $CH_2$;
wherein $R^1$ is selected from hydrogen, —OH, C1-C4 alkyl, C1-C4 haloalkoxy, and C1-C4 alkoxy;
wherein $R^2$ is hydrogen; and
wherein $R^3$ is C2-C5 heteroaryl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)$Ar^1$, and $Ar^1$;
wherein $Ar^1$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl;

or wherein $R^3$ is a structure represented by a formula:

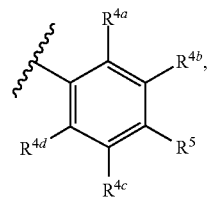

wherein each of $R^{4a}$, $R^{4b}$, $R^{4c}$, and $R^{4d}$ is independently selected from hydrogen, halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, and $Ar^2$;
wherein $Ar^2$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl;
wherein $R^5$ is selected from hydrogen, halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, —(C1-C4 alkyl)$CO_2H$, and $Ar^3$; and
wherein $Ar^3$, when present, is selected from cycloalkyl, monocyclic aryl, heterocycloalkyl, and heteroaryl, and is substituted with 0, 1, 2, or 3 groups independently selected from halogen, C1-C4 alkyl, and C1-C4 haloalkyl;

or wherein each of $R^2$ and $R^3$ are covalently bonded together and, together with the intermediate atoms, comprise a 3- to 6-membered heterocycloalkyl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino;

provided that when n is 1 and $R^1$ is hydrogen, then $R^3$ is not pyridinyl, provided that when n is 1, then $R^5$ is not hydrogen, or provided that when $R^5$ is hydrogen, then $R^1$ is not hydrogen, or a pharmaceutically acceptable salt thereof.

2. The compound of claim 1, wherein m is 0.

3. The compound of claim 1, wherein n is 0 and $R^5$ is not hydrogen.

4. The compound of claim 1, wherein each of m and n is 0.

5. The compound of claim 4, wherein $R^5$ is not hydrogen.

6. The compound of claim 1, wherein $R^1$ is selected from —OH and C1-C4 alkoxy.

7. The compound of claim 1, wherein $R^3$ is C2-C5 heteroaryl substituted with 0, 1, 2, or 3 groups independently selected from halogen, —CN, —$NH_2$, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)$Ar^1$, and $Ar^1$.

8. The compound of claim 7, wherein $R^3$ is selected from pyrazolyl, thiazolyl, and pyridinyl.

9. The compound of claim 7, wherein R³ is a structure:

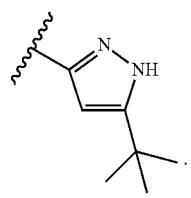 [SMILES: *c1cc(C(C)(C)C)[nH]n1]

10. The compound of claim 1, wherein R³ is a structure represented by a formula:

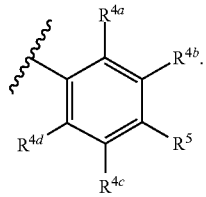

11. The compound of claim 10, wherein R³ is a structure:

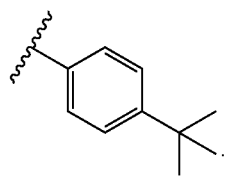 [SMILES: *c1ccc(C(C)(C)C)cc1]

12. The compound of claim 1, wherein each of R² and R³ are covalently bonded together and, together with the intermediate atoms, comprise a 3- to 6-membered heterocycloalkyl substituted with 0, 1, 2, or 3 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, and (C1-C4)(C1-C4) dialkylamino.

13. The compound of claim 1, wherein the compound has a structure represented by a formula:

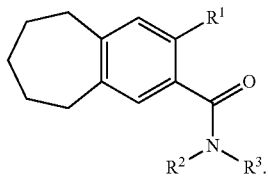

14. The compound of claim 1, wherein the compound has a structure represented by a formula:

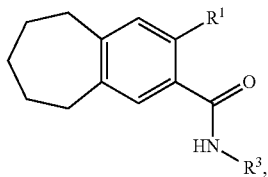

wherein R¹ is selected from hydrogen, —OH, C1-C4 alkyl, and C1-C4 alkoxy; and
wherein R³ is heteroaryl substituted with 0, 1, 2, or 3 groups independently selected from halogen, —CN, —NH₂, —OH, C1-C4 alkyl, C1-C4 haloalkyl, C1-C4 cyanoalkyl, C1-C4 hydroxyalkyl, C1-C4 alkoxy, C1-C4 alkylamino, (C1-C4)(C1-C4) dialkylamino, (C1-C4 alkyl)Ar¹, and Ar¹.

15. The compound of claim 1, wherein the compound has a structure represented by a formula:

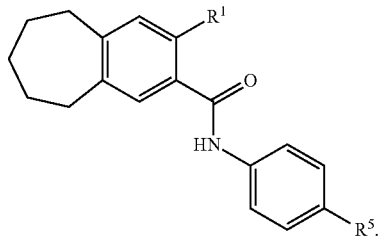

16. The compound of claim 1, wherein the compound is selected from:

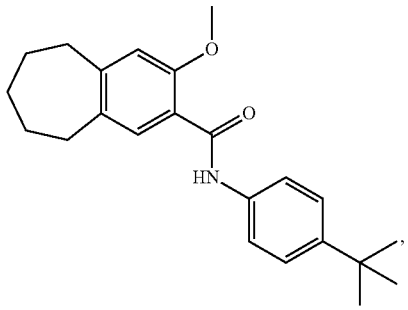

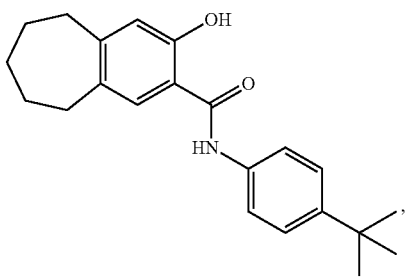

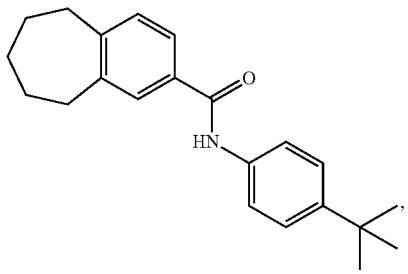

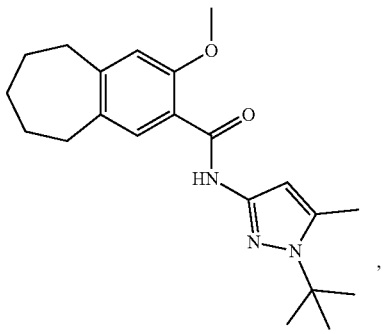

145
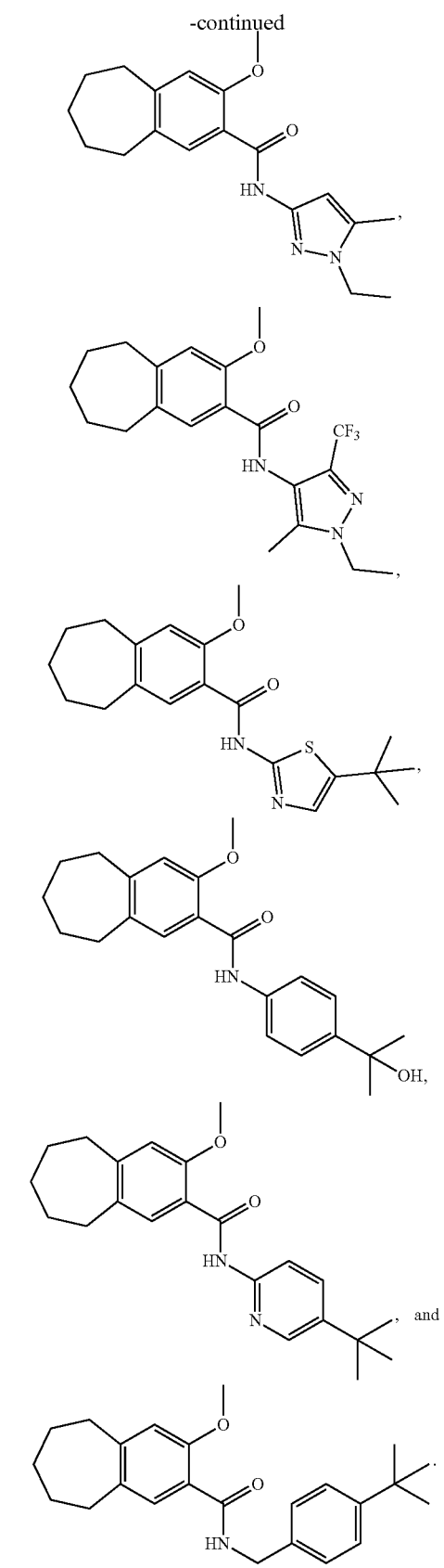
146
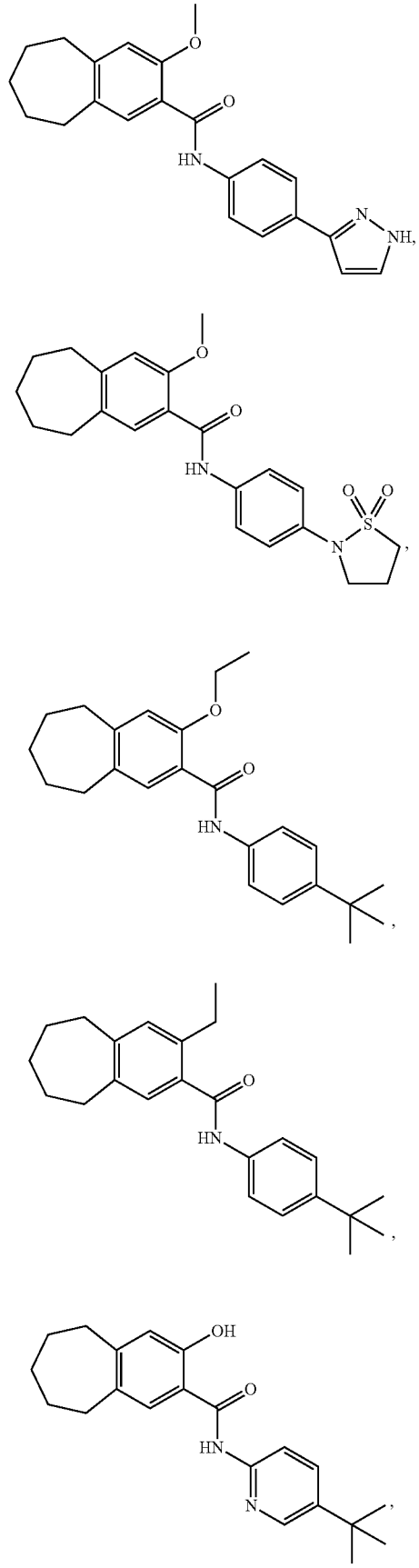
17. The compound of claim 1, wherein the compound is selected from:

-continued
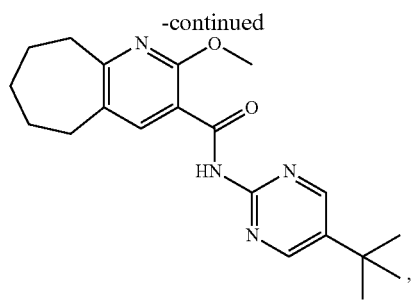
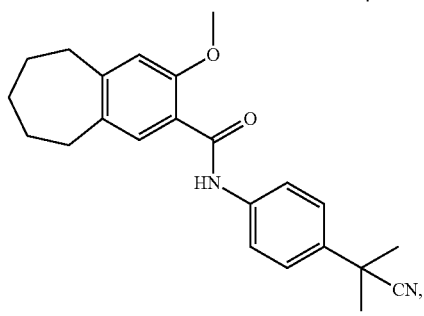
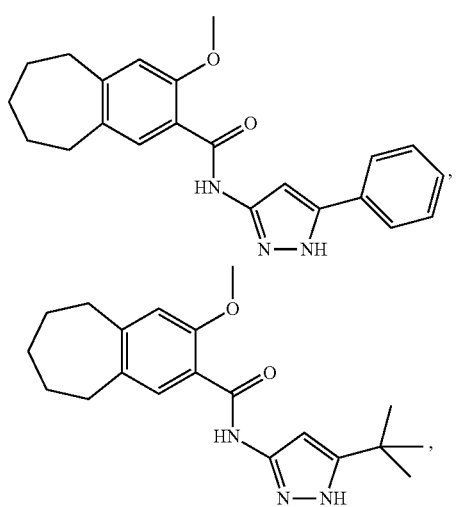
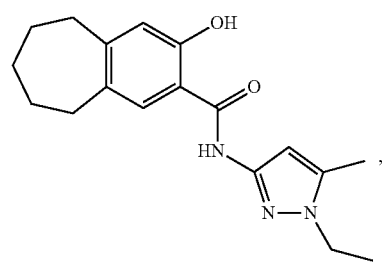
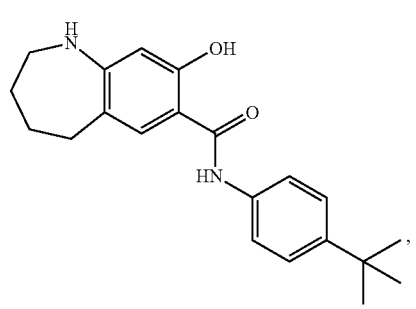
-continued
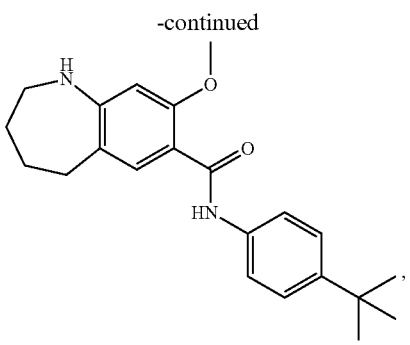
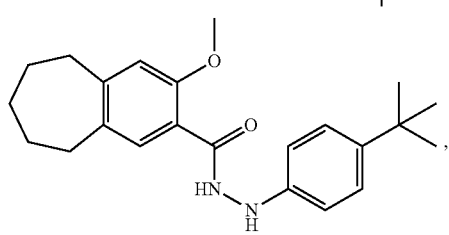
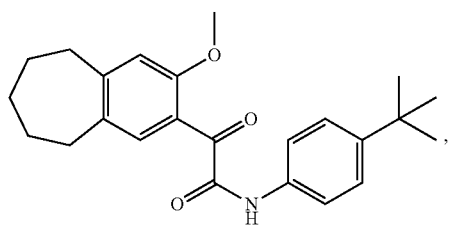
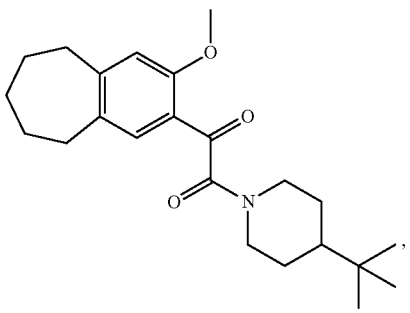
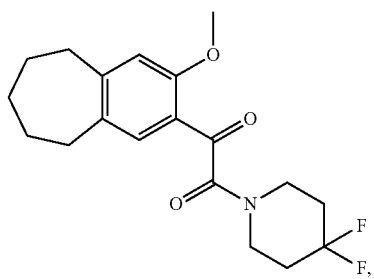
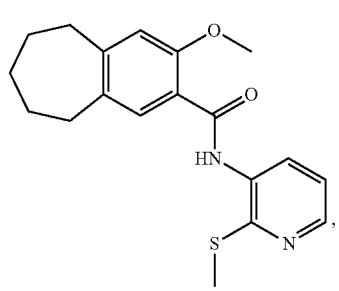

149
-continued

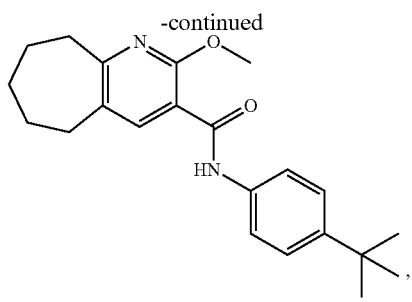

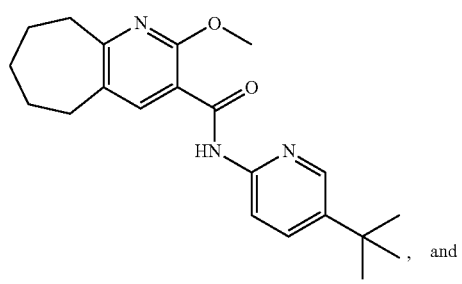
and

150
-continued

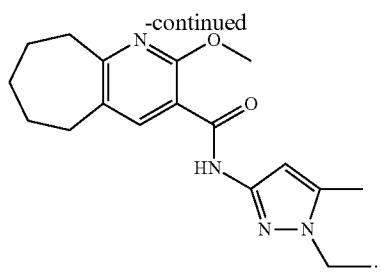

18. A pharmaceutical composition comprising a therapeutically effective amount of at least one compound of claim 1 and a pharmaceutically acceptable carrier.

19. A method for the treatment of a viral infection in a subject having the viral infection, the method comprising the step of administering to the subject a therapeutically effective amount of at least one compound of claim 1, wherein the subject has been diagnosed as having the viral infection prior to the administering step.

20. The method of claim 19, wherein the viral infection is selected from chikungunya, Venezuelan equine encephalitis, dengue, influenza, and zika.

* * * * *

UNITED STATES PATENT AND TRADEMARK OFFICE
CERTIFICATE OF CORRECTION

| | | |
|---|---|---|
| PATENT NO. | : 11,066,357 B2 | Page 1 of 1 |
| APPLICATION NO. | : 16/954464 | |
| DATED | : July 20, 2021 | |
| INVENTOR(S) | : Ashish Kumar Pathak et al. | |

It is certified that error appears in the above-identified patent and that said Letters Patent is hereby corrected as shown below:

In the Specification

Column 1, replace Lines 17-20 after the heading "STATEMENT REGARDING FEDERALLY SPONSORED RESEARCH" with the following:
--"This invention was made with government support under AI142759 and U19 AI109680 awarded by the National Institutes of Health. The government has certain rights in the invention."--

Signed and Sealed this
Twenty-sixth Day of August, 2025

Coke Morgan Stewart
*Acting Director of the United States Patent and Trademark Office*